(12) United States Patent
Lin et al.

(10) Patent No.: US 8,338,366 B2
(45) Date of Patent: Dec. 25, 2012

(54) BIOACTIVE FUS1 PEPTIDES AND NANOPARTICLE-POLYPEPTIDE COMPLEXES

(75) Inventors: Jacki Lin, Houston, TX (US); Ralph B. Arlinghaus, Bellaire, TX (US); Tong Sun, Pearland, TX (US); Lin Ji, Sugar Land, TX (US); Bulent Ozpolat, Houston, TX (US); Gabriel Lopez-Berestein, Bellaire, TX (US); Jack A. Roth, Houston, TX (US)

(73) Assignee: The Board of Regents of the University of the Texas System, Austin, TX (US)

( * ) Notice: Subject to any disclaimer, the term of this patent is extended or adjusted under 35 U.S.C. 154(b) by 1313 days.

(21) Appl. No.: 11/375,544

(22) Filed: Mar. 14, 2006

(65) Prior Publication Data

US 2006/0251726 A1  Nov. 9, 2006

Related U.S. Application Data

(60) Provisional application No. 60/753,632, filed on Dec. 22, 2005, provisional application No. 60/661,680, filed on Mar. 14, 2005.

(51) Int. Cl.
| | |
|---|---|
| A61K 31/00 | (2006.01) |
| A61K 38/04 | (2006.01) |
| A61K 51/00 | (2006.01) |
| A61K 47/00 | (2006.01) |
| A01N 61/00 | (2006.01) |
| C07K 2/00 | (2006.01) |
| C07K 4/00 | (2006.01) |
| C07K 5/00 | (2006.01) |
| C07K 7/00 | (2006.01) |
| C07K 14/00 | (2006.01) |
| C07K 16/00 | (2006.01) |
| C07K 17/00 | (2006.01) |

(52) U.S. Cl. ......... 514/1.2; 530/326; 530/300; 530/333; 977/705; 977/906; 424/1.69; 514/1.1

(58) Field of Classification Search ....................... None
See application file for complete search history.

(56) References Cited

U.S. PATENT DOCUMENTS

| 5,030,453 A | 7/1991 | Lenk et al. | 424/450 |
| 5,236,783 A | 8/1993 | Aoki et al. | 428/403 |
| 5,368,933 A | 11/1994 | Aoki et al. | 428/329 |

(Continued)

FOREIGN PATENT DOCUMENTS

WO    WO 00/58339    10/2000

(Continued)

OTHER PUBLICATIONS

PCT Invitation to Pay Additional Fees, issued in International Application No. PCT/US2006/009044, dated Apr. 21, 2008.

(Continued)

*Primary Examiner* — Maury Audet
(74) *Attorney, Agent, or Firm* — Parker Highlander PLLC

(57) ABSTRACT

A nanoparticle-polypeptide complex comprising a bioactive polypeptide in association with a nanoparticle, wherein the bioactive polypeptide is modified by the addition of a chemical moiety that facilitates cellular uptake of the protein. The polypeptide can be a protein or a peptide. In some embodiments, the amino acid sequence of the protein or peptide is derived from the amino acid sequence of a tumor suppressor gene product.

31 Claims, 26 Drawing Sheets

U.S. PATENT DOCUMENTS

| | | | |
|---|---|---|---|
| 5,417,978 A | 5/1995 | Tari et al. | 424/450 |
| 5,962,016 A | 10/1999 | Willis | 424/450 |
| 6,011,013 A * | 1/2000 | Carr et al. | 514/9.8 |
| 6,358,523 B1 | 3/2002 | Safinya et al. | 424/450 |
| 6,413,544 B1 | 7/2002 | Smyth-Templeton et al. | 424/450 |
| 6,416,544 B2 | 7/2002 | Sugita et al. | 623/1.19 |
| 6,468,793 B1 | 10/2002 | Teem | 435/325 |
| 6,610,657 B1 * | 8/2003 | Goueli | 514/21.2 |
| 6,660,830 B1 | 12/2003 | Radulescu | 530/300 |
| 6,680,068 B2 | 1/2004 | Campbell et al. | 424/450 |
| 6,750,327 B2 | 6/2004 | Melmed et al. | 530/387.9 |
| 6,770,291 B2 | 8/2004 | Smyth-Templeton et al. | 424/450 |
| 6,784,157 B2 | 8/2004 | Halazonetis et al. | 514/12 |
| 6,858,586 B2 | 2/2005 | Horwitz et al. | 514/12 |
| 2002/0164715 A1 | 11/2002 | Ji et al. | 435/69.5 |
| 2003/0012812 A1 | 1/2003 | Tormo et al. | 424/450 |
| 2003/0054007 A1 | 3/2003 | Felgner et al. | 424/178.1 |
| 2003/0077225 A1 | 4/2003 | Laurent et al. | 424/9.3 |
| 2004/0016006 A1 * | 1/2004 | Ji et al. | 800/8 |
| 2004/0126900 A1 | 7/2004 | Barry et al. | 436/523 |
| 2004/0151766 A1 | 8/2004 | Monahan et al. | 424/450 |
| 2004/0164715 A1 | 8/2004 | Nawa et al. | 320/149 |
| 2004/0197393 A1 | 10/2004 | Smyth-Templeton et al. | 424/450 |
| 2004/0265233 A1 | 12/2004 | Holzer et al. | 424/9.32 |
| 2005/0187147 A1 * | 8/2005 | Newman et al. | 514/8 |

FOREIGN PATENT DOCUMENTS

| | | |
|---|---|---|
| WO | WO 0204511 | 1/2002 |

OTHER PUBLICATIONS

Yoo et al., "Protein-fatty acid complex for enhanced loading and stability within biodegradable nanoparticles," *J. Pharm. Sci.*, 90:194-201, 2001.

Zhang et al., "Surface modification of superparamagnetic magnetite nanoparticles and their intracellular uptake," *Biomaterials*, 23:1553-1561, 2002.

Aiello, "Keeping in touch with angiogenesis," *Nature Medicine*, 6:379, 2000.

Bagorda et al., "Reciprocal protein kinase a regulatory interactions between cystic fibrosis transmembrane conductance regulator and $Na^+/H^+$ exchanger isoform 3 in a renal polarized epithelial cell model," *J Bio Chem*, 277:21480-21488, 2002.

Bailey and Sullivan, "Efficient encapsulation of DNA plasmids in small neutral liposomes induced by ethanol and calcium," *Biochimica et Biophysica Acta*, 1468:239-252, 2000.

Butturini et al., "Concise report BCR/ABL and leukemia," *Leukemia Res.*, 20(6):523-529, 1996.

Colledge and Scott, "AKAPs: from structure to function," *Cell Biology*, 9:216-221, 1999.

Dhoot and Wheatley, "Microencapsulated liposomes in controlled drug deliver: strategies to modulate drug release and eliminate the burst effect," *J Pharm Sci*, 92:679-689, 2003.

Drin et al., "Peptide delivery to the brain via absorptive-mediated endocytosis: advances with synb vectors," *AAPS PharmSci*, 4:1-7, 2002.

Du et al., "Conformational and topological requirements of cell-permeable peptide function," *J. Pept. Res.*, 51:235-243, 1998.

Ellerby et al., "Anti-cancer activity of targeted pro-apoptotic peptides," *Nature Medicine*, 5:1032-1038, 1999.

Ji et al., "Expression of several genes in the human chromosome 3p21.3 homozygous deletion region by an adenovirus vector results in tumor suppressor activities in vitro and in vivo," *Cancer Research*, 62:2715-2720, 2002.

Khalil et al., "Mechanism of improved gene transfer by the n-terminal stearylation of octaarginine: enhanced cellular association by hydrophobic core formation," *Gene Therapy*, 11:636-644, 2004.

Kieber-Emmons et al., "Therapeutic peptides and peptidomimetics," *Current Opinion in Biotechnology*, 8:435-441, 1997.

Kim et al., "Detection of liver metastases: gadobenate dimeglumine-enhanced three-dimensional dynamic phases and one-hour delayed phase mr imaging versus superparamagnetic iron oxide-enhanced mr imaging," *Eur Radiol*, 15:220-228, 2005.

Kondo et al., "Overexpression of candidate tumor suppressor gene *fus 1* isolated from the 3p21.3 homozygous deletion region leads to g1 arrest and growth inhibition of lung cancer cells," *Oncogene*, 20:6258-6262, 2001.

Latham, "Therapeutic peptides revisited," *Nature Biotechnology*, 17:755757, 1999.

Lerman and Minna, "The 630-kb lung cancer homozygous deletion region on human chromosome 3p21.3: identification and evaluation of the resident candidate tumor suppressor genes," *Cancer Research*, 60:6116-6133, 2000.

Lien and Lowman, "Therapeutic peptides," *TRENDS in Biotechnology*, 21:556-562, 2003.

Lin et al., "BCR gene expression blocks bcr-abl induced pathogenicity in a mouse model," *Oncogene*, 20:1873-1881, 2001.

Ling et al., "Bcr and abl interaction: oncogenic activation of c-abl by sequestering bcr," *Cancer Res.*, 63:298-303, 2003.

Liu et al., "The two regulatory subunits of aplysia camp-dependent protein kinase mediate distinct functions in production synaptic plasticity," *Journal of Neuroscience*, 24:2465-2474, 2004.

Miller et al., "Increased c-crk proto-oncogene expression is associated with an aggressive phenotype in lung adenocarcinomas," *Oncogene*, 22:6006-6013, 2003.

Morawski et al., "Targeted contrast agents for magnetic resonance imaging and ultrasound," *Current Opinion in Biotechnology*, 16:89-92, 2005.

Netz et al., "Mode of action of the antimicrobial peptide aureocin a53 from *Staphylococcus aureus*," *Applied and Environmental Microbiology*, 68:5274-5280, 2002.

Nishihara et al., "Molecular and immunohistochemical analysis of signaling adaptor protein crk in human cancers," *Cancer Letter*, 180(1):55-61, 2002.

Portefaix et al., "Peptides derived from the two regulatory domains of p53 are recognized by two p53-activating antibodies," *Peptides*, 24:339-345, 2003.

Rojas et al., "Controlling epidermal growth factor (egf)-stimulated ras activation in intact cells by a cell-permeable peptide mimicking phosphoylated egf receptor," *J. Biol. Chem.*, 271:27456-27461, 1996.

Rojas et al., "Genetic engineering of proteins with cell membrane permeability," *Nature Biotechnol.*, 16:370-375, 1998.

Rosenberg et al., "Cancer immunotherapy: moving beyond current vaccines," *Nature Medicine*, 10:909915, 2004.

Schlievert, "Will therapeutic peptides be kryptonite for superantigens?" *Nature Medicine*, 6:378, 2000.

Schwarze et al., "In vivo protein transduction: delivery of a biologically active protein into the mouse," *Science*, 285:1569-1572, 1999.

Schwarze et al., "Protein transduction: unrestricted delivery into all cells?," *Trends Cell Biol.*, 10:290-295, 2000.

Shih et al., "Dynamic complexes of $\beta_2$-adrenergic receptors with protein kinases and phosphatases and the role of gravin," *J Bio Chem*, 274:1588-1595, 1999.

Templeton et al., "Improved DNA: liposome complexes for increased systemic delivery and gene expression," *Nature Biotechnology*, 15:647-652, 1997.

Uno et al., "Myristolyation of the fus1 protein is required for tumor suppression in human lung cancer cells," *Cancer Research*, 64:2969-2976, 2004.

Wang, "Regulation of cell death by the abl tyrosine kinase," *Oncogene*, 19(49):5643-5650, 2000.

Wen and Van Etten, "The *pag* gene product, a stress-induced protein with antioxidant properties, is an abl sh3-binding protein and a physiological inhibitor of c-abl tyrosine kinase activity," *Genes & Development*, 11:2456-2467, 1997.

Whitesides, "The 'right' size in nanobiotechnology," *Nature Biothechnolgy*, 21:1161-1165, 2003.

Enochs et al., "Improved delineation of human brain tumors on mr images using a long-circulating, superparamegnetic iron oxide agent," *Journal of Magnetic Resonance Imaging*, 9:228-232, 1999.

Fenske et al., "Long-circulating vectors for the systemic delivery of genes," *Current Opinion in Molecular Therapeutics*, 3:153-158, 2001.

Ferrari, "Cancer nanotechnology: opportunities and challenges," *Nature Reviews*, 5:161-171, 2005.

Friedler et al., "A peptide that binds and stabilizes p53 core domain: chaperone strategy for rescue of oncogenic mutants," *PNAS*, 99:937-942, 2002.

Gopalan et al., "Nanoparticle based systemic gene therapy for lung cancer: molecular mechanisms and strategies to suppress nanoparticle-mediated inflammatory response," *Technology in Cancer Research & Treatment*, 3:647-657, 2004.

Goueli and Hsaio, "Using InCELLect™ cell-permeable, stearated peptides to probe camp-dependent protein kinase-mediated cellular signaling reactions in vivo," www.promega.com, 2000.

Gupta and Gupta, "Synthesis and surface engineering of iron oxide nanoparticles for biomedical applications," *Biomaterials*, 26:3995-4021, 2005.

Gutiérrez-Puente et al., "Safety, pharmacokinetics, and tissue distribution of liposomal p-ethoxy antisense oligonucleotides targeted to bcl-2," *J Pharmacology and Experimental Therapeutics*, 291:865-869, 1999.

Hantschel et al., "A Myristoyl/Phosphotyrosine switch regulates c-abl," *Cell*, 112:845-857, 2003.

Hu and Yuan, "Preparation and characterization of solid lipid nanoparticles containing peptide," *International Journal of Pharmaceutics*, 273:29-35, 2004.

Hvalby et al., "Specifictiy of protein kinase inhibitor peptides and induction of long-term potentiation," *Proc Natl Acad Sci USA*, 91:4761-4765, 1994.

Imgartinger et al., Pulmonary delivery of therapeutic peptides via dry powder inhalation: effects of micronisation and manufacturing, *European J Pharmaceutics and Biopharmaceutics*, 58:7-14, 2004.

Ito et al., "Liposomal vector mediated delivery of the 3p fus1 gene demonstrates potent amtitumor activity against human lung cancer in vivo," *Cancer Gene Therapy*, 11:733-739, 2004.

Iyer et al., "Noninvasive imaging of cationic lipid-mediated delivery of optical and pet reporter genes in living mice," *Molecular Therapy*, 6:555-562, 2002.

* cited by examiner

Fig. 1. Potential Therapeutic Peptides Derived from Fus1 Protein Sequence

Fig. 2. Hydrophobic Constants derived from HPLC Peptide Retention Times by Wilson, Honegger, Stotzel, Hughes Model Fig. 3. Prediction Polarity of wt-FUS1 and mt-FUS1 Peptides By Zimmerman J.M., Eliezer N., Simha R Model Fig. 4. Schematic Diagram of SPIO-peptide Nanoparticle (SPN)

Fig. 5. Structure of DOTAP:Cholesterol-encapsulated Therapeutic Peptide Nanoparticle (DC-PN) and SPIO-Peptide Nanoparticle (DC-SPN) for Anticancer Therapy by Systemic Administration and for in vivo Imaging by MR Fig. 6. Effects of Fus1 Peptide on Growth of NSCLC Cell Fig. 7. IC50 values of stearate-wt-FP in NSCLC and normal bronchial epithelial CDD16 cells.

Fig. 8. Effects of Fus1 Peptide (FP) on Cell Growth and Apoptosis in SCLC H128 and H146 Cells (48 h)

Fig. 9. Effects of Combination Treatment with FUS1 Peptide and Gefitinib in Gefitinib-sensistive (S) and resistant (R)-NSCLC Cells.

Fig. 10. Effects of Wt-FUS1 and FUS1-peptide on Growth of SCLC H69-S (Gleevec-sensitive) and H69-R (Gleevec-resistant) Cells Fig. 11. Effect of wt-FUS1 and Fus1-derived Peptide on c-Abl Activity in NSCLC cells by ELISA Fig. 12. Relative Activity of c-Abl in FUS1-Peptide treated N417 Cells Cell lysate was immunoprecipitated with c-Abl, then detected using Tyrosine Kinase Assay Kit IP Western using P6D Probed with 4G10

Active c-Abl in H1299 and A549 cells

Rat1 negative control
Rat1 SH2 positive control

20% (20,000) Rat1 SH2 cells, GFP positive, plated with 80%(80,000) Rat1 cells, GFP negative.

STI treatment started day after plating for 7 days.

Pictures taken after cells grown to confluency

Rat1 SH2 treated with 10uM STI for 7 days have holes that appear in the middle of foci

Rat1 SH2 treatment with Fus-1

- Fus-1 treated Rat1 SH2 cells form holes in foci similar to Rat1 SH2 cells treated with STI
- Untreated Rat1 SH2 cells maintain foci integrity Rat1 SH2 cells treat with 50 uM FUS1 peptide vs non-treated Rat1 SH2 cells Similar effect as STI on Rat1 SH2

Either 500 or 1000 H1299 cells were plated in soft agrose
One set treated with 10 uM STI
STI-571 treated dishes had no visible colonies post staining
By contrast untreated dishes had 83 and 39 colonies, 1000 cells and 500 cells respectively STI-571 treated dishes had no visible colonies post staining
By contrast untreated dishes had 83 and 39 colonies, 1000 cells and 500 cells respectively Effects of DOPC and DOTAP based liposomes containing Fus1 Peptide on Growth of Non small cell Lung carcinoma cells (H1299 Cells) in 48 h FIG. 24A
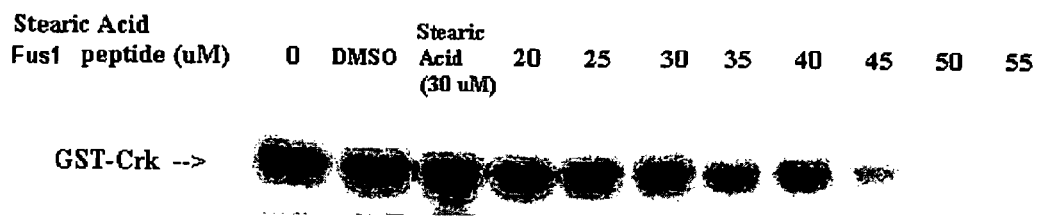
FIG. 24B Inhibition of Crk phosphorylation by stearic acid Fus1 peptide (IC50 35uM)
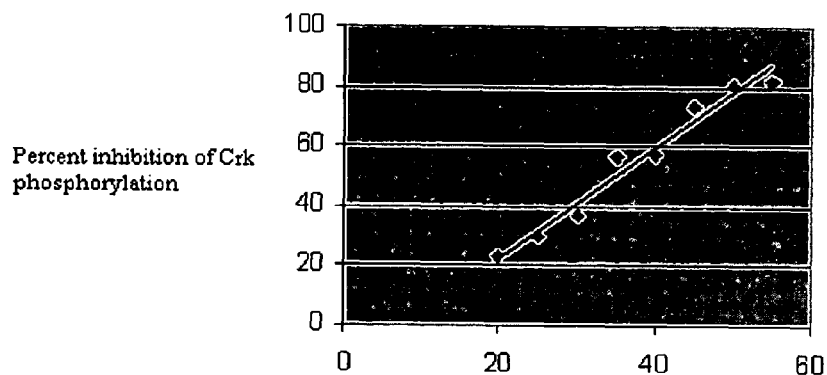
FIG. 24C
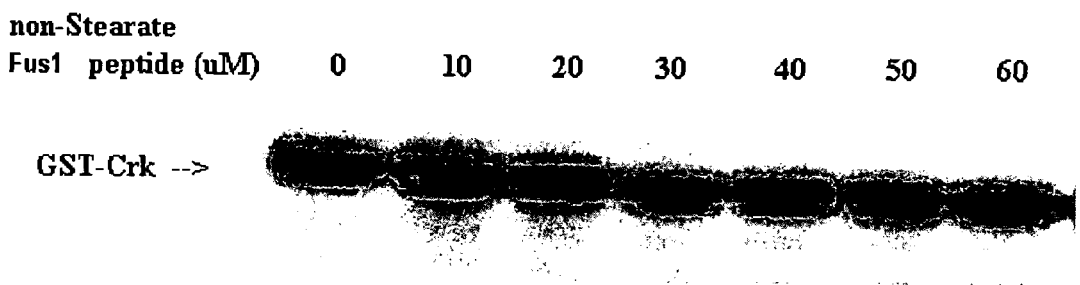
FIGS. 24A-C

Co-expression of wild type FUS1 and c-Abl leads to decrease in phosphorylation of tyrosine 412 in c-Abl Myristoylation-deficient mutant of FUS1 does not inhibit tyrosine phosphorylation of c-Abl

FIGS. 25A-C

Imatinib prevents colony formation of H1299 cells in soft agar

FIGS. 26A-C

SEQUENCE LISTING

```
<160> NUMBER OF SEQ ID NOS: 18

<210> SEQ ID NO 1
<211> LENGTH: 21
<212> TYPE: PRT
<213> ORGANISM: Artificial Sequence
<220> FEATURE:
<223> OTHER INFORMATION: Synthetic peptide

<400> SEQUENCE: 1

Lys Leu Arg Arg Val His Lys Asn Leu Ile Pro Gln Gly Ile Val Lys
1               5                   10                  15

Leu Asp His Pro Arg
            20

<210> SEQ ID NO 2
<211> LENGTH: 18
<212> TYPE: PRT
<213> ORGANISM: Artificial Sequence
<220> FEATURE:
<223> OTHER INFORMATION: Synthetic peptide

<400> SEQUENCE: 2

Lys Leu Ala Leu Lys Leu Ala Leu Lys Ala Leu Lys Ala Ala Leu Lys
1               5                   10                  15

Leu Ala

<210> SEQ ID NO 3
<211> LENGTH: 16
<212> TYPE: PRT
<213> ORGANISM: Artificial Sequence
<220> FEATURE:
<223> OTHER INFORMATION: Synthetic peptide
```

```
<400> SEQUENCE: 3

Arg Gln Ile Lys Ile Trp Phe Gln Asn Arg Arg Met Lys Trp Lys Lys
1               5                   10                  15

<210> SEQ ID NO 4
<211> LENGTH: 27
<212> TYPE: PRT
<213> ORGANISM: Artificial Sequence
<220> FEATURE:
<223> OTHER INFORMATION: Synthetic peptide

<400> SEQUENCE: 4

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 5
<211> LENGTH: 27
<212> TYPE: PRT
<213> ORGANISM: Artificial Sequence
<220> FEATURE:
<223> OTHER INFORMATION: Synthetic peptide

<400> SEQUENCE: 5

Met Gly Leu Gly Leu His Leu Leu Val Leu Ala Ala Ala Leu Gln Gly
1               5                   10                  15

Ala Trp Ser Gln Pro Lys Lys Lys Arg Lys Val
            20                  25

<210> SEQ ID NO 6
<211> LENGTH: 27
<212> TYPE: PRT
<213> ORGANISM: Artificial Sequence
<220> FEATURE:
<223> OTHER INFORMATION: Synthetic peptide

<400> SEQUENCE: 6

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
            20                  25

<210> SEQ ID NO 7
<211> LENGTH: 13
<212> TYPE: PRT
<213> ORGANISM: Artificial Sequence
<220> FEATURE:
<223> OTHER INFORMATION: Synthetic peptide

<400> SEQUENCE: 7

Gly Arg Lys Lys Arg Arg Gln Arg Arg Arg Pro Pro Gln
1               5                   10

<210> SEQ ID NO 8
<211> LENGTH: 18
<212> TYPE: PRT
<213> ORGANISM: Artificial Sequence
<220> FEATURE:
<223> OTHER INFORMATION: Synthetic peptide

<400> SEQUENCE: 8

Arg Gly Gly Arg Leu Ser Tyr Ser Arg Arg Arg Phe Ser Thr Ser Thr
1               5                   10                  15

Gly Arg
```

-continued

```
<210> SEQ ID NO 9
<211> LENGTH: 10
<212> TYPE: PRT
<213> ORGANISM: Artificial Sequence
<220> FEATURE:
<223> OTHER INFORMATION: Synthetic peptide

<400> SEQUENCE: 9

Arg Arg Leu Ser Tyr Ser Arg Arg Arg Phe
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Synthetic peptide

<400> SEQUENCE: 10

Lys Leu Ala Lys Leu Ala Lys Lys Leu Ala Lys Leu Ala Lys
1               5                   10

<210> SEQ ID NO 11
<211> LENGTH: 20
<212> TYPE: PRT
<213> ORGANISM: Artificial Sequence
<220> FEATURE:
<223> OTHER INFORMATION: Synthetic peptide

<400> SEQUENCE: 11

Lys Leu Arg Arg Val His Lys Asn Leu Ile Pro Gln Gly Ile Val Lys
1               5                   10                  15

Leu Asp His Arg
            20

<210> SEQ ID NO 12
<211> LENGTH: 110
<212> TYPE: PRT
<213> ORGANISM: Artificial Sequence
<220> FEATURE:
<223> OTHER INFORMATION: Synthetic peptide

<400> SEQUENCE: 12

Met Gly Ala Ser Gly Ser Lys Ala Arg Gly Leu Trp Pro Phe Ala Ser
1               5                   10                  15

Ala Ala Gly Gly Gly Gly Ser Glu Ala Ala Gly Ala Glu Gln Ala Leu
                20                  25                  30

Val Arg Pro Arg Gly Arg Ala Val Pro Pro Phe Val Phe Thr Arg Arg
            35                  40                  45

Gly Ser Met Phe Tyr Asp Glu Asp Gly Asp Leu Ala His Glu Phe Tyr
        50                  55                  60

Glu Glu Thr Ile Val Thr Lys Asn Gly Gln Lys Arg Ala Lys Leu Arg
65                  70                  75                  80

Arg Val His Lys Asn Leu Ile Pro Gln Gly Ile Val Lys Leu Asp His
                85                  90                  95

Pro Arg Ile His Val Asp Phe Pro Val Ile Leu Tyr Glu Val
            100                 105                 110

<210> SEQ ID NO 13
<211> LENGTH: 21
<212> TYPE: PRT
<213> ORGANISM: Artificial Sequence
<220> FEATURE:
```

<223> OTHER INFORMATION: Synthetic peptide

<400> SEQUENCE: 13

Lys Leu Arg Arg Val His Lys Asn Leu Pro Pro Gln Gly Pro Val Lys
1               5                   10                  15

Leu Asp His Pro Arg
            20

<210> SEQ ID NO 14
<211> LENGTH: 21
<212> TYPE: PRT
<213> ORGANISM: Artificial Sequence
<220> FEATURE:
<223> OTHER INFORMATION: Synthetic peptide

<400> SEQUENCE: 14

Val Leu Arg Arg Val His Val Asn Leu Pro Pro Gln Gly Pro Val Val
1               5                   10                  15

Leu Asp His Pro Arg
            20

<210> SEQ ID NO 15
<211> LENGTH: 24
<212> TYPE: PRT
<213> ORGANISM: Artificial Sequence
<220> FEATURE:
<223> OTHER INFORMATION: Synthetic peptide

<400> SEQUENCE: 15

Asp Leu Ile Glu Glu Ala Ala Ser Arg Pro Val Asp Ala Val Pro Glu
1               5                   10                  15

Gln Val Lys Ala Ala Gly Ala Tyr
            20

<210> SEQ ID NO 16
<211> LENGTH: 19
<212> TYPE: PRT
<213> ORGANISM: Artificial Sequence
<220> FEATURE:
<223> OTHER INFORMATION: Synthetic peptide

<400> SEQUENCE: 16

Glu Thr Ile Val Thr Lys Asn Gly Gln Lys Arg Ala Lys Leu Arg Arg
1               5                   10                  15

Val His Lys

<210> SEQ ID NO 17
<211> LENGTH: 19
<212> TYPE: PRT
<213> ORGANISM: Artificial Sequence
<220> FEATURE:
<223> OTHER INFORMATION: Synthetic peptide

<400> SEQUENCE: 17

Glu Thr Pro Val Thr Val Asn Gly Gln Val Arg Ala Pro Leu Arg Arg
1               5                   10                  15

Val His Val

<210> SEQ ID NO 18
<211> LENGTH: 10
<212> TYPE: PRT
<213> ORGANISM: Artificial Sequence
<220> FEATURE:
<223> OTHER INFORMATION: Synthetic peptide

```
<400> SEQUENCE: 18

Met Gly Ala Ser Gly Ser Lys Ala Arg Gly
1               5                   10
```

BIOACTIVE FUS1 PEPTIDES AND NANOPARTICLE-POLYPEPTIDE COMPLEXES

This application claims the benefit of U.S. Provisional Application Ser. No. 60/753,632 filed Dec. 22, 2005, and U.S. Provisional Application Ser. No. 60/661,680 filed Mar. 14, 2005, the entire contents and disclosures of which are specifically incorporated by reference herein without disclaimer.

The government owns rights in the present invention pursuant to grant number P50CA70907-07 from the NIH, and DAMD17002-1-0706 from the DOD.

BACKGROUND OF THE INVENTION

1. Field of the Invention

The present invention relates generally to the fields of molecular biology and cancer therapies.

2. Description of Related Art

The therapeutic use of proteins and peptides that act intracellularly holds much promise for the treatment of cancer and other diseases. However, the efficient introduction of polypeptides into cells has been difficult to achieve. Thus, new methods of introducing polypeptides into cells are needed.

Cancer is the result in the occurrence of multiple factors. Mutations may occur in proto-oncogenes that cause cellular proliferation to increase. Mutations also may occur in tumor suppressors whose normal function is to regulate cellular proliferation. Mutations in DNA repair enzymes impair the ability of the cell to repair damage before proliferating.

Tumor suppressor genes are normal genes whose absence (loss or inactivation) can lead to cancer. Tumor suppressor genes encode proteins that slow cell growth and division. Wild-type alleles of tumor suppressor genes express proteins that suppress abnormal cellular proliferation. When the gene coding for a tumor suppressor protein is mutated or deleted, the resulting mutant protein or the complete lack of tumor suppressor protein expression may fail to correctly regulate cellular proliferation, and abnormal cellular proliferation may take place, particularly if there is already existing damage to the cellular regulatory mechanism. A number of well-studied human tumors and tumor cell lines have been shown to have missing or nonfunctional tumor suppressor genes. Examples of tumor suppressor genes include, but are not limited to, the retinoblastoma susceptibility gene or RB gene, the p53 gene, the deleted in colon carcinoma (DDC) gene and the neurofibromatosis type 1 (NF-1) tumor suppressor gene (Weinberg, 1991). Loss of function or inactivation of tumor suppressor genes may play a central role in the initiation and/or progression of a significant number of human cancers.

Currently, there are few effective options for the treatment of many common cancer types. The course of treatment for a given individual depends on the diagnosis, the stage to which the disease has developed and factors such as age, sex and general health of the patient. The most conventional options of cancer treatment are surgery, radiation therapy and chemotherapy. These therapies each are accompanied with varying side effects and they have varying degrees of efficacy. Thus, there is a need to continue developing cancer therapies, including therapies based on tumor suppressor polypeptides.

SUMMARY OF THE INVENTION

In one aspect, the present invention provides a nanoparticle-polypeptide complex comprising a bioactive polypeptide in association with a nanoparticle, wherein the bioactive polypeptide is modified by the addition of a chemical moiety that facilitates cellular uptake of the protein. The polypeptide can be a protein or a peptide. In some embodiments, the amino acid sequence of the protein or peptide is derived from the amino acid sequence of a tumor suppressor gene product. Exemplary tumor suppressor proteins are those derived from the tumor suppressor genes listed in Table 4, including CACNA2D2, PL6, 101F6, NPR1.2, BLU, RASSF1, FUS1, HYAL2 and HYAL1.

In further embodiments, the peptide can comprise a predicted functional domain of the amino acid sequence of a tumor suppressor gene product, or a biologically active variant of such domain. The predicted functional domain can be identified by computer-assisted sequence analysis of tumor suppressor gene products, and can be a domain such as a myristoylation site motif, a PKA Kinase motif, an AKAP binding motif, or a PDZ Class II domain motif.

The nanoparticle can be a lipid-based nanoparticle, a superparamagnetic nanoparticle, a nanoshell, a semiconductor nanocrystal, a quantum dot, a polymer-based nanoparticle, a silicon-based nanoparticle, a silica-based nanoparticle, a metal-based nanoparticle, a fullerene or a nanotube. In particulared embodiments, the nanoparticle is a lipid-based nanoparticle or a superparamagnetic nanoparticle. Examples of lipid-based nanoparticles include liposomes and DOTAP:cholesterol vesicles.

In some embodiments, the chemical moiety is a fatty acid. Preferably, the fatty acid is a $C_4$-$C_{18}$ fatty acid. Even more preferably, the fatty acid is stearate or myristate. In other embodiments, the chemical moiety is a cell penetrating peptide, such as those derived from HIV Tat, herpes virus VP22, the *Drosophila Antennapedia* homeobox gene product, signal sequences, fusion sequences, or protegrin I.

A nanoparticle-polypeptide complex can contain a second bioactive polypeptide in association with the nanoparticle. Both polypeptides can be proteins or both can be peptides, or one can be a protein and the other a peptide. In particulared embodiments, both the first and second polypeptides are bioactive peptides, each comprising an amino acid sequence derived from a different tumor suppressor gene product. A nanoparticle-polypeptide complex can also contain three or more bioactive polypeptides, in any combination of protein and polypeptide.

Also, in some embodiments, a nanoparticle-polypeptide complex comprising a superparamagnetic nanoparticle is encapsulated within a liposome or a DOTAP:cholesterol vesicle.

In another aspect, the present invention provides an isolated peptide having anti-cancer properties, comprising the amino acid sequence KLRRVHKNLIPQGIVKLDHPR (SEQ ID NO:1) or biologically active variants thereof.

The isolated peptide preferably is 10-100 amino acid residues in length, more preferably 10-75 residues, even more preferably 10-50 residues, more preferably still 10-25 residues, still more preferably 10 residues in length. Any isolated peptide can be modified by the addition of a chemical moiety that facilitates cellular uptake of the peptide, as described herein. Also, any isolated peptide can be incorporated into any one of the nanoparticle-polypeptide complexes described herein.

The present invention also provides pharmaceutical compositions. A pharmaceutical composition can comprise any one of the nanoparticle-polypeptide complexes described herein, or any one of the peptides based on the amino acid sequence KLRRVHKNLIPQGIVKLDHPR (SEQ ID NO:1), in a pharmaceutically acceptable diluent.

The present invention further provides a method of delivering a protein to a cell. The method comprises preparing any one of the nanoparticle-polypeptide complexes described herein, and contacting the cell with the nanoparticle-polypeptide complex under conditions sufficient to permit uptake of the bioactive polypeptide by the cell. In certain embodiments, the cell is a cell in a person.

A method of treating a tumor in a subject is also provided in the present invention. The method comprises administering to the subject a therapeutically effective amount of any one of the nanoparticle-polypeptide complexes described herein, or any one of the peptides based on the amino acid sequence KLRRVHKNLIPQGIVKLDHPR (SEQ ID NO:1), wherein the polypeptide of the nanoparticle complex is based on the amino acid sequence of a tumor suppressor gene product. Treatment can further comprise administering a chemotherapeutic agent, radiation or a second bioactive polypeptide to the subject.

The present invention also provides methods of making a nanoparticle-polypeptide complex. In certain embodiments, the method comprises: a) identifying one or more functional domains in the sequence of a bioactive polypeptide, b) preparing a peptide comprising at least one of the functional domains, c) selecting a peptide having the desired biological activity, and d) preparing a nanoparticle-polypeptide complex by associating the peptide with a nanoparticle. In certain embodiments, the functional domain is identified by computer-assisted sequence analysis of tumor suppressor gene products. In certain embodiments, the method includes modifying the peptide by adding a chemical moiety that facilitates cellular uptake of the peptide.

The present invention also provides a method of inhibiting a protein tyrosine kinase. The method comprises contacting the kinase with any one of the peptides based on the amino acid sequence KLRRVHKNLIPQGIVKLDHPR (SEQ ID NO:1), described herein. In certain particulared embodiments, the kinase is EGFR, PDGFR, cKit, cAbl, or Erk.

The present invention further provides a method of inducing apotosis in a tumor cell. The method comprises contacting the tumor cell with any one of the peptides or nanoparticle-polypeptide complexes described herein that are based on the amino acid sequence KLRRVHKNLIPQGIVKLDHPR (SEQ ID NO:1).

The present invention also provides a composition for magnetic resonance imaging. The composition comprises any one of the nanoparticle-polypeptide complexes described herein where the nanoparticle is a superparamagnetic nanoparticle.

An aspect of the present invention relates to a nanoparticle-polypeptide complex, comprising a bioactive polypeptide in association with a nanoparticle, wherein the bioactive polypeptide is modified by the addition of a chemical moiety that facilitates cellular uptake of the polypeptide. The polypeptide may be a peptide. The amino acid sequence of the peptide may be derived from the amino acid sequence of a tumor suppressor gene product. In certain embodiments, the tumor suppressor gene is a gene listed in Table 4, a pro-apoptotic gene, or a cytotoxic gene. The bioactive peptide may be a FUS-1 peptide, an *Antennapedia* homeobox gene (Antp) peptide, a HIV Tat peptide, a herpes virus VP22 peptide, a model amphipathic peptide, a transportan peptide, a SV 40 T antigen peptide, or a protegrin I peptide. In certain embodiments, the bioactive peptide is a FUS-1 peptide. The FUS-1 peptide may comprise SEQ ID NO:1. In certain embodiments, the FUS-1 peptide is SEQ ID NO:1. The bioactive peptide may comprise KLALKLALKALKAALKLA (SEQ ID NO:2), RQIKIWFQNRRMKWKK (SEQ ID NO:3), GWTLNSAGYLLGKINLKALAALAKKIL (SEQ ID NO:4), MGLGLHLLVLAAALQGAWSQPKKKRKV (SEQ ID NO:5), GALFLGWLGAAGSTMGAWSQP-KKKRKV (SEQ ID NO:6), GRKKRRQRRRPPQ (SEQ ID NO:7), RGGRLSYSRRRFSTSTGR (SEQ ID NO:8) or RRLSYSRRRF (SEQ ID NO:9). The bioactive peptide may comprise KLALKLALKALKAALKLA (SEQ ID NO:2).

The peptide may comprise a functional domain of the amino acid sequence of a tumor suppressor gene product. The peptide comprises a predicted functional domain of the amino acid sequence of a tumor suppressor gene product. The predicted functional domain is identified by computer-assisted sequence analysis of the amino acid sequence of the tumor suppressor gene product. The polypeptide may be a protein. The amino acid sequence of the protein may be derived from the amino acid sequence of a tumor suppressor gene product. The tumor suppressor gene may be a gene listed in Table 4. In certain embodiments, the tumor suppressor gene is FUS-1.

The nanoparticle may be a lipid-based nanoparticle, a superparamagnetic nanoparticle, a nanoshell, a semiconductor nanocrystal, a quantum dot, a polymer-based nanoparticle, a silicon-based nanoparticle, a silica-based nanoparticle, a metal-based nanoparticle, a fullerene or a nanotube. The nanoparticle may be a lipid-based nanoparticle. The lipid-based nanoparticle may be a liposome, a neutral liposome, a DOPC liposome or a DOTAP:cholesterol vesicle. The liposome may be a DOPC liposome. In certain embodiments, the nanoparticle is a superparamagnetic nanoparticle. In certain embodiments, the nanoparticle is a superparamagnetic nanoparticle, and the nanoparticle-polypeptide complex is within a liposome or a DOTAP:cholesterol vesicle. The liposome may be a DOPC liposome. The chemical moiety may be a fatty acid (e.g., a $C_4$-$C_{18}$ fatty acid, stearate or myristate). The chemical moiety may be a cell penetrating peptide. The cell penetrating peptide may be derived from HIV Tat, herpes virus VP22, or the *Drosophila Antennapedia* homeobox gene product.

In certain embodiments the nanoparticle-polypeptide complex further comprises a second bioactive polypeptide in association with the nanoparticle. The first and second bioactive polypeptides may be bioactive peptides, each comprising an amino acid sequence derived from a different tumor suppressor gene product. The nanoparticle-polypeptide complex may further comprise a targeting moiety that targets the nanoparticle-polypeptide complex to a tissue or cell.

Another aspect of the present invention relates to a nanoparticle-polypeptide complex, comprising a bioactive polypeptide in association with a nanoparticle, wherein the bioactive polypeptide is modified by the addition of a stearate moiety, and the nanoparticle is a DOTAP:cholesterol vesicle, a DOPC liposome or a superparamagnetic nanoparticle.

A further aspect of the present invention relates to an isolated peptide comprising the amino acid sequence KLRRVH-KNLIPQGIVKLDHPR (SEQ ID NO:1) or a biologically active variant thereof. The peptide may be from 10 to 100, 10 to 75, 10 to 50, 10 to 25 or 10 amino acid residues in length. The peptide may be modified by the addition of a chemical moiety that facilitates cellular uptake of the peptide. The chemical moiety may be a fatty acid (e.g., a $C_4$-$C_{18}$ fatty acid, stearate or myristate) or a cell penetrating peptide. The cell penetrating peptide may be derived from HIV Tat, herpes virus VP22, or the *Drosophila Antennapedia* homeobox gene product.

Another aspect of the present invention relates to a nanoparticle-polypeptide complex, comprising a bioactive peptide of the present invention and a nanoparticle. The nanoparticle may be a lipid-based nanoparticle (e.g., a liposome or a DOT- AP:cholesterol vesicle), a superparamagnetic nanoparticle, a nanoshell, a semiconductor nanocrystal, a quantum dot, a polymer-based nanoparticle, a silicon-based nanoparticle, a silica-based nanoparticle, a metal-based nanoparticle, a fullerene or a nanotube. In certain embodiments, the nanoparticle is a superparamagnetic nanoparticle, and the nanoparticle-polypeptide complex is within a liposome or a DOTAP:cholesterol vesicle.

Another aspect of the present invention relates to a nanoparticle-polypeptide complex, comprising a peptide of amino acid sequence KLRRVHKNLIPQGIVKLDHPR (SEQ ID NO:1), in association with a nanoparticle, wherein the peptide is modified by the addition of a stearate moiety, and the nanoparticle is a liposome, a DOTAP:cholesterol vesicle, a DOPC liposome or a superparamagnetic nanoparticle.

Another aspect of the present invention relates to a method of treating a disease comprising administering to a subject a pharmaceutical composition comprising a peptides or nanoparticle-polypeptide complex of the present invention, in a pharmaceutically acceptable diluent. The disease may be cancer (e.g., a lung cancer, a NSCLC). The method may further comprise administering a chemotherapeutic agent (e.g., imatinib) to the subject. The method may further comprise administering radiation or a second bioactive polypeptide to the subject.

A further aspect of the present invention relates to a method of delivering a polypeptide to a cell, comprising preparing a nanoparticle-polypeptide complex of the present invention and contacting the cell with the nanoparticle-polypeptide complex under conditions sufficient to permit uptake of the bioactive polypeptide by the cell.

Another aspect of the present invention relates to a method of treating a tumor in a subject, comprising administering to the subject a therapeutically effective amount of a peptide or nanoparticle-polypeptide complex of the present invention, wherein the polypeptide of the nanoparticle complex is based on the amino acid sequence of a tumor suppressor gene product. The administration may be intraperitoneal injection. The tumor may be a gastrointestinal tumor.

A further aspect of the present invention relates to a method of making a nanoparticle-polypeptide complex, comprising identifying one or more functional domains in the sequence of a bioactive polypeptide, preparing a peptide comprising at least one of the functional domains, selecting a peptide having the desired biological activity, and preparing a nanoparticle-polypeptide complex by associating the peptide with a nanoparticle. The identifying may comprise using computer assisted structural analysis. The computer assisted structural analysis may result in the identification of a putative protein kinase interacting site, a putative myristoylation site, a PDZ Class II domain motif or an A kinase anchoring protein (AKAP) motif. The method may further comprise modifying the peptide by adding a chemical moiety that facilitates cellular uptake of the peptide. The functional domain may be a predicted functional domain of the amino acid sequence of a tumor suppressor gene.

Another aspect of the present invention relates to a method of inhibiting a protein tyrosine kinase, comprising contacting the kinase (e.g., EGFR, PDGFR, cKit, cAbl, or Erk) with a peptide of the present invention.

A further aspect of the present invention relates to a method of inducing apoptosis in a tumor cell, comprising contacting the tumor cell with a peptide of the present invention.

Another aspect of the present invention relates to a method of inducing apoptosis in a tumor cell, comprising contacting the tumor cell with a nanoparticle-polypeptide complex of the present invention.

Another aspect of the present invention relates to a composition for magnetic resonance imaging, comprising a nanoparticle-polypeptide complex of the present invention, wherein the nanoparticle is a superparamagnetic nanoparticle.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 24A-C. Concentration-dependent inhibition of the Abl tyrosine kinase by the stearic Fus1 peptide. FIG. 24A, Inhibition of commercial Abl tyrosine kinase by a stearic acid modified Fus1 peptide. FIG. 24B, Linear inhibition of the Abl tyrosine kinase by stearic acid Fus1 peptide. FIG. 24C, Non-stearic acid modified Fus1 peptide does not inhibit Abl tyrosine kinase activity.

FIG. 26A, 1000 H1299 cells were plated in 0.35% soft agar either containing 0 uM, 1 uM, or 5 uM imatinib. Cells were grown for 18 days changing the media every two days containing the respective concentrations of imatinib. FIG. 26B, Dose dependent inhibition of H1299 colony formation in soft agar by imatinib. FIG. 26C, 1000 H1299 cells were plated in 0.35% soft agar either containing 10 uM imatinib or untreated. Cells were grown for 18 days changing the media every two days containing the respective concentrations of imatinib.

DESCRIPTION OF ILLUSTRATIVE EMBODIMENTS

I. Nanoparticle-Polypeptide Complexes

Figure 1:
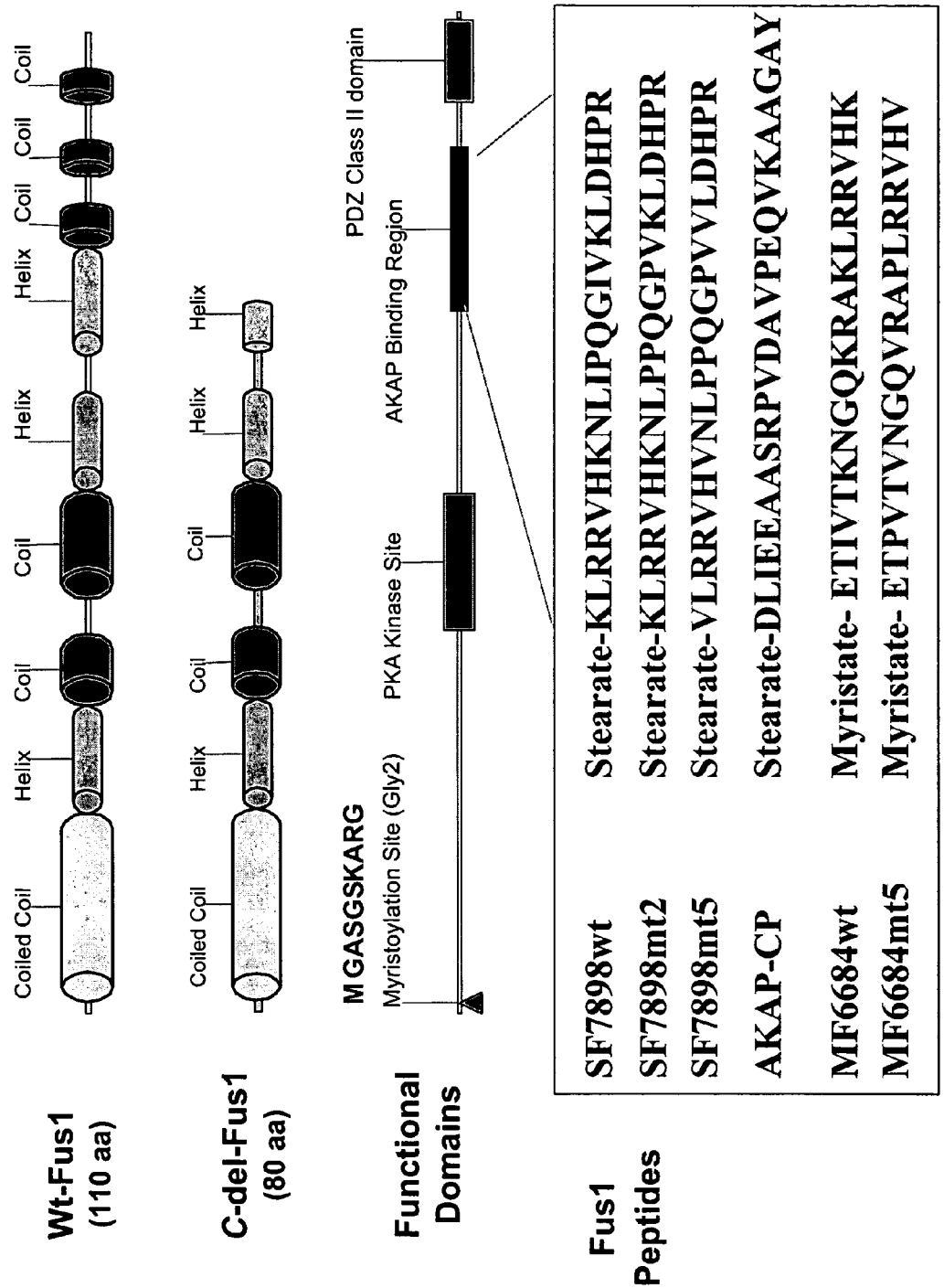
FIG. 1: A schematic analysis of Fus1 protein structure and provides a list of Fus1 peptides used in the Examples. AKAP-CP is the control peptide.

The present invention provides compositions and methods for delivering a polypeptide to a cell. The compositions and methods have general utility for any bioactive protein or peptide, and provide therapeutic reagents for the treatment of many types of disease. In particular, the present invention provides nanoparticle-polypeptide complexes and methods of using such complexes for delivering a polypeptide to the inside of a cell. The complexes comprise a bioactive polypeptide in association with a nanoparticle. As used herein, "association" means a physical association, a chemical association or both. For example, an association can involve a covalent bond, a hydrophobic interaction, encapsulation, surface adsorption, or the like.

Proteins and peptides that act inside the cell have substantial value as therapeutic drugs. For metabolic diseases that result from the loss of an enzyme, the intracellular delivery of a protein or peptide that supplies the critical enzyme activity can be used to treat a disease. The treatment of cancer can also benefit from the introduction of protein or peptide drugs into tumor cells by, for example, introducing a protein and/or peptide that inhibits an oncogene, promotes apoptosis, prevents angiogenesis and/or restores or provides the function of a tumor suppressor gene product. By providing compositions and methods for delivering polypeptides intracellularly, the present invention provides effective therapeutic agents for the treatment of diverse diseases.

The present invention can provide effective therapeutic agents for the treatment of diseases and disorders involving the loss of protein function or activity, or the inappropriate expression of protein activity. For example, metabolic diseases comprise more than 1,000 inherited disorders in which there is a genetic fault in metabolism. Metabolism involves the formation of essential components of the body (anabolism) or the breakdown of essential body components (catabolism). Each step of a metabolic pathway is controlled by an enzyme. The genetic defect results in the reduction or loss of enzyme activity. Metabolic disorders can cause disease in any system and cell of the body, although the severity of disease can be varied and unpredictable. While some defects cause few problems, others lead to severe illness and death. The present invention can provide therapeutic agents in the form of nanoparticle-polypeptide complexes that supply affected cells with the necessary enzyme activity, thereby reducing or eliminating the disease state.

Alternatively, for diseases involving inappropriate expression of protein activity, the use of inhibitors of protein activity can provide substantial benefits. For example, many disease states are associated with abnormal cellular responses triggered by protein kinase-mediated events. These diseases include such diseases as autoimmune diseases, inflammatory diseases, metabolic diseases, neurological and neurodegenerative diseases, cancer, cardiovascular diseases, allergies and asthma, Alzheimer's disease and hormone-related diseases. Protein kinase inhibitors that disrupt enzyme activity or interfere with the intracellular localization of protein kinases are expected to be valuable therapeutic agents for the treatment of such diseases. Indeed, peptides that inhibit the catalytic activity of protein kinases (Hvalby et al., 1994) and peptides that disrupt subcellular targeting of protein kinases (Colledge and Scott, 1999) have been identified. The present invention provides compositions and methods that can be used to deliver these and other protein kinase inhibiting polypeptides to cells. Thus, the present invention provides a general way of treating a multitude of diseases.

Polypeptides typically have difficulty crossing cellular membranes. Proteins and peptides typically have both charged and uncharged amino acid residues. The charged residues can hinder membrane binding and membrane transport into cells. The present invention overcomes this difficulty by, for example, attaching a chemical moiety to the bioactive polypeptide to facilitate cellular uptake. In certain embodiments of the present invention, this is accomplished by fusing the bioactive polypeptide to a peptide that promotes uptake by the cell.

For example, cell-penetrating peptides (or "protein transduction domains") have been identified from the third helix of the *Drosophila Antennapedia* homeobox gene (Antp), the HIV Tat, and the herpes virus VP22, all of which contain positively charged domains enriched for arginine and lysine residues (Schwarze et al., 2000; Schwarze et al., 1999). Also, hydrophobic peptides derived from signal sequences have been identified as cell-penetrating peptides. (Rojas et al., 1996; Rojas et al., 1998; Du et al., 1998). Coupling these peptides to marker proteins such as β-galactosidase has been shown to confer efficient internalization of the marker protein into cells, and chimeric, in-frame fusion proteins containing these peptides have been used to deliver proteins to a wide spectrum of cell types both in vitro and in vivo (Drin et al., 2002). Fusion of these cell penetrating peptides to the bioactive polypeptides in accordance with the present invention can enhance cellular uptake of the polypeptides.

In other embodiments, cellular uptake is facilitated by the attachment of a lipid, such as stearate or myristilate, to the polypeptide. Lipidation has been shown to enhance the passage of peptides into cells (REF). The attachment of a lipid moiety is another way that the present invention increases polypeptide uptake by the cell. Cellular uptake is further discussed below.

By enhancing the uptake of a bioactive polypeptide, the present invention can reduce the amount of protein or peptide required for treatment. This in turn can significantly reduce the cost of treatment and increase the supply of therapeutic agent. Lower dosages can also minimize the potential immunogenicity of peptides and limit toxic side effects. As such, the compositions and methods of the present invention provide significant benefits for therapeutic treatments.

In accordance with the present invention, a bioactive polypeptide may be associated with a nanoparticle to form nanoparticle-polypeptide complex. In some embodiments, the nanoparticle is a liposomes or other lipid-based nanoparticle such as a lipid-based vesicle (e.g., a DOTAP:cholesterol vesicle). As used in cancer therapy, liposomes take advantage of the increased fenestrations in the cancer neovasculature to enhance liposome concentration at tumor sites. In other embodiments, the nanoparticle is an iron-oxide based superparamagnetic nanoparticles. Superparamagnetic nanoparticles ranging in diameter from about 10 to 100 nm are small enough to avoid sequestering by the spleen, but large enough to avoid clearance by the liver. Particles this size can penetrate very small capillaries and can be effectively distributed in body tissues. Superparamagnetic nanoparticles-polypeptide complexes can be used as MRI contrast agents to identify and follow those cells that take up the bioactive polypeptide. In certain embodiments, the nanoparticle is a semiconductor nanocrystal or a semiconductor quantum dot, both of which can be used in optical imaging. In further embodiments, the nanoparticle can be a nanoshell, which comprises a gold layer over a core of silica. One advantage of nanoshells is that polypeptides can be conjugated to the gold layer using standard chemistry. In other embodiments, the nanoparticle can be a fullerene or a nanotube (Gupta et al., 2005).

Peptides are rapidly removed from the circulation by the kidney and are sensitive to degradation by proteases in serum. By associating a bioactive peptide with a nanoparticle, the nanoparticle-polypeptide complexes of the present invention can both protect against degradation and reduce clearance by the kidney. This increases the serum half-life of polypeptides, thereby reducing the polypeptide dose need for effective therapy. Again, this decreases the costs of treatment, and minimizes immunological problems and toxic reactions of therapy.

In accordance with the present invention, nanoparticle-polypeptide complexes can be targeted to specific tissues and cells. This can be accomplished by conjugating a cell targeting moiety to the nanoparticle. The targeting moiety can be, but is not limited to, a protein, peptide, lipid, steroid, sugar, carbohydrate or synthetic compound. Cell targeting moieties such as ligands recognize and bind to their cognate receptors on the surface of cells. Similarly, antibody can act as cell targeting moieties by recognizing their cognate antigens on the cell surface. By providing targeted nanoparticle-polypeptide complexes, the present invention can enhance the specificity of disease treatment and increase the amount of therapeutic agent entering a targeted cell.

The association of polypeptides with nanoparticles in accordance with the present invention provides for highly efficient, targeted delivery of polypeptides, strong cellular uptake of polypeptides, sensitive molecular imaging of treated cells, reduced dosage and cost of treatment, and minimization of immunological problems and toxic effects of therapy. The nanoparticle-polypeptide complexes of the present invention provide compositions and methods for efficiently and effectively treating a variety of diseases.

With regard to cancer, the present invention provides compositions and methods for cancer treatment.

It is now well established that a variety of cancers are caused, at least in part, by genetic abnormalities that result in either the over expression of one or more genes, or the expression of an abnormal or mutant gene or genes. For example, in many cases, the expression of oncogenes is known to result in the development of cancer. "Oncogenes" are genetically altered genes whose mutated expression product somehow disrupts normal cellular function or control (Spandidos et al., 1989). Most oncogenes studied to date have been found to be "activated" as the result of a mutation in the coding region of a normal cellular gene, i.e., a "proto-oncogene", that results in amino acid substitutions in the expressed protein product. This altered expression product exhibits an abnormal biological function that takes part in the neoplastic process (Travali et al., 1990). A number of oncogenes and oncogene families, including ras, myc, neu, raf, erb, src, fms, jun and abl, have now been identified and characterized to varying degrees (Travali et al., 1990).

The ras gene family of cellular oncogenes encodes small GTP-binding proteins. ras genes have been found mutated in a wide variety of human tumors. The ras protein (Ras) is a central component in intracellular signaling pathways involved in the transduction of stimuli that induce growth and/or differentiation, acting via the serine/threonine protein kinase encoded by the raf gene. myc is a cellular oncogene that encodes a transcription factor, forming a DNA-binding hetero-oligomer with the transcription factor Max. Src and fms are tyrosine protein kinases as is abl. Proteins and peptides that block or interfere with the activity of oncogenes can act as anti-cancer agents and are embodied in the present invention.

As noted above, tumor suppressor genes are normal genes whose absence (loss or inactivation) can lead to cancer. A tumor suppressor gene may encode a proteins that slows cell growth and division. Their loss can thus lead to unregulated cell growth and cancer. Therefore, proteins and peptides that reactivate a tumor suppressor gene product, or supply the activity associated with the tumor suppressor gene product, may be used as anti-tumor therapeutics. Tumor suppressor gene proteins and peptides may be used with, and are encompassed by, the present invention.

Proteins or peptides that stimulate apoptosis can act as anti-cancer agents. Apoptosis is the programmed death of cells. Apoptosis is an essential process for normal embryonic development, maintaining homeostasis in adult tissues, and suppressing carcinogenesis (Kerr et al., 1972). A polypeptide that stimulates apoptosis in a cancer cell can provide anti-cancer activity, and is a part of the present invention.

Angiogenesis is essential for tumor progression (Folkman and Shing, 1992; Fidler and Ellis, 1994; Folkman, 1995; Hanahan and Folkman, 1996) Angiogenesis is the formation of new capillaries from pre-existing vessels. Although tumors of 1-2 mm in diameter can receive all nutrients by diffusion, further growth depends on the development of an adequate blood supply through angiogenesis. Thus, inhibitors of angiogenesis can act as anti-tumor agents. Polypeptides that act as angiogenesis inhibitors are encompassed by the present invention.

In particular embodiments, the present invention provides peptides and nanoparticle-polypeptide complexes for the treatment of cancer. Anti-cancer peptides can be identified empirically, or by theoretical methods. A non-limiting example of empirically identifying an anti-cancer peptide is provided for the tumor suppressor gene p53. The p53 gene encodes a transcription factor. Mutations in the p53 gene that abolish activity result in cancer. It has been shown that peptides containing amino acid sequences from the carboxy terminus of the p53 transcription factor can reactivate certain p53 mutants and re-establish control of cell growth. Thus, nanoparticle-polypeptide complexes formed with p53 carboxy-terminal peptides provide anti-cancer agents for the treatment of certain p53 tumors.

Anti-cancer peptides can also be identified experimentally by screening combinatorial peptide libraries. As a non-limiting example, peptide-phage libraries or peptide libraries based on combinatorial chemistry can be screened for peptides that inhibit the activity of an oncogene protein. Other anti-cancer peptides can be based on experimentally identified apoptosis peptides, such as the peptide KLAK-LAKKLAKLAK (SEQ ID NO:10) and other apoptotic peptides (see, e.g., Ellerby et al., 1999). The use of novel or previously identified anti-cancer peptides in nanoparticle-polypeptide complexes shows the general applicability of the present invention for the treatment of cancer.

Alternatively, potential anti-cancer peptides can be identified by analyzing the amino acid sequence of a tumor suppressor gene product for predicted functional domains. Peptides containing predicted functional domains can then be assayed for anti-cancer activity by means of an appropriate assay well known in the art. An example of this approach is described in the Examples. The inventors performed an amino acid sequence analysis of the FUS1 gene product and identified a predicted "A kinase anchoring protein" (AKAP) motif. A peptide containing this functional motif was tested for its ability to inhibit various tyrosine kinases and to block foci formation. Positive activity establishes that this protein as an anti-cancer agent. In accordance with the present invention, nanoparticle-Fus1 peptide complexes are provided as therapeutic agents for the treatment of cancer.

As this example demonstrates, the present invention provides a method of identifying anti-cancer peptides and proteins based on predicted functional domains of tumor suppressor gene products. This method is a powerful way to quickly obtain anti-cancer polypeptides and nanoparticle-polypeptide complexes for use as therapeutic agents.

Once an anti-cancer protein or peptide is identified, variants of these polypeptides can be produced based on the amino acid sequence of the protein or peptide. Both these polypeptides and their variants may be used with, and are encompassed by, the present invention.

The present invention can be used deliver bioactive polypeptides to cells. For example, the present invention provides methods and compositions for treating cancer. The cancer can be any of the following types of cancer: melanoma, non-small cell lung, small-cell lung, lung, hepatocarcinoma, retinoblastoma, astrocytoma, glioblastoma, gum, tongue, leukemia, neuroblastoma, head, neck, breast, pancreatic, prostate, renal, bone, testicular, ovarian, mesothelioma, cervical, gastrointestinal, lymphoma, brain, colon, or bladder. In certain embodiments, the cancer involves epithelial cancer cells. In specific embodiments, the cancer is lung cancer.

A. Polypeptides

As used herein, the term "polypeptide" means either a protein or a peptide. A peptide is considered to have from 3 to 100 amino acids. A protein is considered to have more than 100 amino acids.

In certain embodiments the size of the polypeptide molecule may comprise, but is not limited to, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1100, 1200, 1300, 1400, 1500, 1750, 2000, 2250, 2500 or greater amino molecule residues, and any range derivable therein.

In certain embodiments, a bioactive polypeptide of the present invention may comprise from 3 to 2500, more preferably from 3 to 1000, more preferably from 3 to 500, more preferably from 5 to 250, more preferably from 7 to 250, more preferably from 10 to 100, more preferably from 10 to 50, more preferably from 10 to 40, most preferably from 10 to 35 amino molecule residues.

As used herein, an "amino molecule" refers to any amino acid, amino acid derivative or amino acid mimic as would be known to one of ordinary skill in the art. In certain embodiments, the residues of the polypeptide are sequential, without any non-amino molecule interrupting the sequence of amino molecule residues. In other embodiments, the sequence may comprise one or more non-amino molecule moieties. In particular embodiments, the sequence of residues of the polypeptide may be interrupted by one or more non-amino molecule moieties.

Accordingly, the term "polypeptide" encompasses amino molecule sequences comprising at least one of the 20 common amino acids in naturally synthesized proteins, or at least one modified or unusual amino acid, including but not limited to those shown on Table 1 below.

TABLE 1

Modified and Unusual Amino Acids

| bbr. | Amino Acid | Abbr. | Amino Acid |
|---|---|---|---|
| ad | 2-Aminoadipic acid | EtAsn | N-Ethylasparagine |
| aad | 3-Aminoadipic acid | Hyl | Hydroxylysine |
| ala | β-alanine, β-Amino-propionic acid | AHyl | allo-Hydroxylysine |
| bu | 2-Aminobutyric acid | 3Hyp | 3-Hydroxyproline |
| Abu | 4-Aminobutyric acid, piperidinic acid | 4Hyp | 4-Hydroxyproline |
| cp | 6-Aminocaproic acid | Ide | Isodesmosine |
| he | 2-Aminoheptanoic acid | AIle | allo-Isoleucine |
| ib | 2-Aminoisobutyric acid | MeGly | N-Methylglycine, sarcosine |
| aib | 3-Aminoisobutyric acid | MeIle | N-Methylisoleucine |
| pm | 2-Aminopimelic acid | MeLys | 6-N-Methyllysine |
| bu | 2,4-Diaminobutyric acid | MeVal | N-Methylvaline |
| es | Desmosine | Nva | Norvaline |
| pm | 2,2'-Diaminopimelic acid | Nle | Norleucine |
| pr | 2,3-Diaminopropionic acid | Orn | Ornithine |
| tGly | N-Ethylglycine | | |

In certain embodiments, the nanoparticle-polypeptide complex comprises a biocompatible polypeptide. As used herein, the term "biocompatible" refers to a substance which produces little or no significant untoward effects when applied to, or administered to, a given organism according to the methods and amounts described herein. Such untoward or undesirable effects are those such as significant toxicity or adverse immunological reactions. In particulared embodiments, biocompatible polypeptides or nanoparticle-polypeptide complexes will generally be mammalian proteins or peptides or synthetic proteins or peptides each essentially free from toxins, pathogens and harmful immunogens.

Proteins and peptides may be made by any technique known to those of skill in the art, including the expression of proteins and peptides through standard molecular biological techniques, the isolation of proteins and peptides from natural sources, or the chemical synthesis of proteins and peptides. The nucleotide and polypeptide sequences for various genes have been previously disclosed, and may be found at computerized databases known to those of ordinary skill in the art.

One such database is the National Center for Biotechnology Information's Genbank and GenPept databases (found on the World Wide Web at (ncbi.nlm.nih.gov). The coding regions for these known genes may be amplified and/or expressed using the techniques disclosed herein or as would be know to those of ordinary skill in the art. Alternatively, various commercial preparations of proteins and peptides are known to those of skill in the art.

In certain embodiments a polypeptide may be isolated or purified. Generally, "isolated" or "purified" will refer to a specific polypeptide composition that has been subjected to fractionation to remove various other polypeptides, and which composition substantially retains its activity, as may be assessed, for example, by the protein assays, as would be known to one of ordinary skill in the art for the specific or desired protein or peptide.

In certain embodiments, a therapeutically effective amount of a polypeptide or nanoparticle-polypeptide complex is used to treat a tumor in a subject. A therapeutically effective amount is an amount that will result in an improvement or a desired change in condition for which an active ingredient is administered, when the ingredient is administered once or over a period of time. As is known, the amount will vary depending on such particulars as the type of condition being treated, the specific active ingredient, the severity of the condition, and the characteristics of the patient.

1. Variants

The terms "polypeptide", "protein" and "peptide" also encompass amino acid sequence variants of a protein or peptide. Amino acid sequence variants of the polypeptides of the present invention can be substitutional, insertional or deletion variants. Deletion variants lack one or more residues of the native protein that are not essential for function or immunogenic activity, as exemplified by variants of integral membrane proteins that lack a transmembrane sequence. Another common type of deletion variant is one lacking secretory signal sequences or signal sequences directing a protein to bind to a particular part of a cell. Insertional mutants typically involve the addition of material at a non-terminal point in the polypeptide. This may include the insertion of an immunoreactive epitope or simply a single residue. Terminal additions, called fusion proteins, are discussed below.

Substitutional variants typically contain the exchange of one amino acid for another at one or more sites within the polypeptide, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The term "biologically functional equivalent" is well understood in the art and is further defined in detail herein. Accordingly, sequences that have between about 70% and about 80%; or more preferably, between about 81% and about 90%; or even more preferably, between about 91% and about 99%; of amino acids that are identical or functionally equivalent to the amino acids of a bioactive polypetide are within the scope of the invention provided the biological activity of the polypeptide is maintained.

The term "functionally equivalent codon" is used herein to refer to codons that encode the same amino acid, such as the six codons for arginine or serine, and also refers to codons that encode biologically equivalent amino acids (see Table 2, below).

TABLE II

Codon Table

| Amino Acids | | | Codons | | | |
|---|---|---|---|---|---|---|
| Alanine | Ala | A | GCA | GCC | GCG | GCU |
| Cysteine | Cys | C | UGC | UGU | | |
| Aspartic acid | Asp | D | GAC | GAU | | |
| Glutamic acid | Glu | E | GAA | GAG | | |
| Phenylalanine | Phe | F | UUC | UUU | | |
| Glycine | Gly | G | GGA | GGC | GGG | GGU |
| Histidine | His | H | CAC | CAU | | |
| Isoleucine | Ile | I | AUA | AUC | AUU | |
| Lysine | Lys | K | AAA | AAG | | |
| Leucine | Leu | L | UUA | UUG | CUA | CUC | CUG |
| | | | CUU | | | |
| Methionine | Met | M | AUG | | | |
| Asparagine | Asn | N | AAC | AAU | | |
| Proline | Pro | P | CCA | CCC | CCG | CCU |
| Glutamine | Gln | Q | CAA | CAG | | |
| Arginine | Arg | R | AGA | AGG | CGA | CGC | CGG |
| | | | CGU | | | |
| Serine | Ser | S | AGC | AGU | UCA | UCC | UCG |
| | | | UCU | | | |
| Threonine | Thr | T | ACA | ACC | ACG | ACU |
| Valine | Val | V | GUA | GUC | GUG | GUU |
| Tryptophan | Trp | W | UGG | | | |
| Tyrosine | Tyr | Y | UAC | UAU | | |

It also will be understood that amino acid sequences may include additional residues, such as additional N- or C-terminal amino acids, and yet still be essentially as set forth in one of the sequences disclosed herein, so long as the sequence meets the criteria set forth above, including the maintenance of biological activity.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence and nevertheless produce a protein with like properties. It is thus contemplated by the inventors that various changes may be made in the amino acid sequences of the polypeptides described herein without appreciable loss of their biological utility or activity, as discussed below. Table 2 shows the codons that encode particular amino acids.

In making such changes, the hydropathic index of amino acids may be considered. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine *−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still produce a biologically equivalent and immunologically equivalent polypeptide. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine-and isoleucine.

Another embodiment for the preparation of polypeptides according to the invention is the use of peptide mimetics. Mimetics are peptide-containing molecules that mimic elements of protein secondary structure. See e.g., Johnson et al., 1993. The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outline above, to engineer second generation molecules having many of the natural properties of the polypeptides described herein, but with altered and even improved characteristics.

In another embodiment, peptides contain D-amino acids rather than the L-amino acids typically found in biological proteins. The D-amino acids can be substituted during chemical synthesis of the peptides. Further, reverse-D peptides are contemplated. Reverse-D peptides retain the same tertiary conformation, and therefore the same activity, as the L-amino acid peptides, but are more stable to enzymatic degradation in vitro and in vivo, and thus have greater therapeutic efficacy than the original peptide Brady and Dodson, 1994; Jameson et al., 1994).

Proteins and peptides can be conjugated with fluorescent, chemiluminescent or other types of tags or labels for detection, as is well known in the art.

2. Fusion Proteins

A specialized kind of insertional variant is a fusion protein. This molecule generally has all or a substantial portion of the native molecule, linked at the N- or C-terminus, to all or a portion of a second polypeptide. For example, fusions can employ leader sequences from other species to permit the recombinant expression of a protein in a heterologous host. Another useful fusion includes the addition of an immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes such as a hydrolase, glycosylation domains, cellular targeting signals or transmembrane regions. Particularly preferred fusions involve linking a cell-penetrating peptide to a polypeptide to promote uptake of the polypeptide by the cell.

For example, peptides from the HIV Tat polypeptide, the third helix of the *Drosophila Antennapedia* homeobox gene (Antp), the Influnza virus hemagglutinin and/or the herpes virus VP22 polypeptide may be used with the present invention to create fusion proteins. These proteins contain positively charged domains enriched for arginine and lysine residues, and hydrophobic peptides derived from signal sequences and fusion sequences have been identified as cell-penetrating peptides. These peptides may be used to deliver proteins to a wide spectrum of cell types both in vitro and in vivo. In the present invention, these peptides can be used to promote the cellular uptake of bioactive proteins and peptides.

3. Polypeptide Purification

It may be desirable to purify or isolate a the polypeptides considered herein. Protein purification techniques are well known to those of skill in the art. These techniques involve, at one level, the crude fractionation of the cellular milieu to polypeptide and non-polypeptide fractions. Having separated the polypeptide from other proteins and peptides, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Particularly efficient methods of purifying peptides are fast protein liquid chromatography and HPLC.

Where the term "substantially purified" or "substantially isolated" is used, this designation will refer to a composition in which the protein or peptide forms the major component of the composition, such as constituting about 50%, about 60%, about 70%, about 80%, about 90%, about 95% or more of the proteins in the composition.

4. Facilitating Cellular Uptake

In some embodiments, the polypeptide can be modified by the addition of a chemical moiety that facilitates cellular uptake of the polypeptide. Examples of moieties for enhancing cellular uptake include but are not limited to: a hydrophobic group (e.g., a lipid or fatty acid), a cell-penetrating peptide (see, e.g., U.S. Pat. No. 6,610,657; Drin, et al., 2002), and certain metal chelates.

A fatty acid generally is a molecule comprising a carbon chain with an acidic moiety (e.g., carboxylic acid) at an end of the chain. The carbon chain may of a fatty acid may be of any length, however, it is preferred that the length of the carbon chain be of from at least 2, 3, 4, 5, 6, 7, 8, 9, 10, 11, 12, 13, 14, 15, 16, 17, 18, 19, 20 or more carbon atoms, and any range derivable therein. In certain embodiments, the length of the carbon chain is from 4 to 18 carbon atoms in the chain portion of the fatty acid. In certain embodiments the fatty acid carbon chain may comprise an odd number of carbon atoms, however, an even number of carbon atoms in the chain may be preferred in certain embodiments. A fatty acid comprising only single bonds in its carbon chain is called saturated, while a fatty acid comprising at least one double bond in its chain is called unsaturated. The fatty acid may be branched, though in preferable embodiments of the present invention, it is unbranched. Specific fatty acids include, but are not limited to, linoleic acid, oleic acid, palmitic acid, linolenic acid, stearic acid, lauric acid, myristic acid, arachidic acid, palmitoleic acid, arachidonic acid.

As described above, various cell-penetrating peptides have been identified. Table III lists some of these peptides and their amino acid sequences. In certain embodiments, a cell-penetrating has multiple positive charges and ranges in size from 10-27 amino acid residues. Any of these peptides is contemplated to be applicable to the present invention.

TABLE III

| PEPTIDE NAME | SEQUENCE |
| --- | --- |
| MAP (model amphipathic peptide) | KLALKLALKALKAALKLA (SEQ ID NO: 2) |
| pAntp$_{43-58}$ (or penetratin) | RQIKIWFQNRRMKWKK (SEQ ID NO: 3) |
| Transportan | GWTLNSAGYLLGKINLKALAALAKKIL (SEQ ID NO: 4) |
| SBP (signal sequence based peptide from SV40 T antigen) | MGLGLHLLVLAAALQGAWSQPKKKRKV (SEQ ID NO: 5) |
| FSB (fusion sequence based peptide from SV40 T antigen) | GALFLGWLGAAGSTMGAWSQPKKKRKV (SEQ ID NO: 6) |
| Tat (HIV Tat peptide) | GRKKRRQRRRPPQ (SEQ ID NO: 7) |
| SynB1 (from Protegrin I) | RGGRLSYSRRRFSTSTGR (SEQ ID NO: 8) |
| SynB3 (from Protegrin I) | RRLSYSRRRF (SEQ ID NO: 9) |

In certain embodiments a fusion protein may be generated that contains both a region responsible for the bioactive (e.g., therapeutic) properties of the polypeptide as well as a region that improves the cellular uptake of the protein. For example, in certain embodiments, the fusion protein may contain part or all of the influnza virus hemagglutinin protein.

B. Nanoparticles

As used herein, the term "nanoparticle" refers to any material having dimensions in the 1-1,000 nm range. In some embodiments, nanoparticles have dimensions in the 2-200 nm range, preferably in the 2-150 nm range, and even more prefereably in the 2-100 nm range. Nanoparticles used in the present invention include such nanoscale materials as a lipid-based nanoparticle, a superparamagnetic nanoparticle, a nanoshell, a semiconductor nanocrystal, a quantum dot, a polymer-based nanoparticle, a silicon-based nanoparticle, a silica-based nanoparticle, a metal-based nanoparticle, a fullerene and a nanotube (Ferrari, 2005). The conjugation of polypeptides to nanoparticles provides structures with potential application for targeted delivery, controlled release, enhanced cellular uptake and intracellular trafficking, and molecular imaging of therapeutic peptides in vitro and in vivo (West, 2004; Stayton et al, 2000; Ballou et al., 2004; Frangioni, 2003; Dubertret et al., 2002; Michalet et al., 2005; Dwarakanath et al., 2004.

1. Superparamagnetic Iron Oxide ("SPIO") Nanoparticles

Superparamagnetic iron oxide ("SPIO") nanoparticles have been used experimentally for magnetic resonance imaging ("MRI") contrast enhancement, tissue repair, immunoassy, cell separation, and drug delivery (Gupta, 2004; Sestier et al., 1998; Wilhelm et al., 2003).

The SPIO nanoparticles for use in the present invention can be prepared and stored by any method known to those of skill in the art (Gupta et al., 2005). Commercially prepared SPIO nanoparticles can also be used. For attachment of a polypeptide, the SPIO nanoparticles can be coated with a polymeric material such as polyethylene glycol or dextran, and the polypeptide bound to the polymer surface through amide or ester bonds. A variety of chemical schemes can be used to attach the polypeptide, including carbodiimide chemistry, diisocyanate linkers, and succinimidyl esters. Linker molecules that have been used to attach polypeptides include 1-ethyl-3-(3-dimethylaminopropyl) cabodiimide hydrochloride, N-succinimidyl 3-(2 pyridyldithio) propionate, N-hydroxysuccinimide, and N,N'methylene bis acrylamide (Lewin et al., 2000; Roberts et al., 2002).

For example, a SPIO nanoparticle-peptide complex can be prepared by conjugating the peptide to the nanoparticle through a two-step procedure using a heterobifunctional linker. First, commercially prepared dextran-coated SPIO particles ("Feridex I.V" or "Combidex" from Advanced Magnetics Inc., Cambridge, Mass., or "Endorem" from Guerbet, Aulnaysous-Bois, France) are derivatized by crosslinking with epichlorohydrin and then reacted with ammonia to generate amino groups on the dextran coating. The nanoparticles are then be modified with SMCC to provide a maleimide moiety (SPIO-SMCC). Second, a peptide-hydrazone derivative is conjugated to the SPIO-SMCC by reaction of the maleimide group in SPIO-SMCC with a thiol group of the peptide derivative that is obtained after reduction of its disulfide by TCEP. The ratio of the resulting peptide-SPIO conjugation is determined by UV-visible spectrophotometry and further purified by size exclusion chromatography with a G-25 gel filtration column. The purified conjugate is concentrated and stored at −20° C. until further use. Drug derivatives are conjugated to SPIO with a similar chemistry. For fluorescence labeling of the SPIO, the primary amines of above SPIO dextran derivatives are coupled with a DTPA isothiocynate chelator (I-24221, Molecular Probes) to introduce a high-affinity binding site for a variety of metal ions, and then labeled with Fluo-3 potassium (Orange-red) (F-3715, Molecular Probes). The fluorescence-labeled FP-SPIO nanoparticles can be used for monitoring cellular uptake, intracellular trafficking, and biodistribution in vitro and in vivo by a confocal fluorescence imaging or FACS analysis.

A polypeptide can be modified at its carboxy-terminus to add a lysine or cysteine residue to provide a free primary amine or thiol functional group for conjugation to a SPIO nanoparticle. Similarly, the modified polypeptide can be conjugated to other nanoparticles, such as nanoshells, quantum dots, fullerenes and nanotubes.

For example, a lysine residue can be added to a peptide during synthesis using standard Fmoc peptide chemistry on an automated synthesizer. A cysteine residue can be added is the same manner. For polypeptides prepared by recombinant methods, a lysine or cysteine codon can be added to the DNA sequence encoding the polypeptide, and the resulting polypeptide can be expressed in recombinant expression systems.

2. Lipid-Based Nanoparticles

Lipid-based nanoparticles include liposomes, lipid preparations and lipid-based vesicles (e.g., DOTAP:cholesterol vesicles). Lipid-based naoparticles may be positively charged, negatively charged or neutral. In certain embodiments, the lipid-based nanoparticle is neutrally charged (e.g., a DOPC liposome).

a. Liposomes

A "liposome" is a generic term encompassing a variety of single and multilamellar lipid vehicles formed by the generation of enclosed lipid bilayers or aggregates. Liposomes may be characterized as having vesicular structures with a bilayer membrane, generally comprising a phospholipid, and an inner medium that generally comprises an aqueous composition. Liposomes of the present invention include unilamellar liposomes, multilamellar liposomes and multivesicular liposomes. Liposomes of the present invention may be positively charged, negatively charged or neturally charged. In certain embodiments, the liposomes are neutral in charge.

A multilamellar liposome has multiple lipid layers separated by aqueous medium. They form spontaneously when lipids comprising phospholipids are suspended in an excess of aqueous solution. The lipid components undergo self-rearrangement before the formation of closed structures and entrap water and dissolved solutes between the lipid bilayers (Ghosh and Bachhawat, 1991). Lipophilic molecules or molecules with lipophilic regions may also dissolve in or associate with the lipid bilayer.

In specific aspects, a polypeptide may be, for example, encapsulated in the aqueous interior of a liposome, interspersed within the lipid bilayer of a liposome, attached to a liposome via a linking molecule that is associated with both the liposome and the polypeptide, entrapped in a liposome, complexed with a liposome, or the like.

A liposome used according to the present invention can be made by different methods, as would be known to one of ordinary skill in the art. For example, a phospholipid (Avanti Polar Lipids, Alabaster, Ala.), such as for example the neutral phospholipid dioleoylphosphatidylcholine (DOPC), is dissolved in tert-butanol. The lipid(s) is then mixed with a bioactive polypeptide, and/or other component(s). Tween 20 is added to the lipid mixture such that Tween 20 is about 5% of the composition's weight. Excess tert-butanol is added to this mixture such that the volume of tert-butanol is at least 95%. The mixture is vortexed, frozen in a dry ice/acetone bath and lyophilized overnight. The lyophilized preparation is stored at −20° C. and can be used up to three months. When required the lyophilized liposomes are reconstituted in 0.9% saline.

Alternatively, a liposome can be prepared by mixing lipids in a solvent in a container, e.g., a glass, pear-shaped flask. The container should have a volume ten-times greater than the volume of the expected suspension of liposomes. Using a rotary evaporator, the solvent is removed at approximately 40° C. under negative pressure. The solvent normally is removed within about 5 min. to 2 hours, depending on the desired volume of the liposomes. The composition can be dried further in a desiccator under vacuum. The dried lipids generally are discarded after about 1 week because of a tendency to deteriorate with time.

Dried lipids can be hydrated at approximately 25-50 mM phospholipid in sterile, pyrogen-free water by shaking until all the lipid film is resuspended. The aqueous liposomes can be then separated into aliquots, each placed in a vial, lyophilized and sealed under vacuum.

The dried lipids or lyophilized liposomes prepared as described above may be dehydrated and reconstituted in a solution of a protein or peptide and diluted to an appropriate concentration with an suitable solvent, e.g., DPBS. The mixture is then vigorously shaken in a vortex mixer. Unencapsulated additional materials, such as agents including but not limited to hormones, drugs, nucleic acid constructs and the like, are removed by centrifugation at 29,000×g and the liposomal pellets washed. The washed liposomes are resuspended at an appropriate total phospholipid concentration, e.g., about 50-200 mM. The amount of additional material or active agent encapsulated can be determined in accordance with standard methods. After determination of the amount of additional material or active agent encapsulated in the liposome preparation, the liposomes may be diluted to appropriate concentrations and stored at 4° C. until use. A pharmaceutical composition comprising the liposomes will usually include a sterile, pharmaceutically acceptable carrier or diluent, such as water or saline solution.

In other alternative methods, liposomes can be prepared in accordance with other known laboratory procedures (e.g., see Bangham et al., 1965; Gregoriadis, 1979; Deamer and Uster, 1983; Szoka and Papahadjopoulos, 1978, each incorporated herein by reference in relevant part). Additional liposomes which may be useful with the present invention include cationic liposomes, for example, as described in WO02/100435A1, U.S. Pat. No. 5,962,016, U.S. Application 2004/0208921, WO03/015757A1, WO04029213A2, U.S. Pat. No. 5,030,453, and U.S. Pat. No. 6,680,068, all of which are hereby incorporated by reference in their entirety without disclaimer. A process of making liposomes is also described in WO04/002453A1. Neutral lipids can be incorporated into cationic liposomes (e.g., Farhood et al., 1995). Various neutral liposomes which may be used in certain embodiments are disclosed in U.S. Pat. No. 5,855,911, which is incorporated herein by reference. These methods differ in their respective abilities to entrap aqueous material and their respective aqueous space-to-lipid ratios.

The size of a liposome varies depending on the method of synthesis. Liposomes in the present invention can be a variety of sizes. In certain embodiments, the liposomes are small, e.g., less than about 100 nm, about 90 nm, about 80 nm, about 70 nm, about 60 nm, or less than about 50 nm in external diameter. In preparing such liposomes, any protocol described herein, or as would be known to one of ordinary skill in the art may be used. Additional non-limiting examples of preparing liposomes are described in U.S. Pat. Nos. 4,728,578, 4,728,575, 4,737,323, 4,533,254, 4,162,282, 4,310,505, and 4,921,706; International Applications PCT/US85/01161 and PCT/US89/05040; U.K. Patent Application GB 2193095 A; Mayer et al., 1986; Hope et al., 1985; Mayhew et al. 1987; Mayhew et al., 1984; Cheng et al., 1987; and Liposome Technology, 1984, each incorporated herein by reference).

b. Neutral Liposomes

In certain embodiments, the lipid based nanoparticle is a neutral liposome (e.g., a DOPC liposome). "Neutral liposomes" or "non-charged liposomes", as used herein, are defined as liposomes having one or more lipid components that yield an essentially-neutral, net charge (substantially non-charged). By "essentially neutral" or "essentially non-charged", it is meant that few, if any, lipid components within a given population (e.g., a population of liposomes) include a charge that is not canceled by an opposite charge of another component (i.e., fewer than 10% of components include a non-canceled charge, more preferably fewer than 5%, and most preferably fewer than 1%). In certain embodiments, neutral liposomes may include mostly lipids and/or phospholipids that are themselves neutral under physiological conditions (i.e., at about pH 7).

Liposomes and/or lipid-based nanoparticles of the present invention may comprise a phospholipid. In certain embodiments, a single kind of phospholipid may be used in the creation of liposomes (e.g., a neutral phospholipid, such as DOPC, may be used to generate neutral liposomes). In other embodiments, more than one kind of phospholipid may be used to create liposomes.

Phospholipids include, for example, phosphatidylcholines, phosphatidylglycerols, and phosphatidylethanolamines; because phosphatidylethanolamines and phosphatidyl cholines are non-charged under physiological conditions (i.e., at about pH 7), these compounds may be particularly useful for generating neutral liposomes. In certain embodiments, the phospholipid DOPC is used to produce non-charged liposomes. In certain embodiments, a lipid that is not a phospholipid (e.g., a cholesterol) may be used Phospholipids include glycerophospholipids and certain sphingolipids. Phospholipids include, but are not limited to, dioleoylphosphatidylycholine ("DOPC"), egg phosphatidylcholine ("EPC"), dilauryloylphosphatidylcholine ("DLPC"), dimyristoylphosphatidylcholine ("DMPC"), dipalmitoylphosphatidylcholine ("DPPC"), distearoylphosphatidylcholine ("DSPC"), 1-myristoyl-2-palmitoyl phosphatidylcholine ("MPPC"), 1-palmitoyl-2-myristoyl phosphatidylcholine ("PMPC"), 1-palmitoyl-2-stearoyl phosphatidylcholine ("PSPC"), 1-stearoyl-2-palmitoyl phosphatidylcholine ("SPPC"), dilauryloylphosphatidylglycerol ("DLPG"), dimyristoylphosphatidylglycerol ("DMPG"), dipalmitoylphosphatidylglycerol ("DPPG"), distearoylphosphatidylglycerol ("DSPG"), distearoyl sphingomyelin ("DSSP"), distearoylphophatidylethanolamine ("DSPE"), dioleoylphosphatidylglycerol ("DOPG"), dimyristoyl phosphatidic acid ("DMPA"), dipalmitoyl phosphatidic acid ("DPPA"), dimyristoyl phosphatidylethanolamine ("DMPE"), dipalmitoyl phosphatidylethanolamine ("DPPE"), dimyristoyl phosphatidylserine ("DMPS"), dipalmitoyl phosphatidylserine ("DPPS"), brain phosphatidylserine ("BPS"), brain sphingomyelin ("BSP"), dipalmitoyl sphingomyelin ("DPSP"), dimyristyl phosphatidylcholine ("DMPC"), 1,2-distearoyl-sn-glycero-3-phosphocholine ("DAPC"), 1,2-diarachidoyl-sn-glycero-3-phosphocholine ("DBPC"), 1,2-dieicosenoyl-sn-glycero-3-phosphocholine ("DEPC"), dioleoylphosphatidylethanolamine ("DOPE"), palmitoyloeoyl phosphatidylcholine ("POPC"), palmitoyloeoyl phosphatidylethanolamine ("POPE"), lysophosphatidylcholine, lysophosphatidylethanolamine, and dilinoleoylphosphatidylcholine.

Phospholipids may be from natural or synthetic sources. However, phospholipids from natural sources, such as egg or soybean phosphatidylcholine, brain phosphatidic acid, brain or plant phosphatidylinositol, heart cardiolipin and plant or bacterial phosphatidylethanolamine are not used, in certain embodiments, as the primary phosphatide (i.e., constituting 50% or more of the total phosphatide composition) because this may result in instability and leakiness of the resulting liposomes.

c. Lipid-Based Vesicles

Another type of lipid-based nanoparticle contemplated for use in the present invention is a lipid-based vesicle. Lipid-based vesicles may be generated using one or more of the lipids listed above.

In certain embodiments, the lipid-based vesicle is a DOTAP:cholesterol vesicle. DOTAP:cholesterol vesicles are prepared by mixing the cationic lipid DOTAP (1,2-bis(oleoyloxy)-3-(trimethylammonio)-propane) with cholesterol. Vesicles prepared with DNA can form a structure (called a "sandwich") where the DNA appears to be condensed between two lipid bilayers (U.S. Pat. Nos. 6,770,291 and 6,413,544).

A DOTAP:cholesterol-polypeptide complex can be prepared as in the following non-limiting example. The DOTAP:Cholesterol (DC) nanoparticles (sized 50 to 100 nm) are synthesized as described previously (U.S. Pat. Nos. 6,770,291 and 6;413,544; Templeton, 1997). Briefly, DOTAP and cholesterol are mixed in 1:1 ratio (20 µM DOTAP and 20 µM cholesterol) in chloroform and evaporated in an ice-cold rotary evaporator. The resulting mixture is re-suspended in 5% dextrose, pulse sonicated at 55° C., and lyophilized. The lyophilized product is dissolved in 5% dextrose and extruded through a mini-extruder (Avanti Lipids, Al) of decreasing size (1.0, 0.45, 0.2, and 0.1 µm) to give a mean particle size of 50 to 100 nm. DOTAP without cholesterol is prepared similarly. The synthesized nanoparticles are stored at 4° C. and used for preparing nanoparicle complexes.

To prepare DOTAP:cholesterol-peptide nanoparticles, 20 µg of peptide are diluted in 100 µl of 5% dextran in water ("D5W") and gently mixed with an equal volume of diluted DOTAP:cholesterol or DOTAP alone (dilute 40 µl of 20 mM µM DOTAP:cholesterol or DOTAP alone to a total volume of 100 µl in D5W), which gives a final concentration of 100 mg/mL of peptide and 4 mM of DOTAP:cholesterol or DOTAP. The formulation is optimized with varied rations of peptide to DOTAP:cholesterol or DOTAP. The resulting peptide-nanoparticle has mean sizes between 100-250 nm and with a positive charge of +50 mV as determined by a N4 Plus Submicron Particle Sizer the N4 particle size analyzer and a Delsa 440SX Zeta Potential Analyzer (Beckman Coulter, Inc., Fullerton, Calif., USA), respectively.

In some embodiments of the present invention, nanoparticle-polypeptide complexes formed with superparamagnetic nanoparticles are incorporated into DOTAP:cholesterol vesicles. To assemble peptide-SPIO conjugates in DOTAP:cholesterol vesicles, peptide-SPIO conjugates can be encapsulated in DOTAP:cholesterol vesicles by a self-assembling process with optimized molar ratio of each component. The peptide-SPIO nanoparticle, or individual peptide and SPIO components, are assembled by first mixing 5-50 µM peptide-SPIO conjugate or 5-50 µM peptide+0.1-1 mg of Fe (SPIO) per ml in D5W for 1 h, then combining with an equal volume of 40-100 mM of DOTAP:cholesterol vesicles in D5W. Peptide-SPIO-DOTAP:cholesterol particle and colloid stability in D5W is monitored through spectrophotometric analysis O.D. at 400 nm. The encapsulation process is to be optimized by determination of cellular uptake in tumor cells transfected with fluo-3-labeled peptide-SPIO conjugate by FACS analysis.

3. Targeting of Nanoparticles

Targeted delivery is achieved by the addition of ligands without compromising the ability of nanoparticles to deliver their polypeptide payloads. It is contemplated that this will enable delivery to specific cells, tissues and organs. The targeting specificity of the ligand-based delivery systems are based on the distribution of the ligand receptors on different cell types. The targeting ligand may either be non-covalently or covalently associated with a nanoparticle, and can be conjugated to the nanoparticles by a variety of methods as discussed herein.

Examples of proteins or peptides that can be used to target nanoparticles include transferin, lactoferrin, TGF-α, nerve growth factor, albumin, HIV Tat peptide, RGD peptide, and insulin, as well as others (Gupta et al., 2005; Ferrari, 2005).

II. Bioactive Polypeptides

The present invention provides nanoparticle-polypeptide complexes and methods of using such complexes for delivering a polypeptide to a cell. The complexes comprise a bioactive polypeptide in association with a nanoparticle. A "bioactive" polypeptide is a protein or peptide having some desired biological function or activity. As an example, desired biological functions for anti-cancer therapy include inhibiting protein kinases, promoting apoptosis, inhibiting angiogenesis, and the like. Thus, a bioactive anti-cancer polypeptide can be a polypeptide that inhibits protein kinases, promotes apoptosis, or inhibits angiogenesis.

In accordance with the present invention, nanoparticle-polypeptide complexes can be formed by associating a bioactive peptide with a nanoparticle. A bioactive peptide containing one or more functional domains of a protein of interest are particularly contemplated.

A. Creating a Bioactive Polypeptide

The present invention provides methods for identifying a producing a bioactive polypeptide (e.g., a bioactive peptide). In certain embodiments, a bioactive polypeptide may be prodiced by identifying one or more functional domains in a polypeptide.

Functional domains of a protein can be empirically determined through structure-function studies using molecular and cell biological methods that are well known in the art. For example, deletion mutants or substitution mutants of a protein can be prepared by recombinant DNA methods, and the biological properties of such mutant proteins can be studied. Alternatively, putative functional domains in a protein sequence can be identified by amino acid sequence analysis, and peptides containing these predicted functional domains can be designed and tested for biological activity.

In certain embodiments, computer-assisted structural analysis may be used to identify a functional domain in a polypeptide. Typically the computer-assisted structural analysis involves evaluating the amino acid and/or nucleotide sequence of a gene. The computer-assisted structural analysis can be used to identify, for example, a functional domain such as a protein kinase (e.g., PKC) activating or interacting site, a myristoylation site, a PDZ Class II domain or an A kinase anchoring protein (AKAP) motif. Computer-assisted structural analysis may result in the identification of a putative functional domain. Identification of a putative functional domain may be sufficient to identify a bioactive peptide. However, if confirmation of the activity of the functional domain is desired, then various biological assays which are known in the art may be used to confirm the activity of the functional domain. Software for performing computer-assisted structural analysis include the Scansite program and other analysis programs found on the ExPASy Proteomics Server.

In particular embodiments of the present invention, peptides having anti-cancer properties are contemplated. Such peptides can be based on tumor suppressor gene products.

B. Tumor Suppressor Genes

The tumor suppressor oncogenes function to inhibit excessive cellular proliferation. The inactivation of these genes destroys their inhibitory activity, resulting in unregulated proliferation.

One well studied tumor suppressor gene is p53. High levels of mutant p53 have been found in many cells transformed by chemical carcinogenesis, ultraviolet radiation, and several viruses. The p53 gene is a frequent target of mutational inactivation in a wide variety of human tumors and is already documented to be the most frequently mutated gene in common human cancers. It is mutated in over 50% of human NSCLC (Hollstein et al., 1991) and in a wide spectrum of other tumors.

The p53 gene encodes a 393-amino acid phosphoprotein that can form complexes with host proteins such as large-T antigen and E1B. The protein is found in normal tissues and cells, but at concentrations which are minute by comparison with transformed cells or tumor tissue Wild-type p53 is recognized as an important growth regulator in many cell types. Missense mutations are common for the p53 gene and are essential for the transforming ability of the oncogene. A single genetic change prompted by point mutations can create carcinogenic p53. Unlike other oncogenes, however, p53 point mutations are known to occur in at least 30 distinct codons, often creating dominant alleles that produce shifts in cell phenotype without a reduction to homozygosity. Additionally, many of these dominant negative alleles appear to be tolerated in the organism and passed on in the germ line. Various mutant alleles appear to range from minimally dysfunctional to strongly penetrant, dominant negative alleles (Weinberg, 1991).

Another inhibitor of cellular proliferation is p16. The major transitions of the eukaryotic cell cycle are triggered by cyclin-dependent kinases, or CDK's. One CDK, cyclin-dependent kinase 4 (CDK4), regulates progression through the $G_1$. The activity of this enzyme may be to phosphorylate Rb at late $G_1$. The activity of CDK4 is controlled by an activating subunit, D-type cyclin, and by an inhibitory subunit, the p16 NK4 has been biochemically characterized as a protein that specifically binds to and inhibits CDK4, and thus may regulate Rb phosphorylation (Serrano et al., 1993; Serrano et al, 1995). Since the $p16^{INK4}$ protein is a CDK4 inhibitor (Serrano, 1993), deletion of this gene may increase the activity of CDK4, resulting in hyperphosphorylation of the Rb protein. p16 also is known to regulate the function of CDK6.

$p16^{INK4}$ belongs to a newly described class of CDK-inhibitory proteins that also includes $p16^B$, p19, $p21^{WAF1}$, and $p27^{KIP1}$. The $p16^{INK4}$ gene maps to 9p21, a chromosome region frequently deleted in many tumor types. Homozygous deletions and mutations of the $p16^{INK4}$ gene are frequent in human tumor cell lines. This evidence suggests that the $p16^{INK4}$ gene is a tumor suppressor gene. This interpretation has been challenged, however, by the observation that the frequency of the $p16^{INK4}$ gene alterations is much lower in primary uncultured tumors than in cultured cell lines (Caldas et al., 1994; Cheng et al., 1994; Hussussian et al., 1994; Kamb et al., 1994; Kamb et al., 1994; Mori et al., 1994; Okamoto et al., 1994; Nobori et al., 1995; Orlow et al., 1994; Arap et al., 1995). Restoration of wild-type $p16^{INK4}$ function by transfection with a plasmid expression vector reduced colony formation by some human cancer cell lines (Okamoto, 1994; Arap, 1995).

Other tumor suppressors that may be employed according to the present invention are listed in Table IV. The genes listed in Table IV are provided as non-limiting examples of tumor suppressor genes that may be used with the present invention. Furthermore, it is envisioned that virtually any tumor suppressor gene (e.g., a pro-apoptotic gene, or a gene which is cytotoxic to a cancerous cell) that is presently known or which may be subsequently discovered may be used with the present invention. It is envisioned that virtually any human gene product that demonstrates tumor inhibitory effects could be used to derive an anti-cancer bioactive peptide.

TABLE IV

Tumor Suppressor Genes

| GENE | GENE | GENE | GENE |
|---|---|---|---|
| 101F6 | DAF-18 | HYAL2 | PTEN |
| ABR | D-APC | IGBP7 | PTPN13 |
| ADPRTL3 | DBC2 | IGSF4 | PTPRG |
| ANP32C | DCC | ING1 | RASSF1 |
| ANP32D | DDX26 | ING1L | RB1 |
| APC2 | DEC1 | ING4 | RBBP7 |
| APC | DLC1 | l(2)tid | RBM6 |
| ARF | DLEC1 | l(3)mbn | RBX1 |
| ARHGAP8 | DLEU1 | l(3)mbt | RECK |
| ARHI | DLEU2 | LAPSER1 | RFP2 |
| AT1G14320 | DLG1 | LATS1 | RIS1 |
| ATM | DLGH1 | LATS2 | RPL10 |
| ATP8A2 | DLGH3 | LDOC1 | RPS29 |
| AXUD1 | DMBT1 | LOHIICR2A | RRM1 |
| BAP1 | DNAJA3 | LRPIB | S100A2 |
| BECN1 | DOC-1 | LUCA3 | SEMA3B |
| BIN1 | DPCH | MAD | SF1 |
| BRCA1 | DPH2L | MAP2K4 | SFRP1 |

TABLE IV-continued

Tumor Suppressor Genes

| GENE | GENE | GENE | GENE |
|---|---|---|---|
| BRCA2 | EGR1 | MAPKAP3 | SLC22AK |
| BTG1 | FABP3 | MCC | SLC26A3 |
| BTG2 | FAT | MDC | SMARCA4 |
| C1orf1 | FGL1 | MEN1 | ST7 |
| C5orf4 | FHIT | ML-1 | ST7L |
| C5orf7 | FLJ10506 | MLH1 | ST13 |
| Cables | FOXD1 | MRVI1 | ST14 |
| CACNA2D2 | FOXP1 | MTAP | STIM1 |
| CAP-1 | FT | MXI1 | TCEB2 |
| CARS | FUS1 | NAP1L4 | THW |
| CAV1 | FUS2 | NBR2 | Timp3 |
| CD81 | GAK | NF1 | TP53 |
| CDC | GAS1 | NF2 | TP63 |
| CDK2AP1 | GAS11 | NORE1 | TRIM8 |
| CDKN1A | GLD-1 | NPR2L | Tsc2 |
| CDKN1C | GLTSCR1 | NtRb1 | TSG1-1 |
| CDKN2A | GLTSCR2 | OVCA2 | TSSC1 |
| CDKN2B | GRC5 | PDGFRL | TSSC3 |
| CDKN2X | GRLF1 | PHEMX | TSSC4 |
| Ciao1*** | HDAC3 | PHyde | VHL |
| CLCA2 | HEMK | PlG8 | Vhlh |
| CREBL2 | HIC1 | PIK3CG | WFDC1 |
| CTNNA1 | HRG22 | PINX1 | WIT-1 |
| CUL2 | HSAL2 | PLAGL1 | WT1 |
| CW17R | HTS1 | PRDM2 | WWOX |
| DAB2 | HYAL1 | PTCH | p53 |
| bak | MDA-7 | p21 | bax |
| fas | | | |

C. Tumor Suppressor Genes from Human Chromosome 3p21.3.

Tumor suppressor genes (TSGs) play a major role in the pathogenesis of human lung cancer and other cancers. Lung cancer cells harbor mutations and deletions in multiple known dominant and recessive oncogenes (Sekido et al., 1998; Virmani et al., 1998). Known TSGs such as Rb, p53, and putative TSGs have been found at chromosome regions 3p, 5q, 6p, 8p, 9p, and 11p as well as other sites (Sekido et al., 1998; Gazdar et al., 1994; Minna, 1997). Cytogenetic and allelotyping studies of fresh lung tumors and tumor cells showed tumor-cell allele loss at multiple sites, suggesting the existence of one or more such TSGs (Sekido et al., 1998; Virmani et al., 1998; Gazdar et al., 1994; Minna et al., 1997). However, cytogenetic changes and allele loss on the short arm of chromosome 3 (3p) have been shown to be most frequently involved in about 90% of small cell lung cancers (SCLCs) and >50% of non-small cell lung cancers (NSCLCs) (Sekido et al., 1998; Gazdar et al., 1994; Minna, 1997; Daly et al., 1993). SCLC and NSCLC are the two treatment groups of lung tumors and are made up of four histological types. Squamous cell-, adeno-, and large cell carcinomas are in the NSCLC group. Small cell lung cancer is in the SCLC group. Approximately 75% of lung tumors are NSCLCs. Metastases occur later with NSCLC than with SCLC. SCLC is one of the most metastatic of solid tumors (Mabry et al., 1998). In addition, similar 3p changes have been seen in several other cancers in addition to lung, such as renal, breast, head and neck, pancreatic, kidney, oral, and uterine cervical cancers (Roth, 1998; Zbar et al., 1987; Gazdar et al., 1998; Sekido et al., 1998; Buchhagen et al., 1996; Gorunova et al., 1998; Hughson et al., 1998; Uzawa et al., 1998; Kersemaekers et al., 1998; Wistuba et al., 1997). Furthermore, a group of TSGs, as defined by homozygous deletions in lung cancers, have been located and isolated at 3p21.3 in a 450-kb region (Sekido et al., 1998; Minna et al., 1997; Hung et al., 1995; Sekido et al., 1996; Wistuba et al., 1999). Studies of lung cancer preneoplasia indicate that 3p21 allele loss is the earliest genetic abnormality in lung cancer detected so far, occurring in hyperplastic lesions; this shows that one or more 3p-recessive oncogenes function as "gatekeepers" in the molecular pathogenesis of many human cancers, including lung cancer, where it is likely to be involved in >50% of all cases (Sekido et al., 1998; Minna et al., 7 1997; Hung et al., 1995; Sekido et al., 1996; Wistuba et al., 1999; Kohno et al., 1999; Wistuba et al., 1999).

A group of genes has been identified in a 120-kb critical tumor homozygous deletion region (found in lung and breast cancers) of human chromosome 3p21.3. These genes have been designated CACNA2D2, PL6, 101F6, NPR1.2, BLU, RASSF1, FUS1, HYAL2 and HYAL1. Studies were conducted exploring the effect of expressing some of these genes on cell proliferation in several types of human NSCLC cells. These studies indicate that FUS1, 101F6, HYAL2 and NPRL2 as well as other genes are candidate tumor suppressor genes (Ji et al., 2000).

Restoration of wt-FUS1 function in 3p21.3-deficient human lung cancer cells by adenoviral vector- or DOTAP: cholesterol nanoparticle-mediated gene transfer inhibits the growth of these tumor cells by induction of apoptosis and alteration of cell kinetics in vitro and in vivo (Ito et al., 2004). This demonstrates the tumor suppressive activity of FUS1.

III. Pharmaceutical Formulations

Pharmaceutical compositions of the present invention comprise an effective amount of one or more peptides, nanoparticle-polypeptide complexes or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one peptide or nanoparticle-polypeptide complex or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The pharmaceutical composition may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g. aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

In certain embodiments, the pharmaceutical composition is administered intraperitoneally. In further embodiments, the pharmaceutical composition is administered intraperitoneally to treat a cancer (e.g., a cancerous tumor). For example, the pharmaceutical composition may be administered intraperitoneally to treat gastrointestinal cancer. In certain embodiments it may be disirable to administer the pharmaceutical composition into or near a tumor.

In certain preferred embodiments, the pharmaceutical composition is administered orally to treat a cancer (e.g., a gastrointestinal cancer).

The actual dosage amount of a composition of the present invention administered to a patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The one or more peptides, nanoparticle-polypeptide complexes or additional agent may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g. triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the one or more peptides or nanoparticle-polypeptide complexes are prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

IV. Magnetic Resonance Imaging

In magnetic resonance imaging (MRI), a patient lies in a static magnetic field and is subjected to an imaging sequence using radiofrequency (RF) pulses and spatial and temporal magnetic field gradients. MRI uses the property of nuclear spin to collect image data. Nuclei with unpaired nucleons (protons or neutrons) possess a property known as spin, which results in a non-zero magnetic moment that can be used to conduct MRI (see, e.g., U.S. Pat. No. 5,397,987). Hydrogen nuclei have a single proton, and many MRI techniques utilize hydrogen nuclei since they are pervasive in human tissue. When a subject is placed in a main magnetic field, its nuclei align in the direction of the field (i.e., along the "magnetization axis"); the orientation of the nuclei can be represented by a magnetization vector (see, e.g., Horowitz, 1995). In the classical physical description of magnetic resonance, these spinning nuclei can precess in a conical manner around the magnetization axis, generally out-of-phase with respect to each other.

To induce in-phase spinning at the resonance frequency of particular nuclei, a high-powered radio frequency excitation pulse, frequently in the kilowatt range, is broadcast at that resonance frequency. This RF pulse also causes the nuclei in a sample (e.g., a human brain) to rotate with respect to the magnetization vector created by the main magnetic field (see, e.g., Horowitz, 1995). The spinning nuclei in the sample generate RF signals, which decay over time. Time-varying gradient magnetic fields are applied after the RF excitation pulse to permit spatial resolution of the decaying RF signals. Thus, the RF excitation pulse and the time-varying gradient magnetic fields together cause the sample to emit time-varying MR RF signals known as "free induction decay" (FID) signals. An antenna in the magnetic resonance (MR) scanner receives these FID signals, and these MR imaging signals are transmitted to a processor. The processor uses these signals to generate MR images that reflect the spatial distribution or chemical environment of the spinning nuclei.

Contrast agents are used to increase the difference in signal between an area of interest to the background. Superparamagnetic nanoparticles can be used as contrast agents in MRI (Gupta et al., 2005; Ferrari, 2005). The particles can accumulate in a tissue, such as a tumor, either passively or by targeted delivery (Morawski et al., 2005). The use of magnetic fields to localize such particles in a particular tissue is also possible. Targeted delivery can also involve the incorporation of particular proteins such as transferin, as describe above.

A superparamagnetic nanoparticle-polypeptide complex of the present invention can be used in MRI to identify tissues and cells that take up bioactive polypeptides.

Prior to use, the nanoparticle (e.g., a peptide-SPIO-DOTAP:cholesterol particle) can be evaluated for cytotoxicity in vitro. Human cancer cells can be used to evaluate effects of the peptide-SPIO-DOTAP:cholesterol particles on cell growth and the induction of apoptosis in vitro. As a non-limiting example, cytotoxicity measurements are performed in 96-well plates with $1 \times 10^4$ cells per well by XTT assay. Cells are rinsed with PBS and incubated with peptide-SPIO-DOTAP:cholesterol particles that are diluted in serum-free medium to a final concentration about 1-10 mM peptide-SPIO conjugates, and 4-10 mM DOTAP:cholesterol. Peptide, SPIO, and DOTAP:cholesterol particles are used as controls for 30 min on a 96-well magnetic plate (Dynal Biotech Inc., Brown Deer, Wis.). Excess unbound particles are removed by rinsing three times with PBS. Fresh culture medium is then added to the wells. The cytotoxicity and induction of apoptosis is determined at 24, 48, and 72 h post-treatment. Cell viability is measured by using an XTT assay (Roche Biochemicals) according to the manufacturer's instruction, and apoptosis is measured by FACS analysis with a TUNEL-staining. Peptide-DOTAP:cholesterol particles can serve as a positive control To evaluate cellular uptake and trafficking of peptide-SPIO nanoparticles in vitro, tumor cells treated as above can be used to quantitatively measure the uptake of fluo-3-labeled peptide-SPIO nanoparticles as a function of peptide-SPIO concentration by FACS analysis. The cellular uptake can also be determined and quantitatively analyzed by magnetic resonance (MR). As a non-limiting example, peptide-SPIO-transfected H1299 cells are suspended in 15% gelatin at 42° C. at varied cell concentrations of 0, 315, 625, 125, 2500, 5000, and 10000 cells/ml and then cooled to room temperature to form gelatin cell block in a 1.5 ml-microcentrifuge plastic tube. T2-weighted MR images of phantoms are obtained by using a 4.7-T Bruker MR. A 3D gradient echo sequence is used for data acquisition. Sequence parameters are: TR25 msec, TE5.1 msec, and AC128. The 3D slab is oriented sagittaly with the dimensions: FOV632.4 cm, matrix 25612896. Oblique projections (with respect to the magnet axes) are then reconstructed within the Paravision acquisition and processing software package (Bruker, Germany) to obtain the anatomically relevant planes. Phantoms containing peptide-SPIO-transfected H1299 cells are measured by a similar sequence with different geometry: FOV6 cm, matrix 256256, slice thickness 1 mm. In some cases, only one slice is measured in the case of phantoms MR. The concentrations of peptide-SPIO in cells is calculated based on a standard curve generated from a serial dilution of peptide-SPIO-DOTAP:cholesterol particles in solution by MR146. Fluo-3-labeled peptide-SPIO nanaoparticles can also be used to evaluate internalization using a trypan blue quenching assay to extinguish extracellular fluorescence and using a confocal fluorescence microscopy to visualize the internalization of peptide-SPIO conjugate.

To evaluate magnetic force-driven targeted delivery and therapeutic efficacy of nanoparticles (e.g., peptide-SPIO-DOTAP:cholesterol or peptide-SPIO-DOPC) in vivo, a human cancer mouse can be used for evaluation of the magnetically targeted delivery and therapeutic efficacy of peptide-SPIO nanoparticles by systemic administration. As a non-limiting example, tumor cells are inoculated in nude mice by intrathoracic injection as described previously. Seven to 10 days after tumor cell inoculation, mice are injected with 100 ml of peptide-SPIO-DOTAP:cholesterol particles at a concentration of about 5 mM peptide-SPIO conjugates, 4 mM DOTAP:cholesterol, and peptide-DOTAP:cholesterol and SPIO-DOTAP:cholesterol particles are used as controls, and PBS alone is used as a mock control. Three animals will be used for each treatment group five to 30 min after injection tumor sites are subjected to a magnetic gradient fields with a predetermined field strength and localization distance and area based on the MRI for 10-30 min at lung tumor sites. MRI is used for treatment planning, localization, and monitoring of the peptide-SPIO distribution and the therapeutic efficacy after treatment using a 4.7 T, 40 cm Bruker Biospec MR instrument].

V. Combination Therapies

In order to increase the effectiveness of a peptide or nanoparticle-polypeptide complex of the present invention, it may be desirable to combine these compositions with other agents effective in the treatment of the disease of interest.

As a non-limiting example, the treatment of cancer may be implemented with anti-cancer bioactive peptides or nanoparticle-polypeptide complexes of the present invention along with other anti-cancer agents. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cells with the anti-cancer peptide or nanoparticle-polypeptide complex and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the anti-cancer peptide or nanoparticle-polypeptide complex and the other includes the second agent(s). In particular embodiments, an anti-cancer peptide can be one agent, and an anti-cancer nanoparticle-polypeptide complex can be the other agent.

Treatment with the anti-cancer peptide or nanoparticle-polypeptide complex may precede or follow the other agent treatment by intervals ranging from minutes to weeks. In embodiments where the other agent and the anti-cancer peptide or nanoparticle-polypeptide complex are applied separately to the cell, one would generally ensure that a significant period of time did not expire between the time of each delivery, such that the agent and the anti-cancer peptide or nanoparticle-polypeptide complex would still be able to exert an advantageously combined effect on the cell. In such instances, it is contemplated that one may contact the cell with both modalities within about 12-24 hours of each other and, more preferably, within about 6-12 hours of each other. In some situations, it may be desirable to extend the time period for treatment significantly where several days (e.g., 2, 3, 4, 5, 6 or 7 days) to several weeks (e.g., 1, 2, 3, 4, 5, 6, 7 or 8 weeks) lapse between the respective administrations.

Various combinations may be employed, where the anti-cancer peptide or nanoparticle-polypeptide complex is "A" and the secondary agent, such as radio- or chemotherapy, is "B":

```
A/B/A  B/A/B  B/B/A  A/A/B  A/B/B  B/A/A  A/B/B/B
B/A/B/B  B/B/B/A  B/B/A/B  A/A/B/B  A/B/A/B  A/B/B/A
B/B/A/A  B/A/B/A  B/A/A/B  A/A/A/B  B/A/A/A  A/B/A/A
A/A/B/A
```

Administration of the therapeutic anti-cancer peptide or nanoparticle-polypeptide complex of the present invention to a patient will follow general protocols for the administration of chemotherapeutics, taking into account the toxicity, if any, of the vector. It is expected that the treatment cycles would be repeated as necessary. It also is contemplated that various standard therapies, as well as surgical intervention, may be applied in combination with the described hyperproliferative cell therapy.

a. Chemotherapy

Cancer therapies also include a variety of combination therapies with both chemical and radiation based treatments. Combination chemotherapies include, for example, gefitinib, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin, Gleevac (imatinib mesylate), and methotrexate, or any analog or derivative variant of the foregoing. In certain embodiments, the present invention may be used in combination with gefitinib. In other embodiments, the present invention may be practiced in combination with Gleevac (e.g., from about 400 to about 800 mg/day of Gleevac may be administered to a patient). In certain embodiments, one or more chemotherapeutic may be used in combination with the present invention.

b. Radiotherapy Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic composition and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

C. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with a peptide or nanoparticle-polypeptide complex of the present invention. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

d. Gene Therapy

In yet another embodiment, the secondary treatment is a gene therapy in which a therapeutic polynucleotide is administered before, after, or at the same time as the therapeutic composition. Viral vectors for the expression of a gene product are well known in the art, and include such eukaryotic expression systems as adenoviruses, adeno-associated viruses, retroviruses, herpesviruses, lentiviruses, poxviruses including vaccinia viruses, and papiloma viruses, including SV40. Alternatively, the administration of expression constructs can be accomplished with lipid based vectors such as liposomes or DOTAP:cholesterol vesicles. All of these method are well known in the art (see, e.g. Sambrook et al., 1989; Ausubel et al., 1998; Ausubel, 1996).

Delivery of a vector encoding one of the following gene products will have a combined anti-hyperproliferative effect on target tissues. A variety of proteins are encompassed within the invention, some of which are described below.

ii. Inhibitors of Cellular Proliferation

As noted above, the tumor suppressor oncogenes function to inhibit excessive cellular proliferation. The inactivation of these genes destroys their inhibitory activity, resulting in unregulated proliferation.

Genes that may be employed as secondary treatment in accordance with the present invention include p53, p16, Rb, APC, DCC, NF-1, NF-2, WT-1, MEN-I, MEN-II, zac1, p73, VHL, MMAC1/PTEN, DBCCR-1, FCC, rsk-3, p27, p27/p16 fusions, p21/p27 fusions, anti-thrombotic genes (e.g., COX-1, TFPI), PGS, Dp, E2F, ras, myc, neu, raf, erb, fms, trk, ret, gsp, hst, abl, E1A, p300, genes involved in angiogenesis (e.g., VEGF, FGF, thrombospondin, BAI-1, GDAIF, or their receptors), MCC and other genes listed in Table IV.

ii. Regulators of Programmed Cell Death

Apoptosis, or programmed cell death, is an essential process for normal embryonic development, maintaining homeostasis in adult tissues, and suppressing carcinogenesis (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, *Proc. Nat'l. Acad. Sci. USA*, 82(21):7439-43, 1985; Cleary et al., 1986; Tsujimoto et al., 1985; Tsujimoto and Croce, 1986). The evolutionarily conserved Bcl-2 protein now is recognized to be a member of a family of related proteins, which can be categorized as death agonists or death antagonists.

Subsequent to its discovery, it was shown that Bcl-2 acts to suppress cell death triggered by a variety of stimuli. Also, it now is apparent that there is a family of Bcl-2 cell death regulatory proteins which share in common structural and sequence homologies. These different family members have been shown to either possess similar functions to Bcl-2 (e.g., $Bcl_{XL}$, $Bcl_W$, $Bcl_S$, Mcl-1, A1, Bfl-1) or counteract Bcl-2 function and promote cell death (e.g., Bax, Bak, Bik, Bim, Bid, Bad, Harakiri).

e. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

f. Other Agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adehesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyerproliferative efficacy of the treatments. Inhibitors of cell adehesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

\* \* \*

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

FUS1 is a novel tumor suppressor gene (TSG) identified in the human chromosome 3p21.3 region that is frequently altered or deleted in many human cancers and has been shown to function as a key mediator in the Apaf1-associated apoptotic pathway, and is a potent tumor suppressor in vitro and in vivo. Loss of expression and deficiency of posttranslational modification of FUS1 protein have been found in a majority of NSCLCs and in almost all SCLCs. Restoration of wt-FUS1 function in 3p21.3-deficient human lung cancer cells by adenoviral vector- or DOTAP:cholesterol nanoparticle-mediated gene transfer inhibits the growth of these tumor cells by induction of apoptosis and alteration of cell kinetics in vitro and in vivo. In this study, the inventors used a computer-assisted structural analysis of Fus1 protein and found several potential PKC activating/interacting sites and an A kinase anchoring protein (AKAP)-interacting motif in the Fus1 protein sequence. Based on these functional domain predictions, the inventors have developed a group of peptides directly derived from the wt-Fus1 protein sequence, including peptides containing the wt-Fus1 amino acid sequence (wt-FP) or functional mutations (mt-FPs). The wt-FP, derived from a region that was deleted in one of the mutant Fus1 proteins detected in some lung cancer cell lines and contains a potential AKAP signaling/interacting sequence motif study. The dysfunctional mt-FPs in which several highly hydrophobic amino acid residuals are replaces with hydrophilic residuals to alter the bio-functionally critical hydrophobic micro-environment are designed to be used as controls for the wt-FP activity. A 18-C stearate saturated fatty acid chain was added to the N-termini of each peptide to make it cell permeable and also to maintain the functional integrity of the original myristoylated wt-FUS1 protein found in normal cells.

The inventors evaluated the biological function of the wt-FP in vitro and found that the stearate-wt-FP (st-wt-FP) functioned as a potent protein tyrosine kinase (PTK) inhibitor and exhibited inhibitory effects on activities of several key oncogenic PTKs such as EGFR, PDGFR, c-Kit, c-Abl, Erk in NSCLC and SCLC cells. A significant inhibition of tumor cell growth and induction of apoptosis are also observed in various lung cancer cells treated with st-wt-FP, with IC50 values range from 5-20 μM, compared to those treated with control peptides at the same concentrations. The inventors explored the use of wt-FP as a modulator for enhancing chemotherapeutic potency of PTK inhibitor such as gefitinib and Gleevec to overcome chemotherapeutical resistance in both gefitinib and Gleevec-sensitive and resistant NSCLC and SCLC cells, respectively. The inventors found that treatment of wt-FUS1 could significantly sensitize the response to Gefitinib or Gleevec treatment. A significant growth inhibition and apoptosis were observed in SCLC cells treated by the wt-FP. An enhanced growth inhibition was detected in gleevec-resistant H69R and N417 cells treated by a combination of the wt-FP with gleevec compared to those treated by either agent alone. Activities of the phosphorylated c-Abl and c-Kit proteins were also significantly inhibited in SCLC cells treated by wt-FP alone or in combination with gleevec, as shown by both the immuno-blot analysis and the activity assay using the immuno-precipiated phosho-c-Abl or phospho-c-Kit proteins.

The inventors also developed methods and protocols for preparation of FP-nanoparticle by complexion of FP and other nonspecific control peptides (NSP) with DOTAP or DOTAP:cholesterol nanoparticles for in vitro and in vivo delivery of therapeutic peptides. Cellular uptake of the peptide is dramatically increased in cells treated with FP-nanoparticle, compared to those treated with uncomplexed peptides, as demonstrated by fluorescence imaging analysis using the fluorescence-labeled peptides. A significant induction of apoptosis is also observed in NSCLC cells treated with wt-FP-nanoparticles, compared to those untreated or treated with uncomplexed wt-FP, NSP or NSP-nanoparticle controls.

The results demonstrate the therapeutic efficacy of FP-nanoparticle on NSCL and SCLC in vitro and in vivo and implicate the translational applications of using the systemic administration of FP-nanoparticle alone or in combination with other chemotherapeutic agents for the efficient treatment of lung cancer and other human cancers.

Results

1. Design and Synthesis of FUS1 Peptides

A computer-assisted structural analysis of Fus1 protein reveals several potential PKC activating/interacting sites and an A kinase anchoring protein (AKAP)-interacting motif in the Fus1 protein sequence, as indicated in FIG. 1. The analysis was performed using the Scansite program (Obenauer et al., 2003) and other sequence analysis programs available at (scansite.mit.edu) and ExPASy Proteomics Server, (us.expasy.org). Based on these functional domain predictions, the inventors prepared a group of peptides directly derived from the wt-Fus1 protein sequence, including peptides containing the wt-Fus1 amino acid sequence (wt-FP) or functional mutations (mt-FPs). A 18-C stearate saturated fatty acid chain was added to the N-termini of each peptide to make it cell permeable also to maintain the functional integrity of the original myristoylated (a 14-C saturated fatty acid) wt-FUS1 protein found in normal cells. The stearate side chain is also essential for its biological activity on inhibition of tyrosine kinase activities as myristate is to wt-FUS1 tumor suppression activity.

The FUS1 peptide ("FP") was synthesized on a Rainin Symphony Quartet automatic peptides synthesizer, using CLEAR resin as the support and HBTU-HOBT as the coupling reagents by Peptide Synthesis Core at the University of Texas M.D. Anderson Cancer Center. Each coupling step was for three hours and repeated twice with 5-fold excess of reagents. Cleavage was performed for 3 h using a cocktail of $CF_3CO_2H$-anisole and water (95%-2.5%-2.5%). The crude peptide was purified by RP-HPLC using a linear gradient of 0-70% acetonitrile in water over 40 minutes. Each solvent contained 0.1% trifluoroacetic acid.

Conjugation with stearic acid was performed using the same procedure as the amino acid coupling with 5-fold excess of reagents. A shaker was used for better mixing of reagents. Cleavage conditions were the same as that for FP. Crude Stearate-FP was purified by RP-HPLC, employing a Vydac semipreparatory diphenyl column (RP 219TP510).

Figure 2:
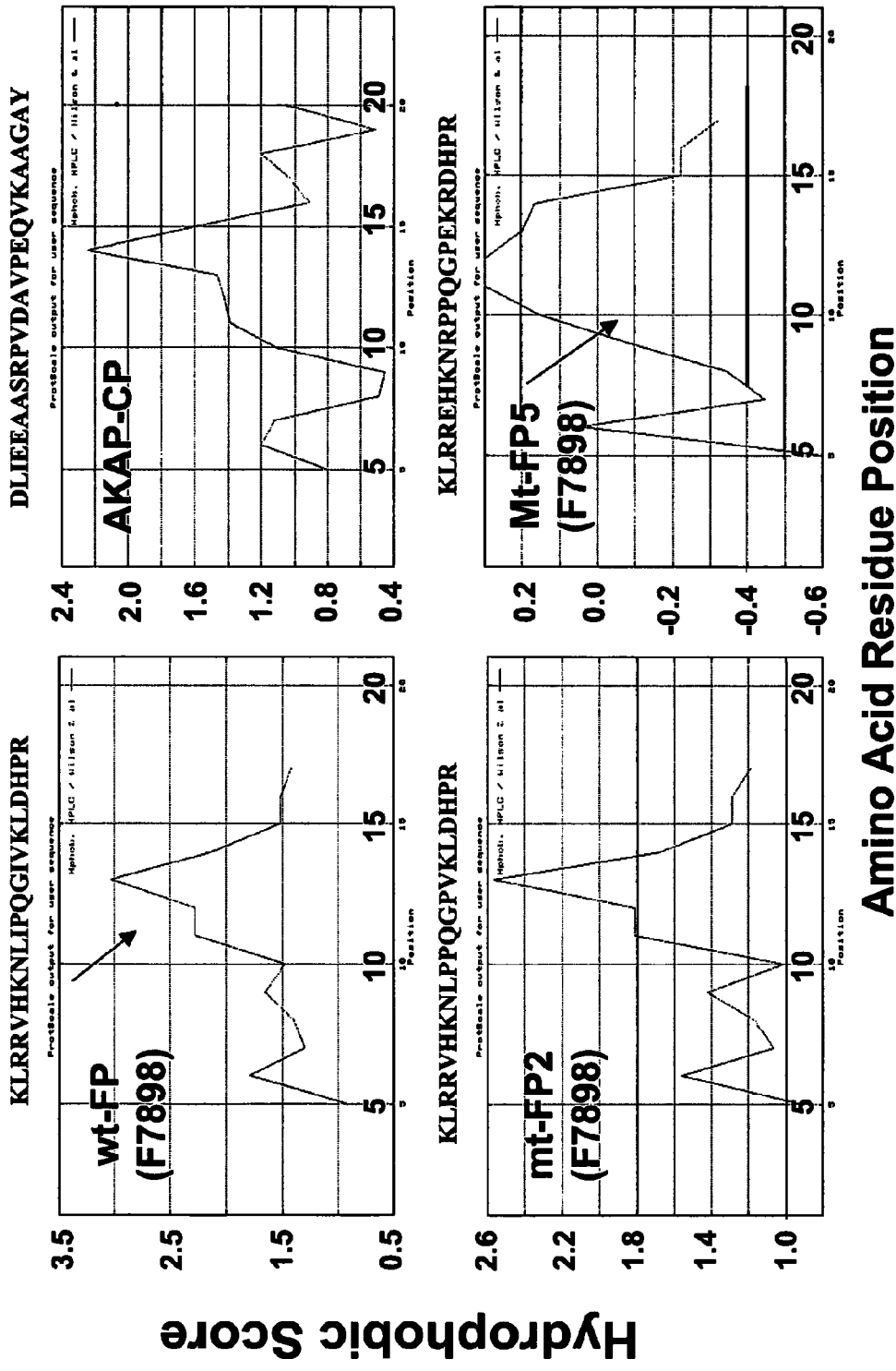
FIG. 2: The hydrophobic constants of various peptides.
Figure 3:
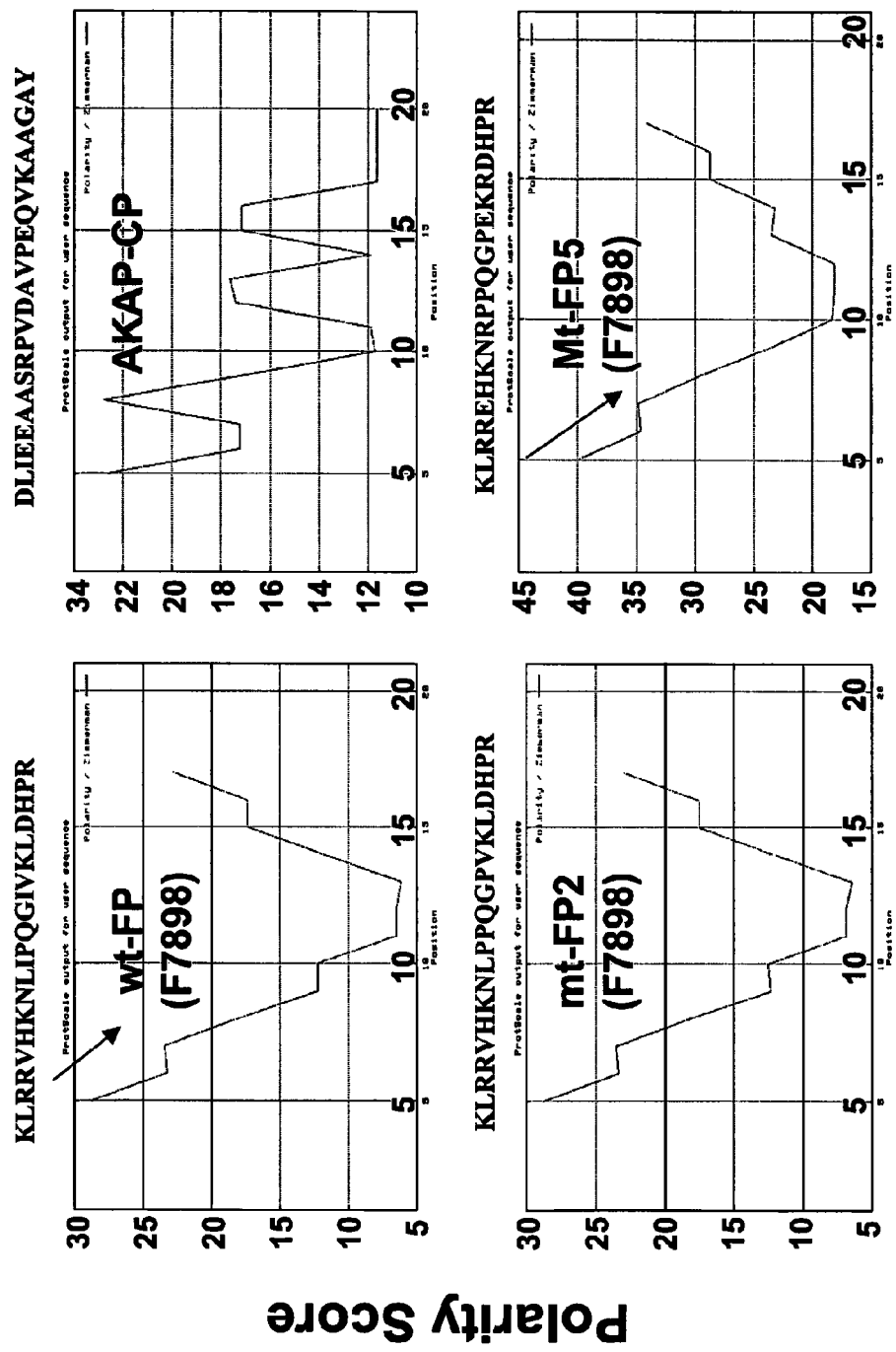
FIG. 3: The predicted polarity of Fus1 peptides.

The inventors have found that the wt-FP, derived from a region that was deleted in one of the mutant Fus1 proteins detected in some lung cancer cell lines and contains a potential protein kinase (PKA, PKC, and protein tyrosine kinases) signaling/interacting sequence motif. The dysfunctional mt-FPs in which several highly hydrophobic amino acid residuals are replaced with hydrophilic residuals to alter the biofunctionally critical hydrophobic micro-environment are designed to be used as controls for the wt-FP activity (FIG. 2), however, the polarity of these peptides are nearly unchanged, which may assure a similar solubility and accessibility under physiological condition (FIG. 3). A 18-C stearate saturated fatty acid chain was added to the N-termini of each peptide to make it cell permeable and also to maintain the functional integrity of the original myristoylated (a 14-C saturated fatty acid) wt-FUS1protein found in normal cells (FIG. 1). A non-specific control peptide (NSP), which shows no effects on protein kinase activities, was also synthesized and used as a control (FIG. 1, AKAP-CP). The myristate-peptides are to be synthesized for the comparison with the stearate-peptides.

2. Synthesis and Preparation of DOTAP:Chol-Complexed FUS1 Peptide Nanoparticles.

The DOTAP:Cholesterol ("DC") nanoparticles (sized 50 to 100 nm) are synthesized as described (Templeton, 1997). Briefly, DOTAP and cholesterol are mixed in 1:1 ratio (20 μM DOTAP and 20 μM cholesterol) in chloroform and evaporated in an ice-cold rotary evaporator. The resulting mixture is re-suspended in 5% dextrose, pulse sonicated at 55° C., and lyophilized. The lyophilized product is dissolved in 5% dextrose and extruded through a mini-extruder (Avanti Lipids, Al) of decreasing size (1.0, 0.45, 0.2, and 0.1 μm) to give a mean particle size of 50 to 100 nm. Also the DOTAP without cholesterol was also prepared similarly to be used as a transfection agent in vitro, because it was well known that transfection mediated by DC was not efficient in vitro and DOTAP was most suitable for in vitro transfection. The synthesized nanoparticles are stored at 4° C. and used for preparing DNA-nanocomplexes.

DC-DNA nanoparticle: For preparing nanocomplexes containing gene-expressing plasmid DNA, 150 μg of plasmid DNA is mixed with 20 mM DOTAP:Chol nanoparticles in a volume of 300 μl to give a final concentration of 150 μg DNA and 4 mM nanoparticles. The mean particle sizes of the DNA-nanocomplexes ranged between 300 and 325 nm as determined by using the N4 particle size analyzer (Coulter, Miami, Fla.) with a positive charge of +45 mV.

Figure 4:
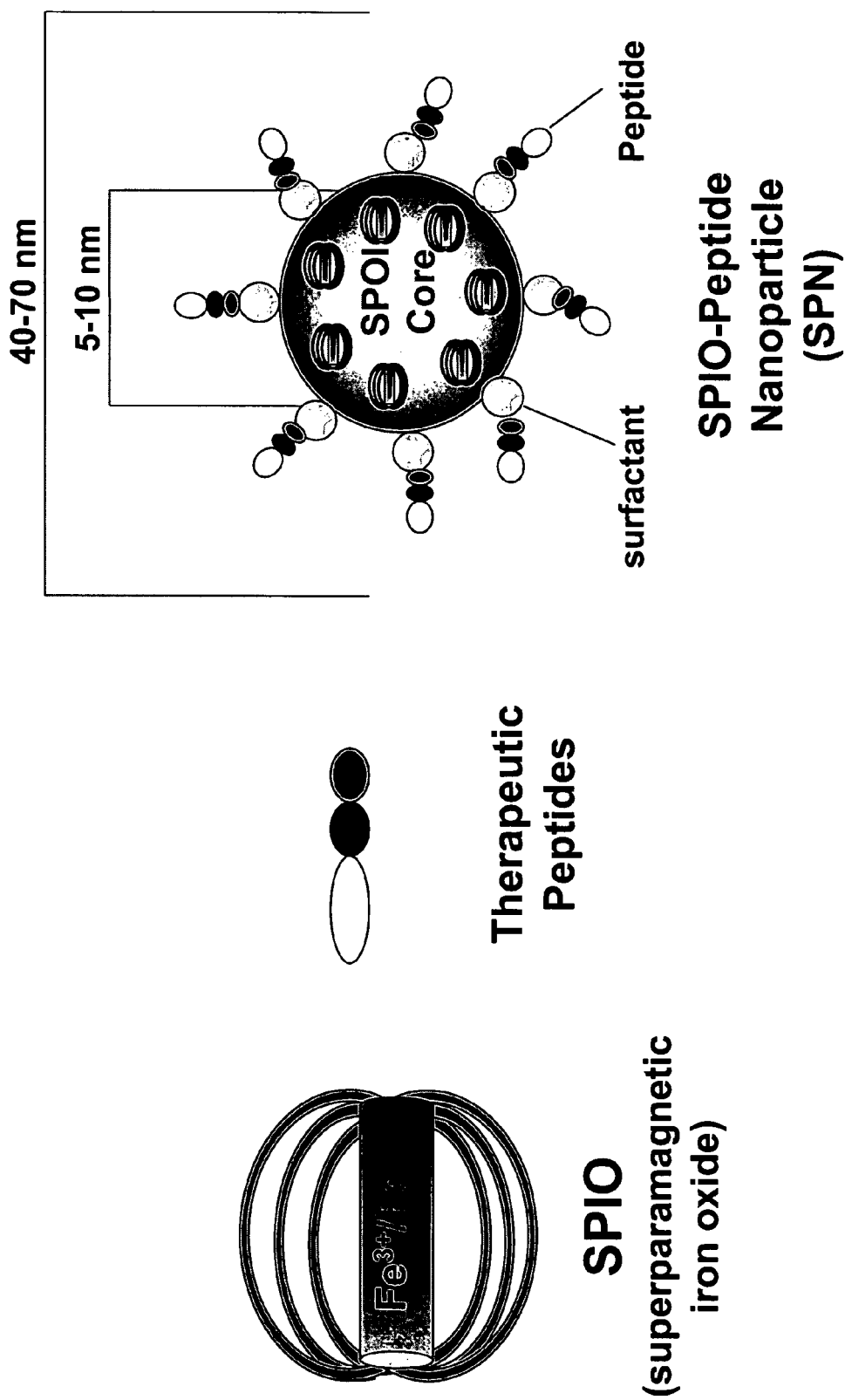
FIG. 4: A schematic diagram of a SPIO nanoparticle-peptide complex.
Figure 5:
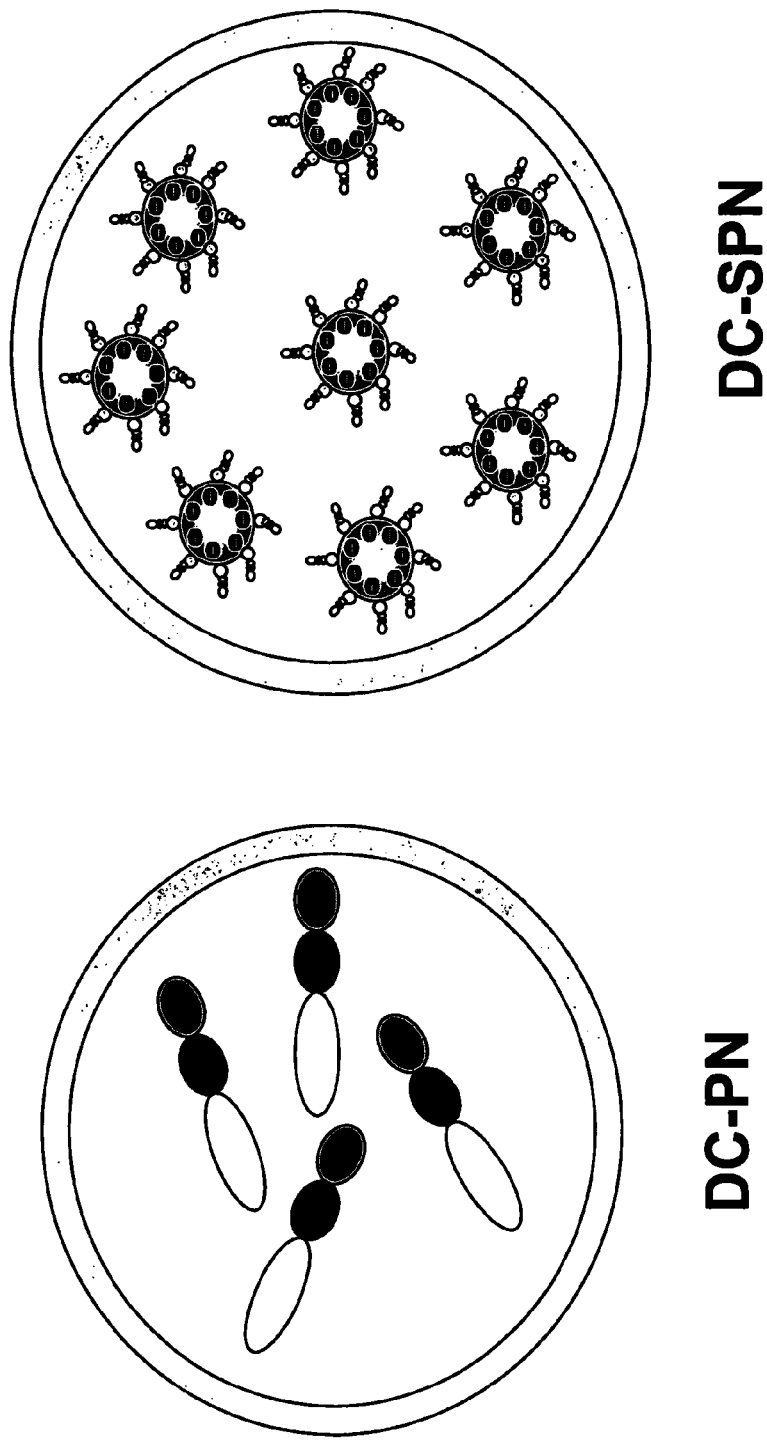
FIG. 5: A schematic diagram showing peptide-DOTAP:cholesterol nanoparticle, and a peptide-SPIO-DOTAP:cholesterol particle.

DC-peptide nanoparticle: For preparing peptide-nanoparticles, 20 μg of peptide was diluted in 100 μl of D5W and gently mix with a equal volume of diluted DOTAP:Cholesterol (DC) or DOTAP (D) (dilute 40 μl of 20 mM DC or D to a total volume of 100 μl in D5W), which give a final concentration of 100 mg/mL of peptide and 4 mM of DC or D. The formulation is optimized with varied rations of peptide to DC or D. The structure of peptide-nanoparticle is illustrated in FIGS. 4 and 5. The resulting peptide-nanoparticle has mean sizes between 100-200 nm and with a positive charge of +50 mV as determined by a N4 Plus Submicron Particle Sizer the N4 particle size analyzer and a Delsa 440SX Zeta Potential Analyzer (Beckman Coulter, Inc., Fullerton, Calif., USA), respectively.

Labeling of Peptide with Fluorescence Dye: A protein-fluorescence labeling kit (Molecular Probe, Eugene, Oreg.) was used to label peptide with an Alex Fluor 555 (Cy3-NHS ester, orange-red) fluorescence dye according to the manufactures instruction. The Cy3-labeled peptide is used to monitor cellular uptakes and bio-distributions of peptide-nanoparticles by fluorescence imaging analysis in vitro and in vivo. Briefly, about 500 mg of peptide were dissolved in 100 ml of 0.1 M Sodium Bicarbonate (pH 8.3) buffer (a final concentration of 5 mg peptide/ml). Dissolve Cy3-succinimidyl ester (Cy3-NHS) in DMSO with a final concentration of 10 mg/ml. Mix 100 ml of peptide solution with 10 ml of Cy3-NHS solution and incubate the mixture at room temperature for 1 hour (or at 4° C. overnight) with rotation. The conjugated products were purified by running through a Sephadex G-25 column and efficiency of Labeling was determined by measuring OD at 280 nm and 555 nm OD and calculated using the equation described by the manufacture.

Conjugation of peptide with super-paramagnetic iron oxide (SPIO) nanoparticle: The inventors also conjugated the peptide directly with dextran-coated SPIO nanoparticle (SP) using a NHS ester-amine reaction and the SP-nanoparticles were then encapsulated with DC.

Synthesis of FP-hydrazone derivative: The carboxylic acid group at the C-terminal of FP is activated by 1-ethyl-3-(3-dimethylaminopropyl)carbodiimide (EDC) hydrochloride (Sigma, St. Louis, Mo.) and is then reacted with 3-(2-pyridinyldithio)propanoic acid hydrazide (PPA) (ProChem, Inc., Rockford, Ill.) over a 3-day to obtain a yield of >90% FP-hydrazone derivative product according to a published method. The progress of the reaction is followed by HPLC using a Zorbax Rx C18 column (25 cm×4.6 mm), an isochratic gradient of 10 mM $(NH_4)(H_2PO_4)$ in $CH_3OH$—$H_2O$ (7:3) at pH 4.7, and a flow-rate of 1 ml/min. FP-hydrazone, free FP and hydrazide are detected by UV (280 nm). Aldrich.

Conjugation of FP and SPIO: FP is conjugated to the FP through a two-step procedure using a heterobifunctional linker. First, the dextran-coated SPIO particles Feridex I.V. or Combidex (Advanced Magnetics Inc., Cambridge, Mass.) or Endorem (Guerbet, Aulnaysous-Bois, France) can be derivatized by crosslinking with epichlorohydrin and then reacted with ammonia to generate amino groups on the dextran coating and then modified with SMCC to provide a maleimide moiety (SPIO-SMCC). Second, the FP derivative is conjugated to the SPIO-SMCC by reaction of the maleimide group in SPIO-SMCC with the thiol group of the FP derivative that is obtained after reduction of its disulfide by TCEP. The ratio of the resulting FP-SPIO conjugation is determined by UV-visible spectrophotometry and further purified by size exclusion chromatography with a G-25 gel filtration column. The purified conjugate is concentrated and stored at −20° C. till further use. Drug derivatives will be conjugated to SPIO with a similar chemistry. For fluorescence labeling of the SPIO, the primary amines of above SPIO dextran derivatives are coupled with a DTPA isothiocyanate chelator (I-24221, Molecular Probes) to introduce a high-affinity binding site for a variety of metal ions, and then labeled with Fluo-3 potassium (Orange-red) (F-3715, Molecular Probes). The fluorescence-labeled FP-SPIO nanoparticles can be used for monitoring cellular uptake, intracellular trafficking, and biodistribution in vitro and in vivo by a confocal fluorescence imaging or FACS analysis.

The DC-SP-nanoparticle (DC-SPN) is used for systemic delivery of therapeutic peptides and for non-invasive imaging by MR with the SPIO as a MR contrast agent in vivo (FIG. 5.).

3. Inhibition of Tumor Cell Growth by Fus1-Derived Peptides and Gleevec in NSCLC and SCLC Cells Cell Lines. The inventors have a collection of NSCLN and SCLC cell lines with varied sensitivities to various chemotherapeutic drugs such as CDDP, Taxol, Gemcitabline, Gefitinib, Gleevec, and other PTK inhibitors. These cell lines were either clinically originated with natural drug-sensitive or resistant characters or established by selecting against a particular drug from a sensitive parent line. Characters like the $IC_{50}$ values for each drug, the genetic and expressional status of key TSGs such as 3p21.3 genes and p53 and oncogenic PTKs such as EGFR as well as the in vivo (in mice) tumorigenicity in these cell lines have been determined. For evaluation of the combined effects of FUS1 or FP with PTK inhibitors including Gefitinib (AstraZeneca) for blocking of EGFR and LY294002 (ComChem) for inhibition of PI3K/Akt on tumor cell growth and apoptosis, four human Gefitinib-resistant NSCLC cell lines H1299, H460, H358, and A549, and two Gefitinib-sensitive NSCLC lines HCC827 (with a gain of function mutation of EGFR) and H1817 (with an activating amplification of EGFR) will be used in vitro. Human SCLC cell lines gleevec-sensitive H69 and H128, and gleevec-resistant H69R and N417, are used to evaluate treatment with Fus1 peptide, FP-nanoparticles alone or in combination with gleevec and other small molecule chemotherapeutic drugs.

Figure 6:
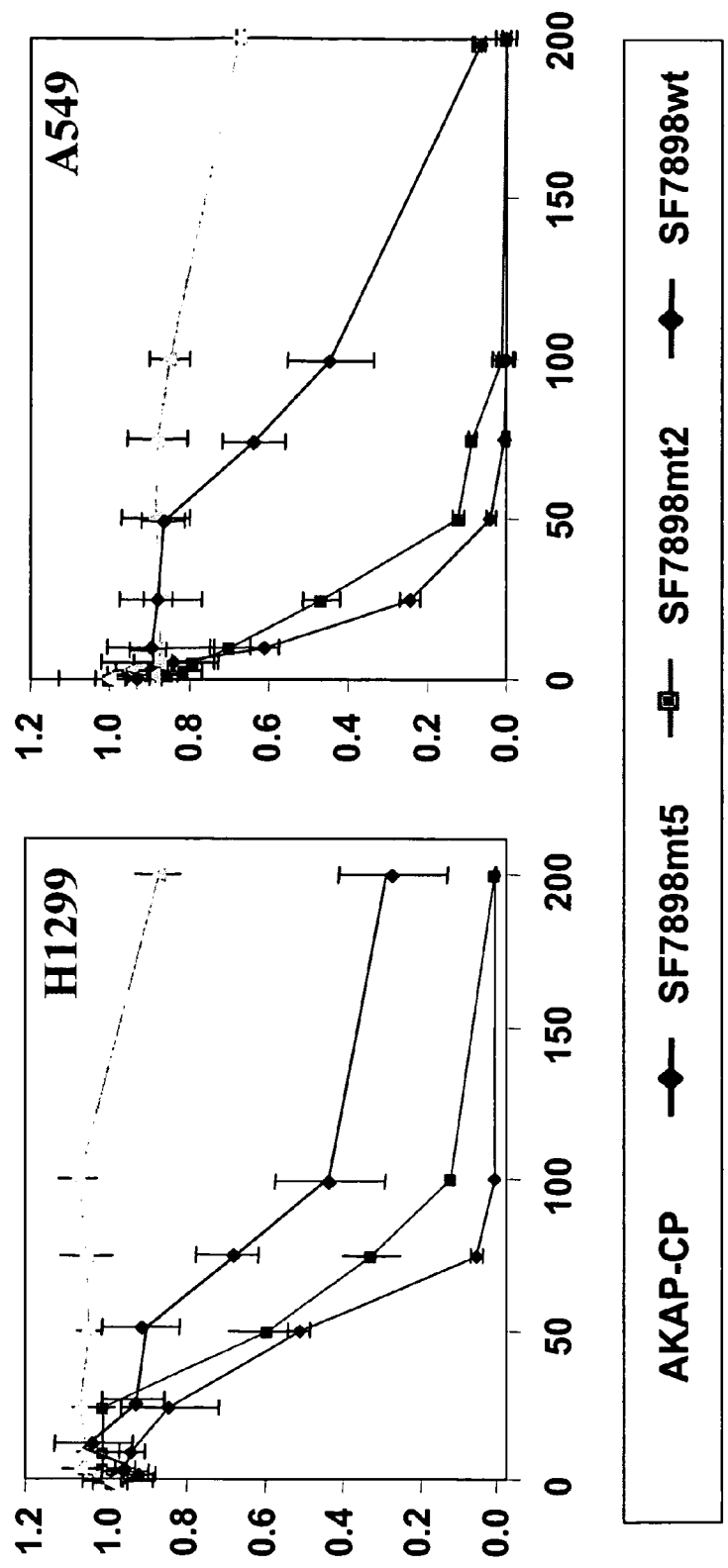
FIG. 6: The effects of Fus1 peptide on cell growth.
Figure 7:
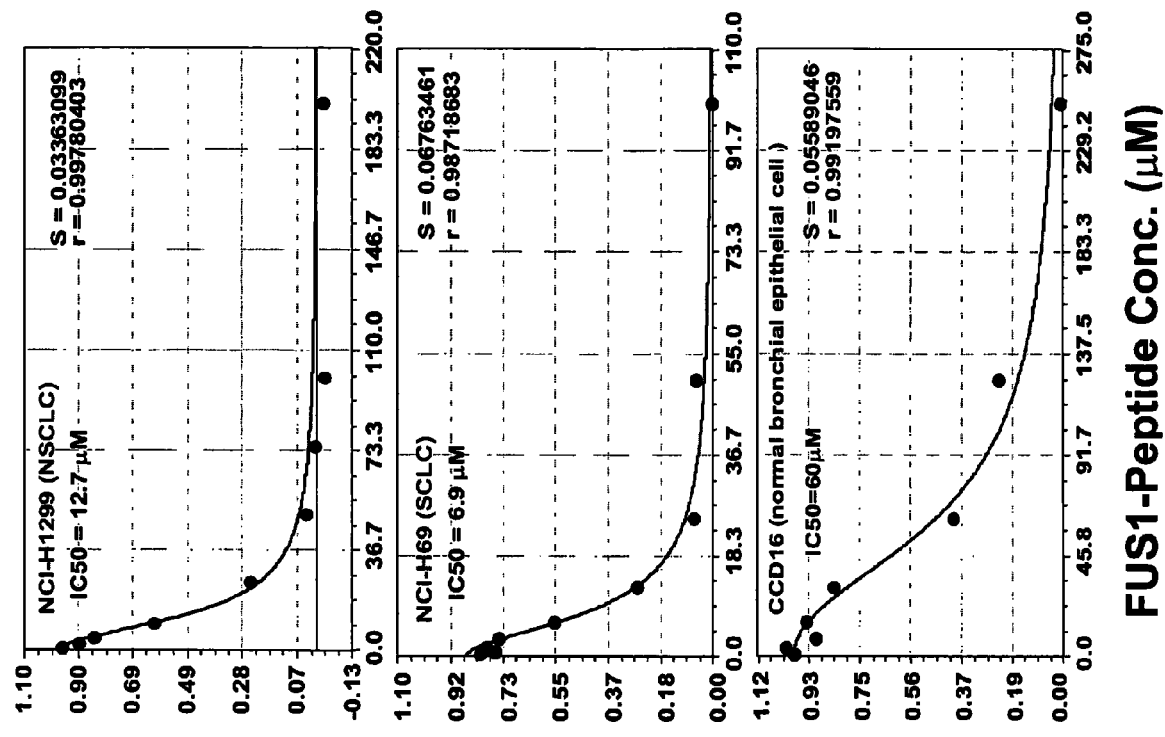
FIG. 7: IC50 values of Fus1 peptide in cells.
Figure 8:
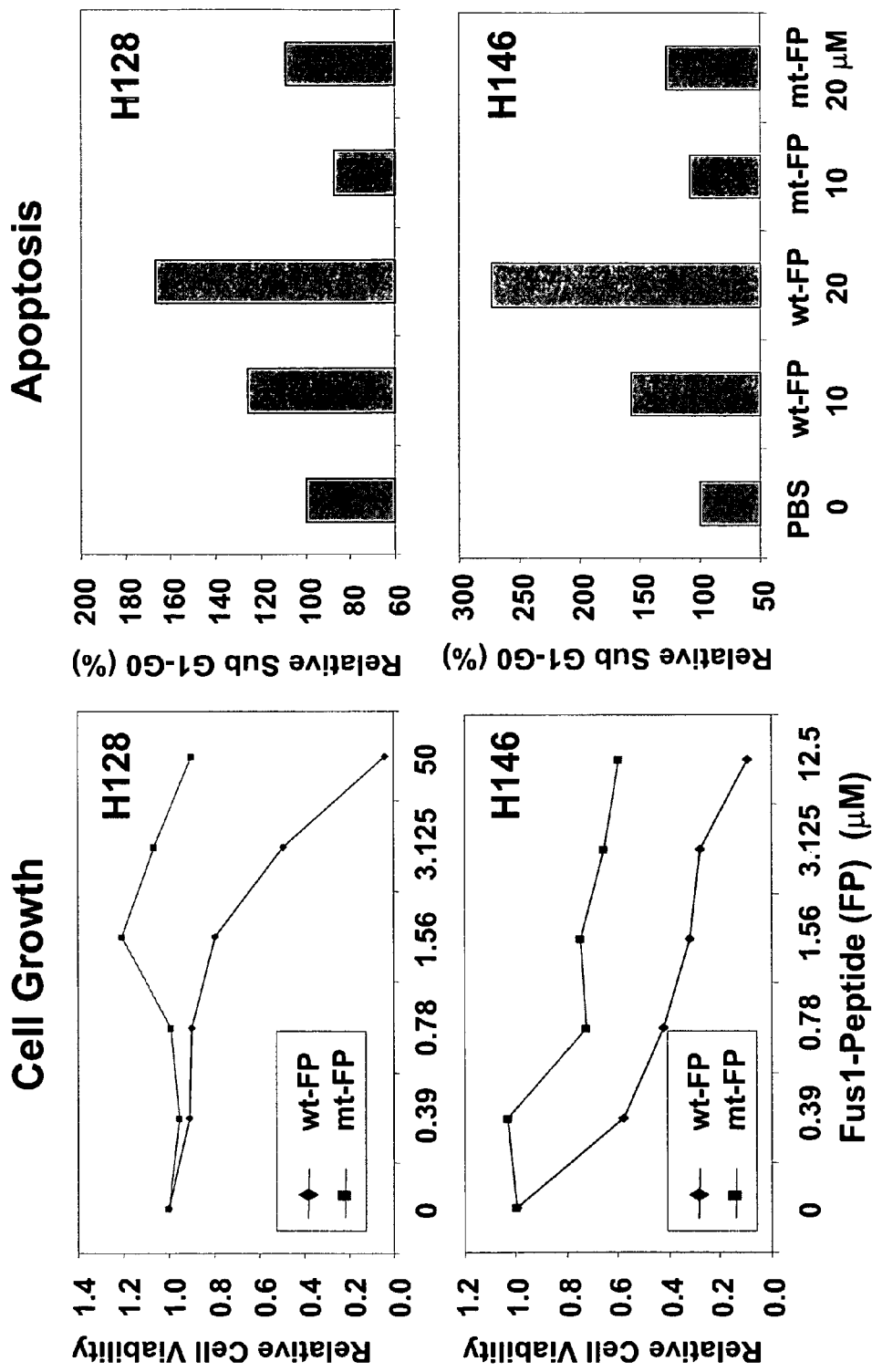
FIG. 8: The effects of Fus1 peptide on cell growth and apoptosis.

Inhibition of Tumor Cell Growth by treatment with wt-FP. To evaluate biological activity of wt-FP, the inventors analyzed the effect of wt-FP on tumor cell growth by direct application of the stearate-wt-FP by a XTT assay. The inventors found that the wt-FP exhibited a significant inhibitory effect on growth of NSCLC H1299 and A549 cells (FIG. 6), compared to cells treated with functional mutant Fus1 peptides mt-FP2 and mt-FP5, and non-specific control peptide (NSP) (FIG. 6). The inventors also determined $IC_{50}$ values of st-wt-FP in NSCLC H1299 (IC50=12.7 μM) and A549 (IC50=6.9 μM) cells as well as in normal bronchial epithelial CCD16 (IC50=60 μM) cells that could grow without supplemental of growth factors (FIG. 7). No significant cytotoxicity was observed in normal cells treated with st-wt-FP at the $IC_{80}$ doses to all other NSCLC cells, suggesting the tumor cell selectivity of the therapeutic FP. Similarly, a marked inhibition on tumor cell growth (FIGS. 8A and B) and an enhanced induction of apoptosis (FIGS. 8C and D) have also been observed in the wt-FP-treated SCLC H128 (FIGS. 8A and C) and H146 cells (FIGS. 8B and D), compared to either the mt-FP-treated or the untreated cell controls. These preliminary results demonstrate the potential of using the wt-FP as an anti-tumor therapeutic agent for lung cancer.

Enhanced inhibitory effects on tumor cell growth by a combination treatment of wt-FP with small molecule drug PTK inhibitors. The combined effects with various combinations of either the FUS1-nanoparticle or Fus1-peptide plus PTK inhibitors were analyzed quantitatively and statistically in vitro using isobologram modeling and statistical methods developed in our laboratory. The interactions between Fus1 and PTK inhibitors can be characterized in terms of synergistic, additive, and antagonistic effects. The cells can be transfected with hTMC-FUS1-nanoparticles at a fixed dose presuming the maximum transfection efficiency or treated with varied concentrations of FP and combined with varied doses of PTK inhibitors. The effects on cell growth were determined by a XTT assay at predetermined time points. The effects of the combined therapeutic agents on tumor cell growth were analyzed quantitatively and statistically by plotting the observed experimental data onto the corresponding isobolograms. Wilcoxon's signed-ranks tests were performed to compare the mean values of the observed data with the predicted minimum or maximum values for the additivity. If the mean value of the observed data was equal to or smaller than the predicted maximum value but equal to or larger than the predicted minimum value, the combination's effect was considered additive. If the mean value of the observed data was smaller than the predicted minimum value, the combination's effect was considered synergistic; if larger than the predicted maximum value, antagonistic, $P \leq 0.05$ was considered significant. All statistical analyses were performed using Statistica software (StatSoft Inc., Tulsa, Okla.). Findings from these in vitro experiments would provide us a statistically-tested quantitative validations of synergisms imposed by the FUS1 and PTK inhibitor combination treatments and serve as a data base for guiding the combination treatment designs in our preclinical and clinical trials.

Figure 9:
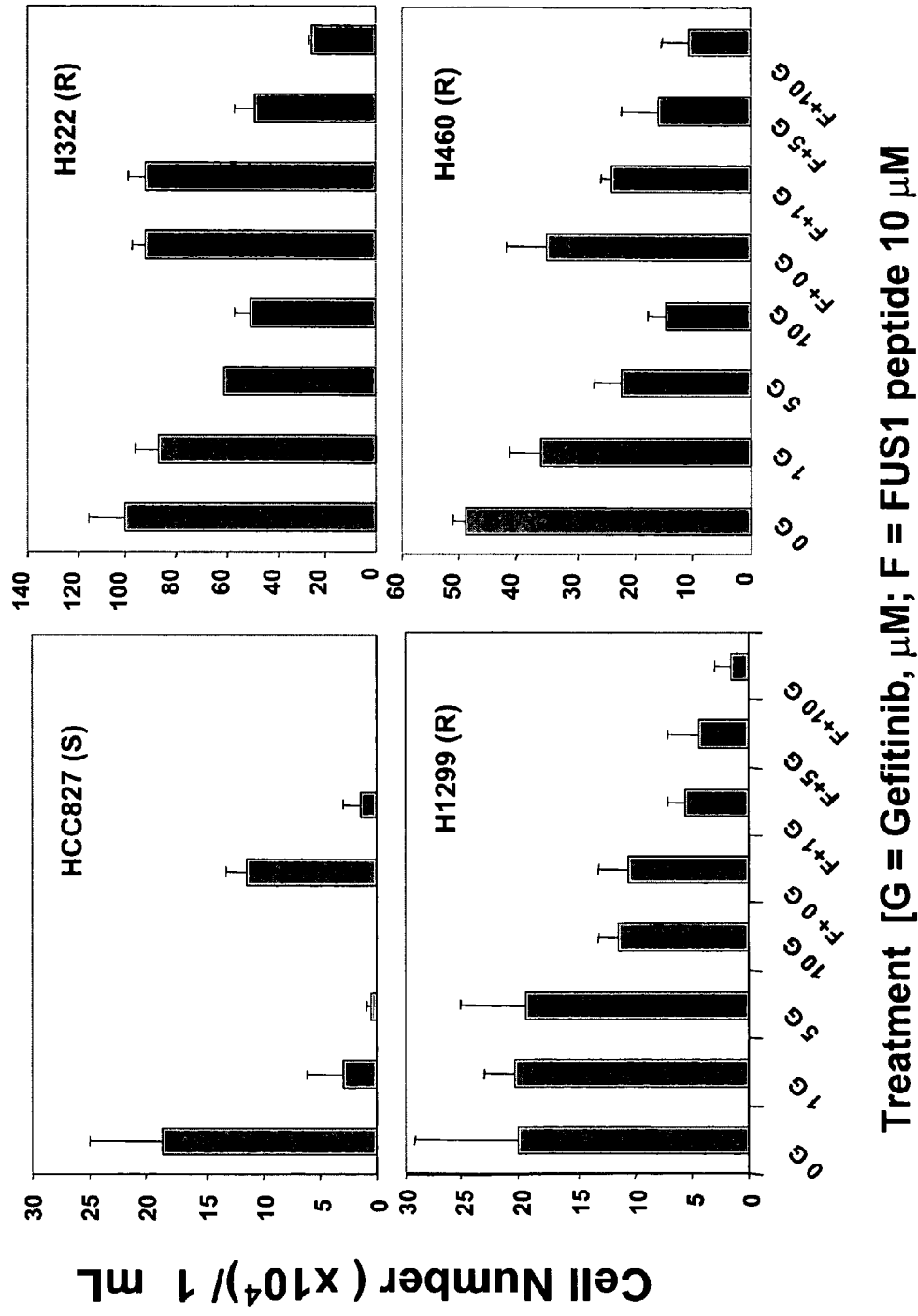
FIG. 9: The effects of combination treatment of Fus1 peptide and Gefitinib.

To explore the capability of the wt-FUS1 gene product or derived FUS1 peptide as a modulator of chemotherapeutic drugs for enhancing chemotherapeutic potency and overcoming drug resistance in lung cancer cells, the inventors evaluated effects of a combination treatment with wt-FP+Gefitinib on tumor cell growth in Gefitinib-sensitive and resistant NSCLC cells. The inventors found that re-activation of wt-FP in 3p-deficeint and Gefitinib-resistant NSCLC H1299, H358, and H460 cells significantly sensitized these cells's response to Gefitinib treatment, as demonstrated by a more than additive inhibitory effect on tumor cell growth (FIG. 9A). A marked inhibition on EGFR expression was also detected in wt-FP and Gefitinib co-treated H322 and H460 cells, as demonstrated by Western-blot analysis (FIG. 9B). These preliminary results suggest that the wt-FP may play a critical role in modulating the sensitivity of tumor cells to the chemotherapeutic agents, such as to DNA damaging agent cisplatin and PTK EGFR inhibitor Gefitinib and that a combination treatment of the FUS1-nanoparticle-mediated molecular therapy with these small molecule chemotherapeutics may be an efficient treatment strategy for lung cancer.

Figure 10:
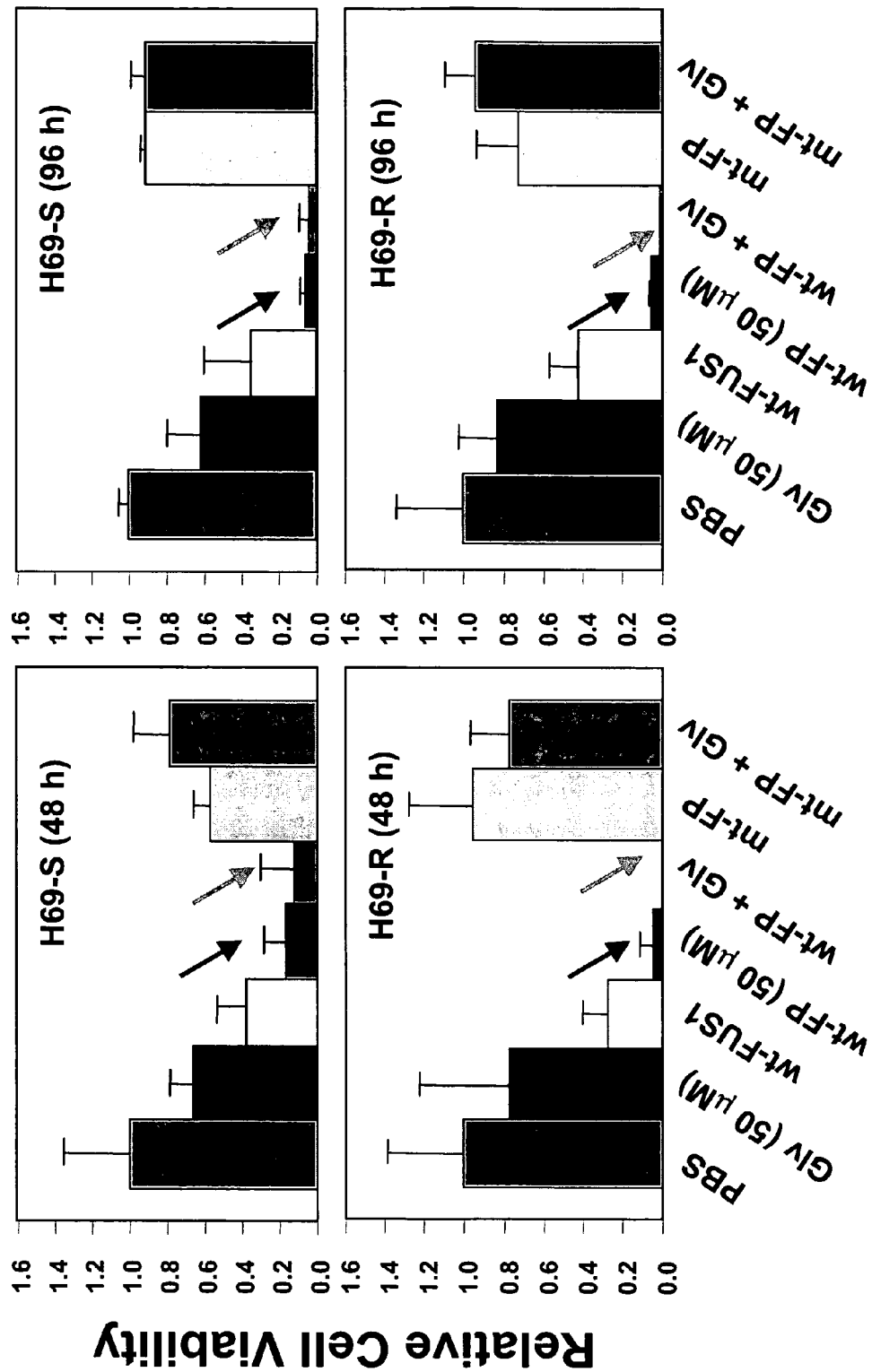
FIG. 10: The effects of Fus1 peptie on Gleevec-sensitive and Gleevec-resistant cells.

Furthermore, the inventors also detected an enhanced sensitivity of the SCLC Gleevec-sensitive H69-S (FIG. 10) and Gleevec-resistant H69-R (FIG. 10) cells to the treatment with Gleevec when co-treated with wt-FP for 48 h and 96 h, respectively, compared to either treatment alone or in combination with nonspecific peptide (NSP) or mt-FP controls (FIG. 10). These preliminary findings suggest that one of the activities of the Fus1 tumor suppressor protein may be to interfere with PTK function. A combination treatment of PTK inhibitor Gleveec plus FUS1-nanoparticles or Fus1-derived peptides may be a useful strategy for enhancing anti-cancer efficacy of Gleveec and overcoming Gleveec-resistance in lung cancer.

4. Inhibition of PTK Activities by Fus1-Peptide in NSCLC and SCLC Cells.

Protein Tyrosine Kinases (PTKs) perform a critical role in signal transduction pathways that control cell proliferation, differentiation, metabolism and apoptosis. Phosphorylation of proteins by PTKs is essential for the regulation of these biological mechanisms and defects in these pathways may result in a number of human diseases, including cancer. The important aspect of these enzymes in cellular regulation is accentuated by the fact that for a large number of kinases a corresponding viral oncogene product has been identified. Protein tyrosine kinase activity is often associated with membrane receptor protein tyrosine kinases (e.g. EGF-, PDGF-, CFS-, IGF-1 and insulin receptor) and soluble non-receptor tyrosine kinases (e.g. p60c-Src, yes, lck, lyn, fyn). Assaying of PTK activity allows for characterization of protein tyrosine kinases, elucidation of their biological functions as well as aiding in development of specific PTK inhibitors.

Figure 11:
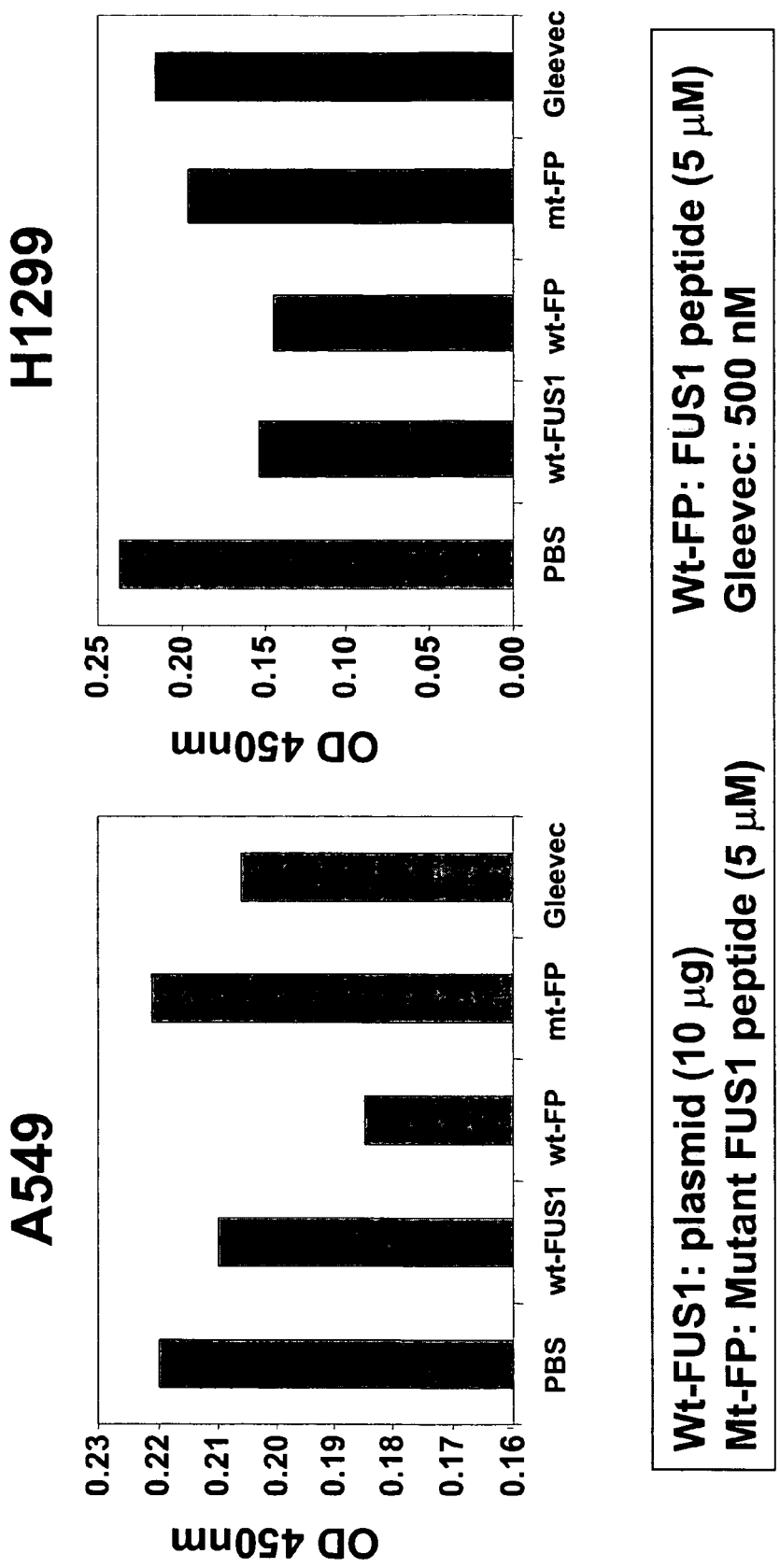
FIG. 11: The effect of Fus1 peptide on c-Abl activity in cells.

The inventors analyzed c-Abl tyrosin kinase activity in FP-treated NSCLC H1299 and A549 cells using a Tyrosine Kinase Activity Assay kit (CHEMICON, Temecula, Calif.) according to manufacturer's instruction. Briefly, $1 \times 10^7$ NSCLC H1299 or A549 cells were treated with 5 µM of wt-FP or mut-FP for 6 hr, or transfected with 10 µg of wt-FUS1 expressing plasmid DNA-DOTAP nanoparticle for 24 hr. Cell lysates were prepared in RIPA buffer containing 50 mM Tris-HCl (pH 8.0), 150 mM sodium chloride, 1% (w/v) sodium deoxycholate, 1 mM DTT, 1% (v/v) NP-40, 0.1% (w/v) SDS, and complete protease inhibitors (Roche). One mg of protein lysate was used to perform immunoprecipitation (IP) with a mouse anti-c-Abl antibody (BD Bioscience Pharmingen, San Diego, Calif.) protein. The immuno-precipitated complex was resuspended in 50 µl of PTK assay buffer containing 5 mM ATP, 50 mM $MgCl_2$ in TBS (25 mM Tris, 0.15 M NaCl) pH 7.2, 1 mM DTT, 0.01% of thimerosal, and complete protease inhibitors. The c-Abl IP complex was then incubated with a synthetic biotinylated substrate, poly [Glu:Tyr, 4:1], which contains multiple tyrosine residues and can be phosphorylated by a wide range of PTKs, for 45 min at 30° C. The reaction was stopped by addition of 500 mM EDTA. The phosphorylated and dephosphorylated substrates are immobilized by binding to the streptavidin-coated plate. The fraction of phosphorylated substrate was visualized using a phosphotyrosine monoclonal antibody conjugated to HRP and an ensuing chromagenic substrate reaction. The quantity of phosphate incorporated into the tyrosine kinase substrate was determined utilizing the phosphopeptide standard curve. A marked inhibition of c-Abl activity was detected in A549 cell, which showed a high level of expression of activated (phosphorylated) c-Abl protein (data not shown), by treatment with wt-FP or transfected with wt-FUS1-nanoparticle, compared to those untreated control or treated with mut-FP or Gleevec (FIG. 11). Activity of c-Abl protein was also inhibited by treatment with wt-FP in H1299, which has a lower level of expression of c-Abl protein than that in A549 cells.

Figure 12:
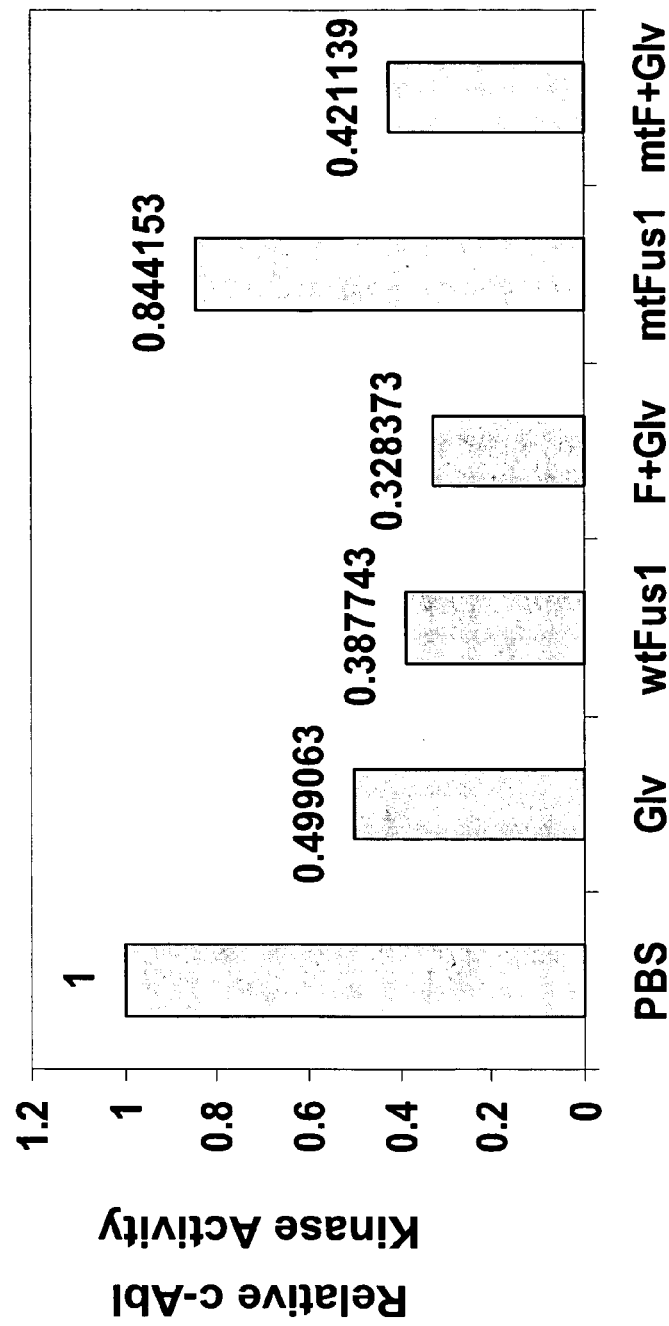
FIG. 12: The relative activity of c-Abl in peptide treated cells.
Figure 13:
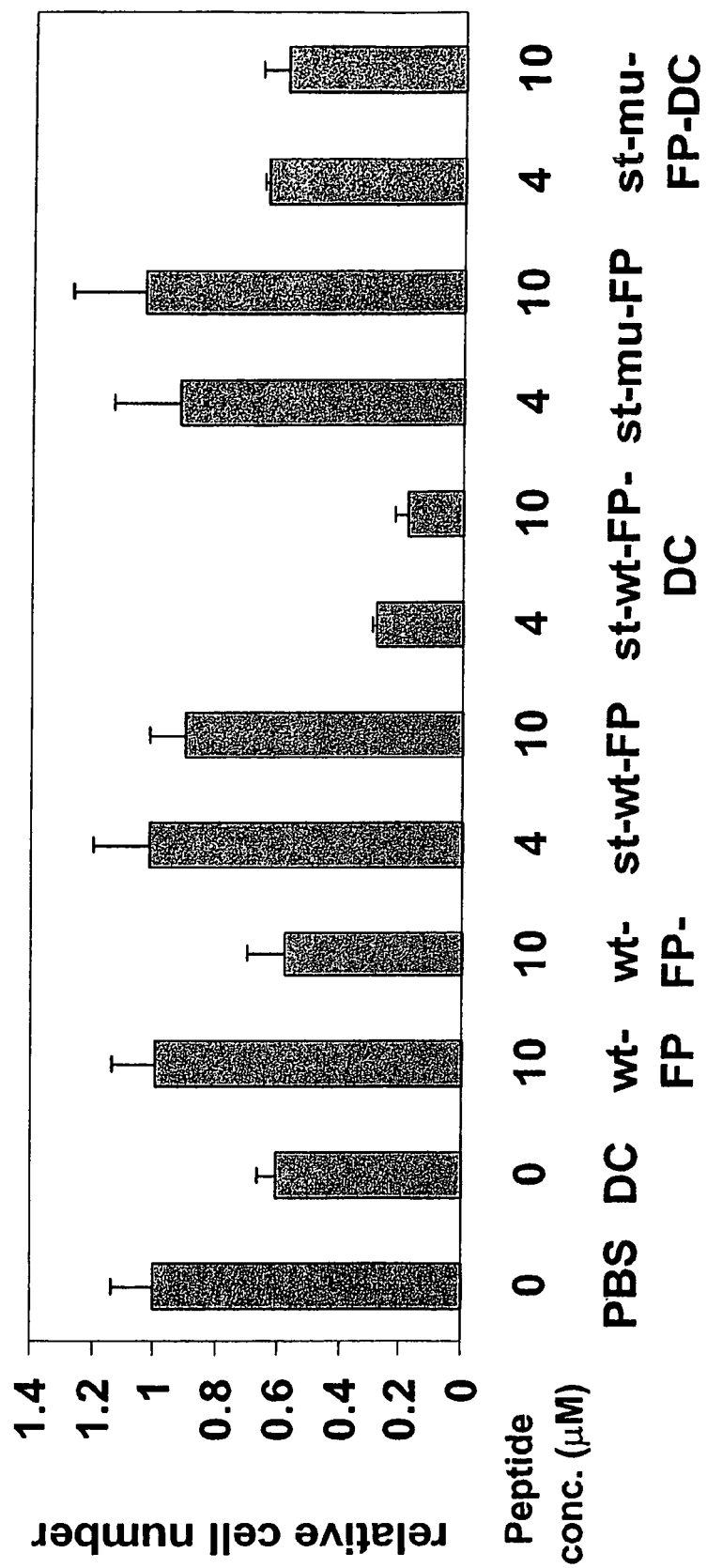
FIG. 13: The inhibition of tumor cell growth by Fus1 peptide-nanoparticle complexes.

Similarly, the inventors also observed that both treatments by the wt-FP peptide and by exogenous expression of wt-Fus1 protein strongly inhibited the c-abl tyrosine kinase activity, as measured by tyrosine phosphorylation of an optimum tyrosine kinase peptide substrate using a mono-clonal anti-phopho-abl (Tyr-323-p) antibody in SCLC N417 (FIG. 12). In addition, the inhibitory effects of the wt-FP on activities of several PTKs including c-abl and c-kit were also detected in SCLC N417 and H69 cells treated either with the wt-FP alone or in combination with Gleevec (wt-FP+G) for 48 h, as shown by an analysis using immuno-precipitation (IP) with anti-c-abl or anti-c-kit antibodies and immuno-blot (IB) with anti-phospho-Tyr (pY20) antibody.

Furthermore, a marked inhibition of phosphorylated EGFR, ERK and Akt proteins was also detected in cells treated by FUS1-nanoparticle or wt-FP alone or in combination with gefitinib in both Gefitinib-sensitive NCC827 and H1819 cells, as demonstrated by Western-blot analysis with phospho-EGFR, ERK or Akt-specific antibodies. However, no effect were detected on the level of the total PTK proteins, suggesting that FP specifically inhibit the activated oncogenic TPKs and leading to inhibition of tumor cell proliferation and apoptosis in these cells with highly activated PTK activities due to mutation or abnormal amplification of EGFRs.

5. Enhanced Cellular Uptakes of Peptide-Nanoparticle In Vitro.

The inventors compared the cellular uptakes of un-complexed peptide with peptide-nanoparticle by fluorescence imaging analysis, using Cy3-fluor labeled peptide in NSCLC h1299 cells. A week cell uptakes (faint fluorescence) were observed in st-P-treated cells but not in non-stearate peptide-treated cells. A dramatically enhanced cellular uptakes were observed in both peptide- and stearate-peptide(st-p)-nanoparticle treated cells compared to those treated with uncomplexed peptide at the same concentration of peptide, indicating the high efficiency of cell uptakes mediated by peptide-nanoparticle.

6. Inhibition of Tumor Cell Growth by Treatment with FP-Nanoparticle in H1299 Cells.

The inventors used Fus1 peptide (FP)-nanoparticle to evaluate its effect on tumor cell growth in NSCLC H1299 cells. A significant inhibition of tumor cell growth were observed in FP-nanoparticle-treated cells compared to those treated with controls. A significantly enhanced inhibition of tumor cell growth also detected in FP-nanoparticle-treated cells compared to those treated with FP at a lower dose of peptide (at a $IC_{20}$ level of FP).

7. Induction of Apoptosis by Treatment with FP-Nanoparticle In Vitro.

Figure 14:
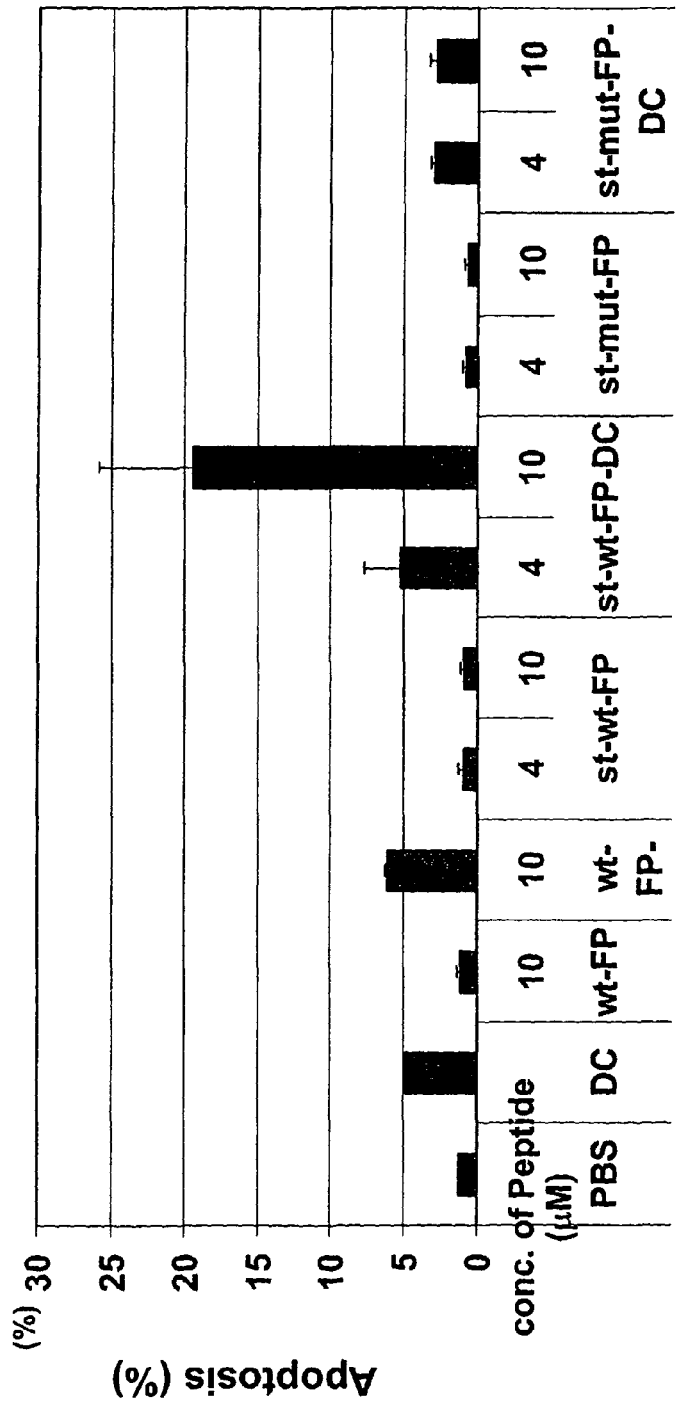
FIG. 14: The induction of apoptosis in cells treated with Fus1 peptide-nanoparticle complexes.
Figure 15:
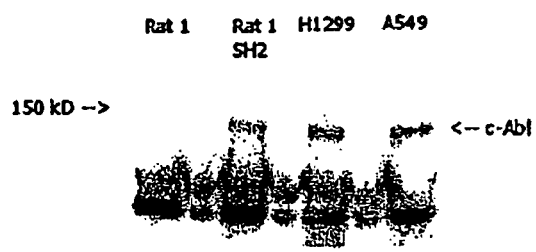
FIG. 15: Tyrosine phosporylation in different cell lines.
Figure 16:
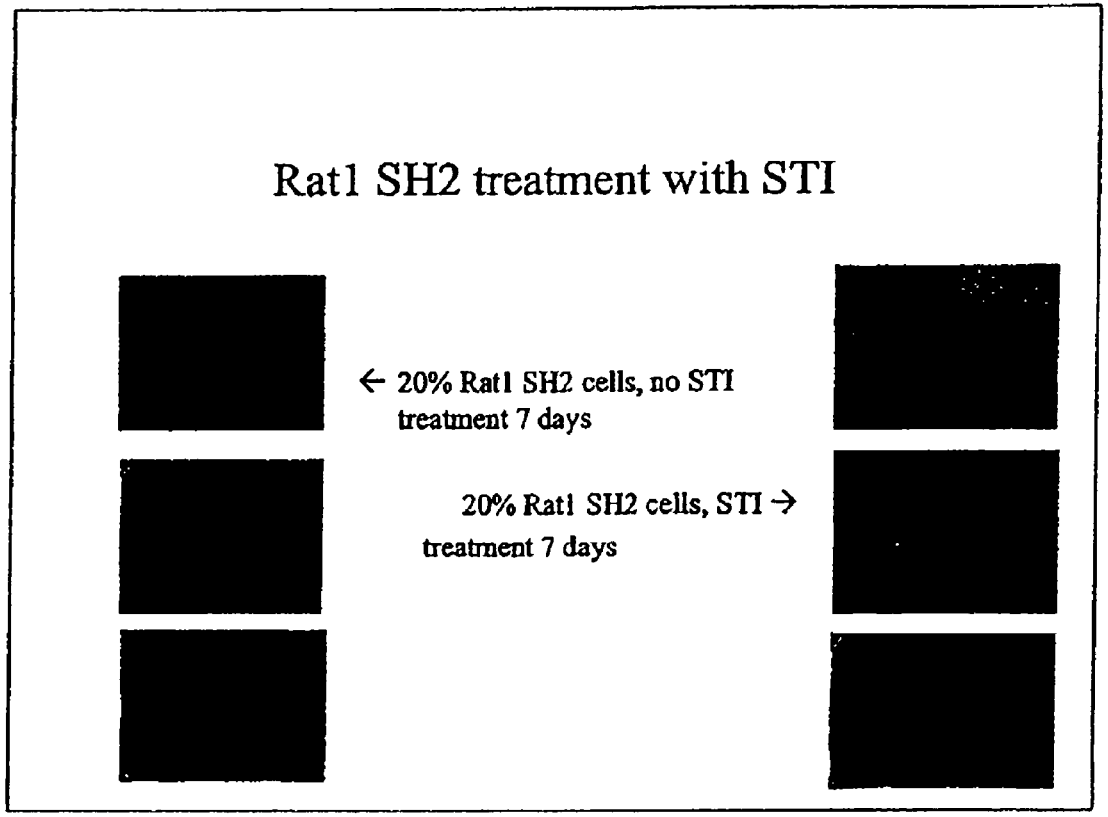
FIG. 16: Results of treating Rat-1 SH2 cells with STI (imatinib mesylate; also known as STI-571 or Gleevec).
Figure 17:
FIG. 17: Results of reating Rat-1 SH2 cells with stearated Fus1 peptide.
Figure 18:
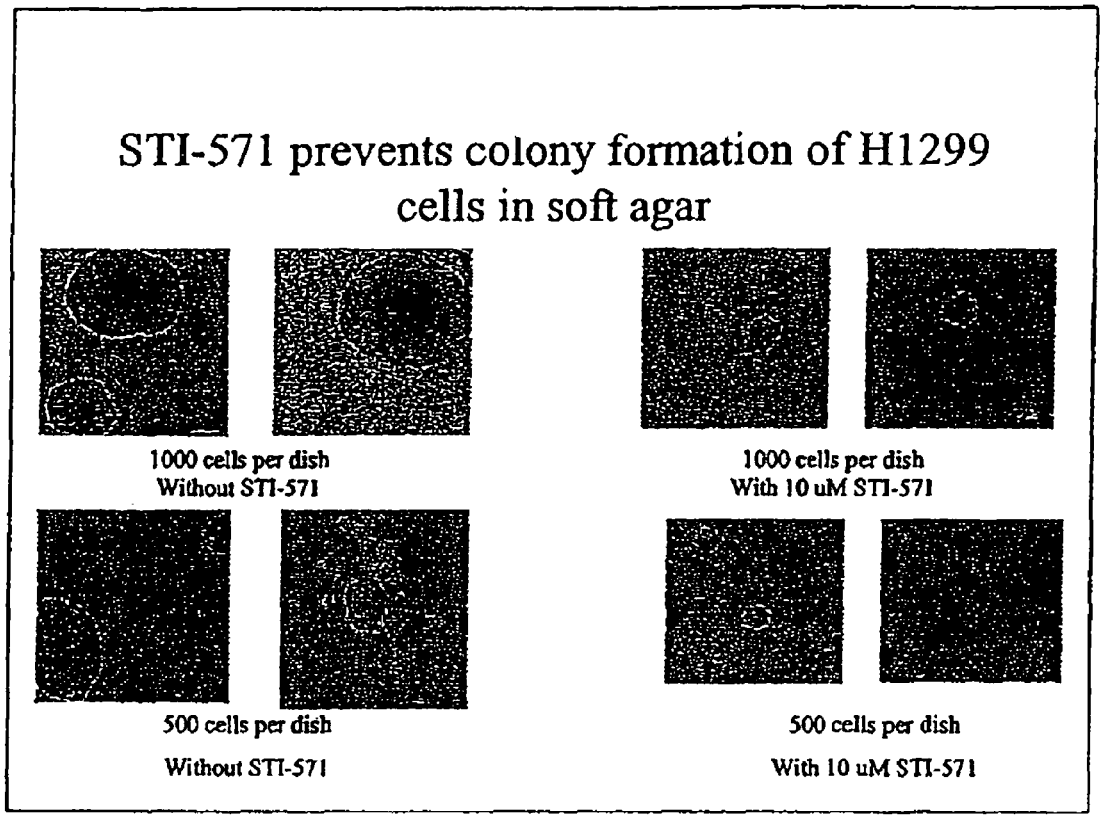
FIG. 18: The results of treating cells with STI-571 in soft agar.
Figure 19:
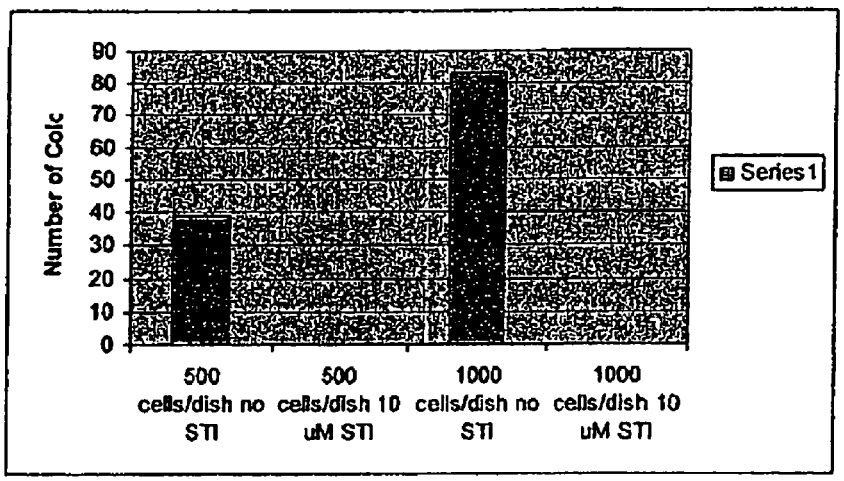
FIG. 19: The results of treating cells with STI-571 in soft agar.

The inventors evaluated the induction of apoptosis by treatment with either FP alone or FP-nanoparticle in H1299 cells by fluorescence imaging and FACS analysis using an in situ apoptosis analysis with TUNEL reaction. A significant induction of apoptosis was detected in cells treated with FP-nanoparticles compared to those treated with nonspecific and mt-FP-nanoparticle controls (FIG. 14). Induction of apoptosis in FP-nanoparticle-treated H1299 cells was observed by fluorescence imaging analysis with in situ TUNEL staining (2 µM peptide, 72 hr). These results clearly demonstrate the biological effectiveness of FP-nanoparticles in vitro. Experiments for evaluation of cellular uptakes and therapeutic efficacy of FP-nanoparticle by systemic administration are going in human tumor-bearing mice.

8. Encapsulation of Therapeutic Genes and Peptides in DC-Nanoparticle.

The inventors encapsulated both therapeutic or reporter gene expressing plasmid DNAs and peptide in DC or D nanoparticle to explore the possibility and potential of using a single nanopaticle to delivery multiple therapeutic agents. The inventors encapsulated both GFP expressing pDNA and Cy3-labeled FP peptide, termed GFP-FP-nanoparticle. Both GFP expression (Green fluorescence) and peptide uptakes (Orange-red) could be detected simultaneously in the same cells, indicating that both DNA and peptide were effectively delivered by the single nanoparticle. Cellular uptake of the GFP DNA/NSP peptide-nanoparticles in H1299 cells was measured at 2 hr and 24 hr (NSP final concentration=4 μM).

Example 2

FUS1 is a tumor suppressor gene involved in lung cancer. The inventors have found that a Fus1 peptide inhibits the c-Abl tyrosine kinase in vitro. Of interest, the inhibitory sequence was derived from a region that was deleted in one of the mutant Fus1 proteins detected in some lung cancer cell lines. Importantly, a stearic acid modified form of this peptide was required for the inhibition. This stearic acid-fus1 peptide also inhibited foci formation in fibroblasts oncogenically transformed by the activated c-Abl protein. These findings suggest that one of the activities of the Fus1 tumor suppressor protein is to interfere with c-Abl tyrosine kinase function.

Frequent loss of one allele of chromosome arm 3p in both small cell lung cancer (SCLC) and non-small cell lung cancer (NSCLC) provides strong evidence for the existence of tumor suppressor genes (TSGs) in this chromosome region. One of these candidate TSGs, FUS1, did not show homology with any known genes. It was found to have only few mutations in lung cancers, and was usually expressed at the mRNA level in lung cancers. Several NSCLCs had the same nonsense mutation, which arose from aberrant mRNA splicing. This aberrant form lacked sequences at the near the C-terminus of FUS1, which resulted in a truncated predicted protein of 82 amino acids compared to 110 amino acids for the wild-type protein (Kondo et al., 2001).

The c-Abl tyrosine kinase is ubiquitously expressed in all tissues. It becomes an oncogenic protein when it is fused to retrovirus Gag sequences and Bcr sequences (Ben-Neriah et al., 1986). The c-ABL gene encodes a tyrosine kinase. Part of the c-ABL gene was acquired by a replication-defective mouse retrovirus termed the Abelson leukemia virus. The tyrosine kinase activity of normal c-Abl is highly regulated with inhibitors being present in the nucleus (Wang, 2000) and the cytoplasm (Butturini et al., 1996). The c-Abl protein is found both in the nucleus and cytoplasm. Nuclear c-Abl function involves responses to DNA damage (Wang, 2000). Cytoplasmic function of c-Abl involves cell migration and cell adhesion functions. Importantly, activation of the cytoplasmic c-Abl proteins leads to oncogenic activity. For example, the Gag-Abl protein is a potent oncoprotein involved in causing leukemia in mice infected with Abelson leukemia virus. In addition, the Bcr-Abl oncoprotein is the causative factor in several human leukemias. Both Gag-Abl and Bcr-Abl have high levels of tyrosine kinase activity (Kloetzer et al., 1985).

However, c-ABL gene has not been implicated in other types of cancers. Of interest, over-expression of c-Crk, a major substrate of c-Abl, has been associated with an aggressive phenotype in lung adenocarcinomas (Miller et al., 2003). In another study, immunohistochemical analysis of c-Crk-ll show that the levels of c-Crk-ll were significantly elevated in lung and colon cancers (Nishihara et al., 2002). These findings are of interest in light of our findings that Fus1, a tumor suppressor protein, may down-regulate c-Abl. Together, these observations suggest that the c-Abl pathway may be activated in certain lung cancers.

Methods and Results

The c-Abl tyrosine kinase is inhibited by a Fus1 peptide. The inventors used a Fus1 peptide and observed in several assays that it strongly inhibited the Abl tyrosine kinase as measured by tyrosine phosphorylation of an optimum substrate. An in depth analysis indicated that the Fus1 peptide inhibited c-Abl in a dose-dependent manner. Fus-1 peptide inhibition of Crk phosphorylation by commercial Abl was observed; control groups included peptide, DMSO, and (DMSO+stearic acid). The IC50 was estimated to be 30 uM. This peptide has the sequence-Stearic acid-KLRRVHKN-LIPQGIVKLDHR (SEQ ID NO:11). The inventors found that that the stearic acid moiety was required for inhibition but stearic acid itself had no inhibitory effects. Non-stearate FUS1 peptide did not inhibit phosphorylation of Gst-Crk by commercial Abl.

A Fus1 peptide inhibits foci formation in Rat-1 cells transformed by c-Abl. The inventors tested the effects of this Fus1 peptide on foci formation using Rat-1 cells transformed with an activated c-Abl tyrosine kinase. The inventors found that the stearic acid-Fus-1 peptide blocked foci formation. Stearic acid had no effects. Interestingly, proliferation of ABL transformed cells was not inhibited by the FUS1 peptide, only the oncogenic activity leading to foci formation was inhibited.

Evidence that c-Abl is activated in a human lung cancer cell line. The inventors analyzed two lung cancer cell lines with alterations in the FUS1 gene, and analyzed them for evidence of activated c-Abl. In these experiments, the inventors performed immunoprecipitation with a monoclonal anti-Abl antibody that detects human Abl (p6D). This monoclonal antibody was prepared against a human Abl peptide encompassing amino acids 52-64 (Sun et al., 2001). The immunocomplexes were blotted with anti-phosphotyrosine, anti-Abl (8E9) and the p6D antibody. 32D P210 was used as a positive control, and CCD16 normal lung fibroblast was used as a negative control.NSCLC cells H1299 and A549 showed active c-Abl: The results showed that the A549 cell tine contained an activated Abl-related protein with a size of about 110 kDa. It was detected by blotting with two different sequence-specific ABL antibodies, anti-Abl 8E9 (specific for the SH2 domain) and the p6D anti-Abl monoclonal antibody. Of interest, this Abl-related protein is smaller in size than the authentic c-Abl protein (145 kDa). Importantly, this Abl-related protein was detected with anti-phosphotyrosine, indicating that it may be kinase active. The presence of a shortened form of c-Abl that contains sequences near the amino terminus (recognition by the p6D antibody) suggests that it might be truncated at the C-terminus. This may be important, as intact c-Abl is associated with actin filaments by way of C-terminal sequences (Woodring et al., 2003). In addition, actin filament associated c-Abl has reduced tyrosine kinase activity (Woodring et al., J2003), suggesting that actin filament binding inhibits the c-Abl tyrosine kinase. Therefore, removal of the C-terminus of c-Abl may be one way of activating c-Abl.

FIG. 27, FIG. 16, FIG. 17, FIG. 18 and FIG. 19 show results of other experiments.

Figure 20:
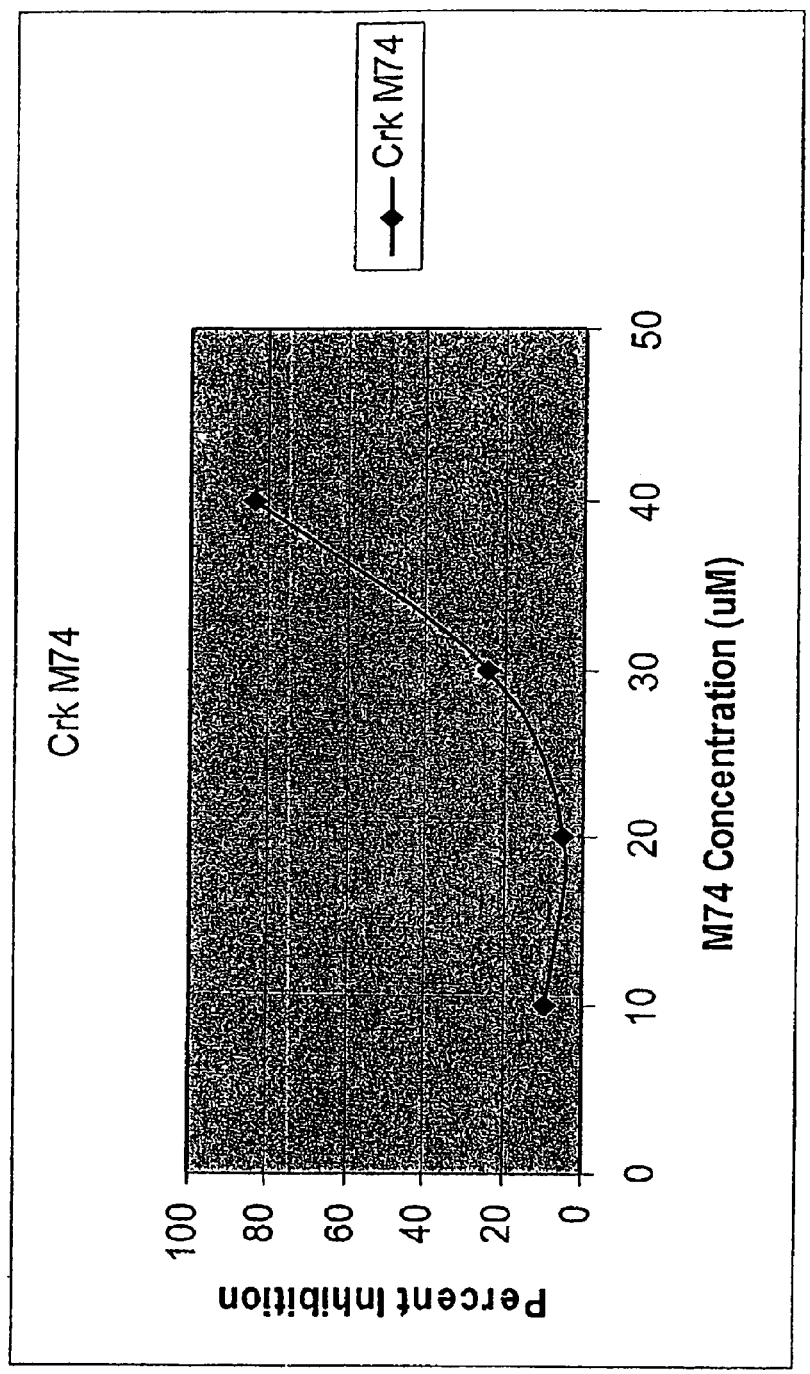
FIG. 20: Inhibition of phosphorylation by Fus 1 peptide.
Figure 21:
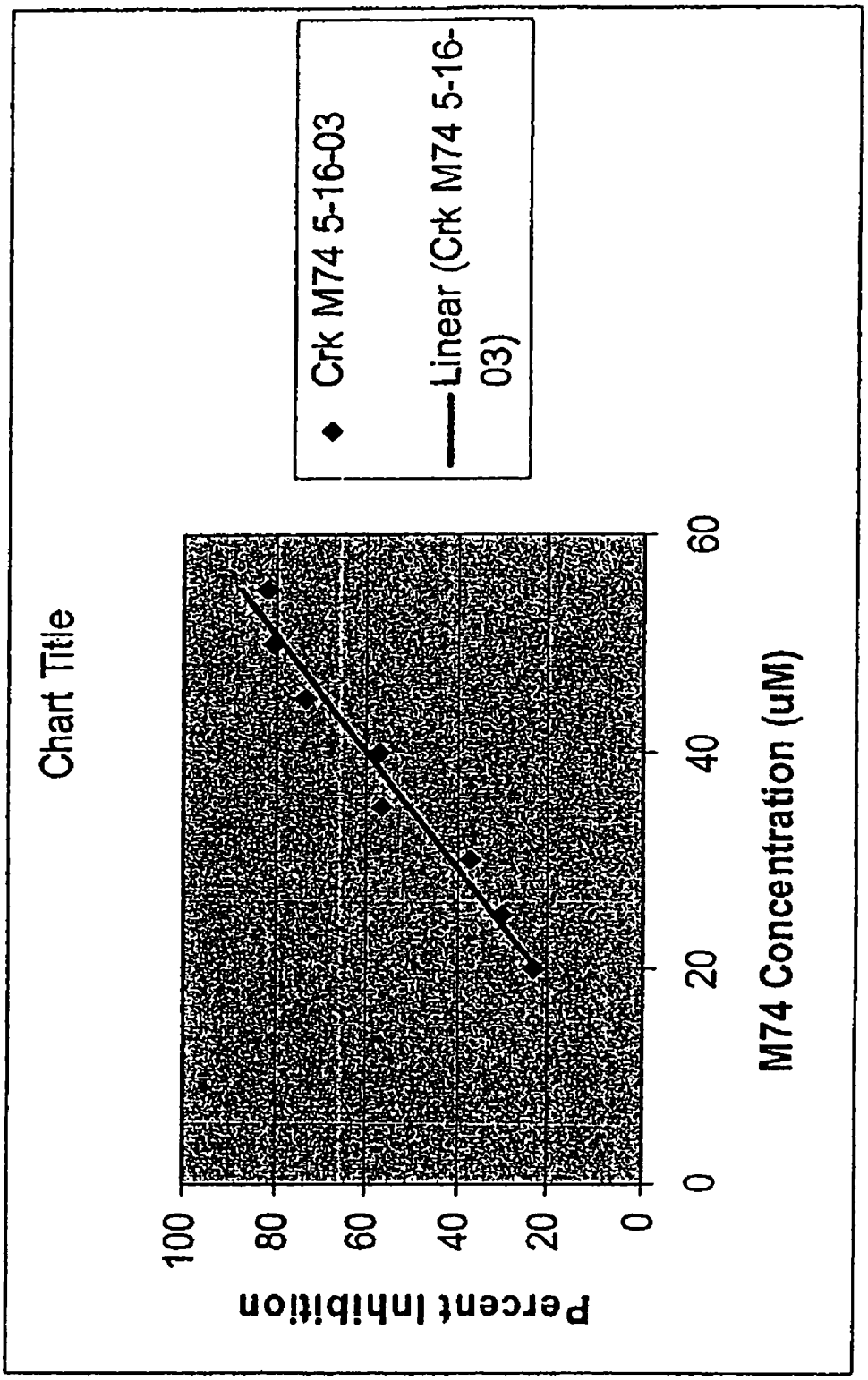
FIG. 21: Linear inhibition of c-Abl kinase by Fus1 peptide.
Figure 22:
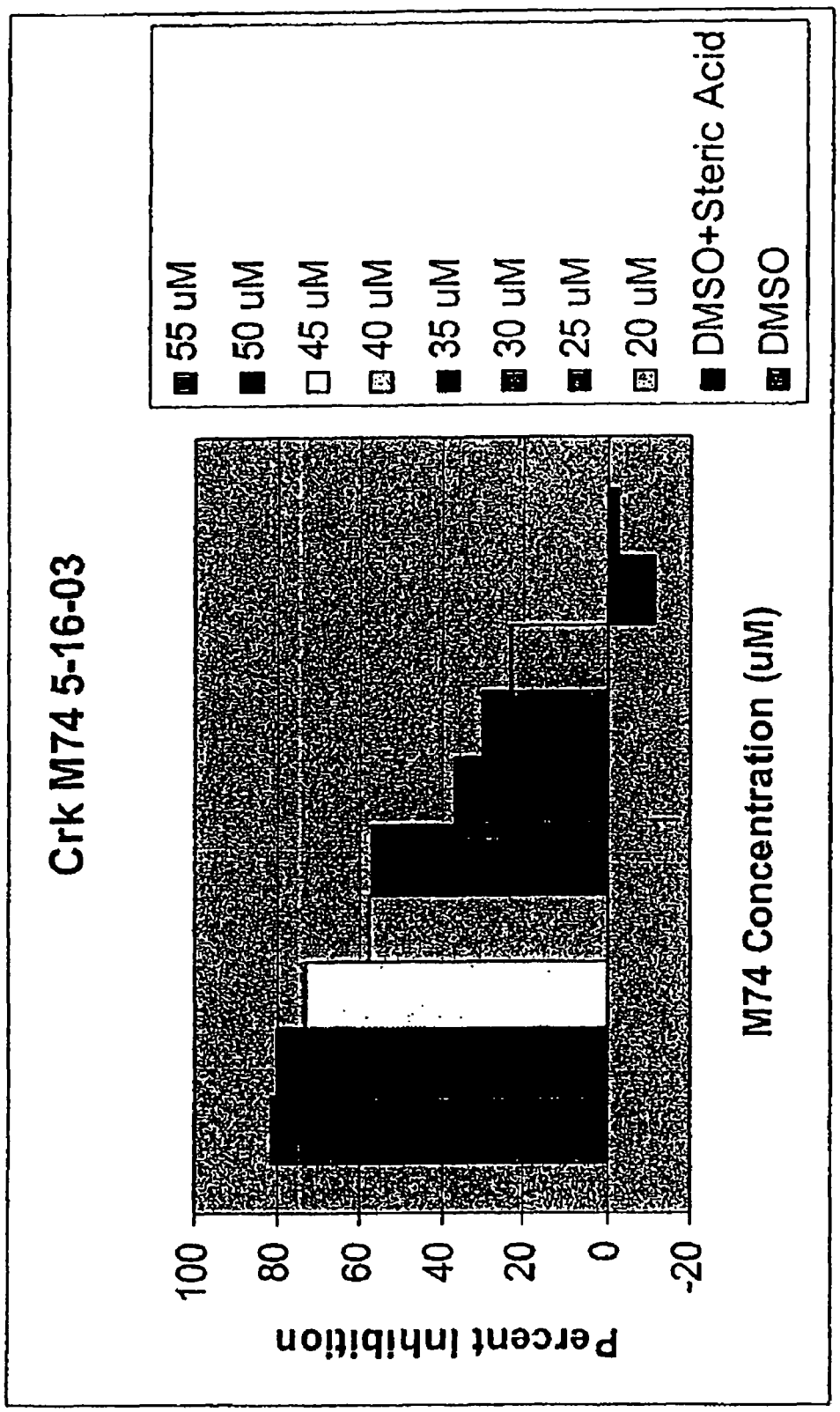
FIG. 22: No effect of c-Abl kinase by DMSO or stearic acid.

In other experiments demonstrating the inhibition of commercial c-Abl tyrosine kinase by the stearated Fus1 peptide KLRRVHKNLIPQGIVKLDHR (SEQ ID NO:11), the stearated Fus1 peptide was combined with truncated commercial (New England Bio-Labs) cAbl tyrosine kinase (45 kD) containing only the SH2 and SH1 domains, GST-CRK (Abl preferred substrate) and $^{32}$P-γATP. After 30 min of ncubation at 30° C., samples were boiled with 2×SDS sample buffer and run on an 8% SDS PAGE gel. The gel was dried and exposed to phosphoimager. Lane 1 was zero peptide control, and lanes 2-5 were 10, 20, 30, and 40 μM of peptide, respectively. FIG. 20 shows that the peptide inhibits c-Abl tyrosine phosphorylation of GST-CRK. The concentration dependent inhibition of c-Abl tyrosine kinase by the peptide was also observed. A zero peptide control, a DMSO control, a DMSO plus stearic acid control, and 20, 25, 30, 35, 40, 45, 50 and 55 µM of peptide were evaluated. FIG. 21 shows linear inhibition of c-Abl tyrosine kinase by the peptide. The curve represents inhibition of GST-CRK phosphorylation. FIG. 22 shows that DMSO and stearic acid do not affect the c-Abl tyrosine kinase activity.

In other experiments, the human lung cancer cell lines was shown to contain an Abl related tyrosine phophorylated protein. Rat-1, Rat1 SH2 (activated Abl tyrosine kinase), H1299 (p53 negative) and A549 (p53 positive) human lung cancer cell lines were lysed in deterent buffer. Anti-Abl P6D monoclonal antibody was used to immunoprecipitate Abl proteins. Protein A Sepharose beads were used to pull down the immune complexses. Proteins were eluted from the beads, then run on an SDS PAGE gel. After blotting and blocking, the membrane was treated with anti-Abl 8E0 (anti-Abl SH2 domain) antibody. Active Abl was observed in A549 cells using the 8E9 antibody, the 4G10 antibody and the P6D antibody. Immunoblotting was performed with anti-phosphotyrosine antibody (4G10). The membrane where the 8E9 antibody was stripped and re-probed with P6D anti-Abl antibody.

In further experiments, the effects of Fus1 peptide on foci formation induced by c-Abl was studied. Rat-1 SH2 cells were treated with the stearated Fus1 peptide after cells became confluent (10 µM Fus1 peptide with medium changed every 2 days until foci were observed). Rat-1 SH2 cells express GFP as a marker. A fluorescent photo was taken of green fluorescing Rat-1 SH2 cells treated with peptide. A phase contrast photo of the field was produced. A fluorescent photo of untreated Rat-2 SH2 cells was also produced, and a phase contrast photo was produced. (Rat-1 SH2+M74) and (Rat-1 SH2+stearic acid) were imaged. DMSO (0.2%) and stearic acid (30 µM) had no effect on foci formation.

Example 3

Synergistic Inhibition of EGFR Tyrosine Kinase Activity and NSCLC Cell Growth by Combination Treatment with FUS1-Nanoparticle and Gefitinib New cancer treatments designed to restore functions of defect genes and gene products in tumor suppressing and apoptotic pathways by gene transfer and to target at the specific and frequently occurring molecular alterations in key signaling pathways by "smart drugs" such as protein tyrosine kinase inhibitors (PTKIs) are fundamentally changing cancer therapy and holding a promise for lung cancer treatment. FUS1 is a novel tumor suppressor gene (TSG) identified in the human chromosome 3p21.3 region that is frequently altered or deleted in many human cancers and has been shown to function as a key mediator in Apaf1-associated apoptotic pathway and as a potent tumor suppressor in vitro and in vivo. In light of our recent observations on the FUS 1-mediated PTK inhibition and the direct interactions of FUS1 with PTK and Apaf1 proteins together with the current findings of activating mutations of EGFR gene in gefitinib-responders in NSCL patients and the role of these mutations in selectively activating cell survival signaling and blocking pro-apoptotic pathway by other researchers, in this study the inventors explored the capability of using the multifunctional FUS1 as a modulator for enhancing chemotherapeutic potency of gefitinib and overcoming gefitinib-resistance by simultaneously inactivating cell survival and proliferation signaling and activating proapoptotic pathways in both gefitinib-sensitive and resistant NSCLC cells. The inventors found that reactivation of wt-FUS1 by FUS1-nanoparticle-mediated gene transfer or treatment with a wt-FUS1-derived peptide (wt-FP) in 3p-deficeint and Gefitinib-resistant NSCLC H1299, H358, and H460 cells significantly sensitized these cells' response to Gefitinib treatment, as demonstrated by a more than additive inhibitory effect on tumor cell growth and a synergistic induction of apoptosis. An enhance growth inhibition was also observed in gefitinib-sensitive HCC827(with an activating mutation of EGFR) and H1819 (with amplification of EGFR) cells co-treated with FUS1-nanoparticles and a very low dose of gefitinib (at a level of $IC_{10}$). A marked inhibition on activities of phosphorylated EGFR and Erk proteins was also detected in cells treated by FUS1-nanoparticle or wt-FP alone or in combination with gefitinib, as demonstrated by Western-blot analysis with phosphor-EGFR or Erk-specific antibodies. Our results suggest that the wt-Fus1 may play a critical role in modulating the sensitivity of tumor cells to the chemotherapeutic agents such as PTKIs and that a combination treatment of the FUS1-nanoparticle-mediated molecular therapy with these small molecule chemotherapeutics may be an efficient treatment strategy for lung cancer.

Example 4

Inactivation of c-Abl and c-Kit Activities and Inhibition of SCLC Cell Growth by a Combination Treatment with FUS1-Nanoparticle and Gleevec In Vitro and In Vivo.

FUS1 is a novel tumor suppressor gene identified in a critical human chromosome 3p21.3 region that has either LOH in more than 95% of SCLC cells or is homozygously deleted in some SCLCs. Expression of FUS1 protein is lost in all SCLC cells tested and reactivation of wt-FUS1 in FUS1-deficient lung cancer cells inhibits their growth by induction of apoptosis. On the other hand, protein tyrosine kinases (PTKs) such as BCR-Abl, c-Kit and PDGFR are frequently altered and amplified in SCLC and are important therapeutic targets. The small molecular drug gleevec has been shown to inhibit SCLC cell growth by targeting c-Kit/SCF pathway in vitro but exhibits no significant therapeutic efficacy either in animal models or in human clinic trials. The inventors hypothesized that a combination treatment strategy with DOTAP:Chol-complexed FUS1-nanoparticle and gleevec might promote a synergistic inhibition on SCLC growth by simultaneously inactivating the oncogenic PTK signaling and activating the pro-apoptotic pathways. A significant growth inhibition and apoptosis were observed in SCLC H69, H128, H146, and N417 cells treated by either the FUS1-nanoparticle or the wt-FUS1-derived peptide (wt-FP) for 72 h but not by dysfunctional mutants of FUS1 protein or peptide, compared to these treated by the GFP-nanoparticle or peptide controls. An enhanced growth inhibition was detected in gleevec-resistant H69R and N417 cells treated by a combination of FUS1-nanoparticle or wt-FP with gleevec compared to those treated by either agent alone. Activities of the phosphorylated c-Abl and c-Kit proteins were also significantly inhibited in H69 and N417 cells treated by FUS1-nanoparticle or wt-FP alone or in combination with gleevec, as shown by both the immuno-blot analysis and the activity assay using the immuno-precipiated phosho-c-Abl or phospho-c-Kit proteins. The inventors developed an intrathoracic SCLC N417 tumor xenograft model in nude mouse and evaluated the therapeutic efficacy of systemic treatment with FUS1-nanoparticles and oral administration with Gleevec by a noninvasive and quantitative MR imaging analysis. The inventors found that the growth of N417 tumor xenograft was significantly inhibited ($P<0.001$) in mice treated by FUS1-nanoparticles alone or in combination with gleevec in less than 2 weeks of treatment but no significant efficacy was detected in mice treated by gleevec alone, as demonstrated by MR imaging and volume analysis. Our results clearly demonstrate the therapeutic efficacy of FUS1-nanoparticle on SCLC in vitro and in vivo and implicate the translational applications of using the systemic administration of FUS1-nanoparticle alone or in combination with other chemotherapeutic agents and the MRI for SCLC therapy.

Example 5

Activated c-Abl in FUS1 Haploinsufficient Non-Small Cell Lung Carcinoma

The-Abl protein is widely expressed in all tissues but oncogenically activated forms of c-Abl are restricted to hematopoietic malignancies (e.g. Philadelphia chromosome+ chronic myeloid leukemia involving BCR-ABL fusions). The c-Abl protein is a tightly regulated tyrosine kinase that is located in both the cytoplasm and nucleus. The nuclear form of c-Abl protein is known to be activated in response to DNA damage. Cytoplasmic c-Abl is associated with growth factor receptor signaling, cell mobility, and cell adhesion. The Bcr protein is known to be a negative regulator of c-Abl and Bcr-Abl oncoproteins (Lin et al., 2001; Ling et al., 2003). In addition, PAG down-regulates c-Abl by interaction with the SH3 domain. (Wen and Van Etten, 1997). In lung cancer, frequent loss of one allele of chromosome arm 3p is seen in both small cell lung cancer (SCLC) and non-small cell lung cancer (NSCLC), providing evidence of tumor suppressor genes (TSGs) in this chromosome region (Kondo et al., 2001; Uno et al., 2004). The FUS1 gene has been identified in this critical chromosome region and is considered a novel tumor suppressor gene. The mechanism of Fus1 tumor suppressor activity is unknown. The inventors have found that a Fus1 peptide inhibits the c-Abl tyrosine kinase in vitro (IC50 35 µM). The inhibitory sequence was derived from a region that was deleted in one of the mutant Fus1 proteins detected in some lung cancer cell lines. Importantly, a stearic acid (C18 fatty acid) modified form of this peptide was required for the inhibition, but stearic acid alone was not inhibitory. Of interest, the myristate (C14) fatty acid bound to the amino terminal segment of c-Abl is thought to be involved in auto-inhibition of c-Abl (Hantschel et al., 2003). The inventors tested the effects of the Fus1 peptide on foci formation using Rat-1 cells transformed with an activated c-Abl tyrosine kinase. The inventors found that the stearic acid-Fus-1 peptide (40 µM) blocked foci formation. These findings suggest that one of the activities of the Fus1 tumor suppressor protein is to interfere with c-Abl tyrosine kinase function. Analysis of two lung cancer cell lines with allelic loss in this 3p21.3 region, leading to haploinsufficiency in the FUS1 gene, suggest that activated c-Abl may play a role in FUS1 deleted lung cancers. Immunoprecipitation/pTyr Western blots studies and in vitro Abl kinase assays showed that the A549 and H1299 cell lines contained an activated c-Abl protein. Further studies are in progress to investigate Fus1/Abl interaction and to identify sequences within FUS1 that are critical for c-Abl tyrosine kinase inhibition.

Example 6

Synergistic Inhibition of EGFR Tyrosine Kinase and Tumor Cell Growth in Non-Small Cell Lung Cancer (NSCLC) by Combination Treatment with FUS1-Nanoparticles and Gefitinib FUS1 is a novel tumor suppressor gene (TSG) identified in the human chromosome 3p21.3 region that functions in the Apaf1-associated apoptotic pathway, and is a potent tumor suppressor. The inventors explored the use of FUS1 for enhancing chemotherapeutic potency of Gefitnib and overcoming Gefitnib-resistance in both Gefitnib-sensitive and resistant NSCLC cells.

Methods and Results

The inventors found that expression of wt-FUS1 by FUS1-nanoparticle-mediated gene transfer in FUS1-deficient and Gefitinib-resistant NSCLC H1299, H358, and H460 cells significantly sensitized the response to Gefitinib treatment, as demonstrated by a more than additive inhibitory effect on tumor cell growth and a synergistic induction of apoptosis. Enhanced growth inhibition was also observed in the Gefitnib-sensitive HCC827 (EGFR mutant) and H1819 (EGFR amplification) cells co-treated with FUS1-nanoparticles and a low dose of Gefitnib ($IC_{10}$). A marked inhibition of phosphorylated EGFR protein was also detected in cells treated with FUS1-nanoparticles alone or in combination with Gefitinib, as shown by Western-blot analysis with phospho-EGFR-specific antibodies. A significant inhibition (P<0.001) of tumor growth was detected in animals treated by FUS1-nanoparticles in less than 2 weeks of treatment compared to those untreated or treated by GFP-nanoparticles, as shown by MR imaging and volume analysis. Induction of apoptosis was also detected in tumor cells in mice treated by FUS1-nanoparticles by an in situ apoptosis assay with TUNEL staining in frozen tissue samples. The inventors have an ongoing phase I study of single agent FUS1-nanoparticles given intravenously in stage IV NSCLC patients who have progressed on chemotherapy. The treatment is well-tolerated in seven patients entered to date with a median survival of 17+ months.

Conclusions

Our results suggest that wt-FUS1 may play a critical role in modulating the sensitivity of tumor cells to protein tyrosine kinase inhibitors.

Example 7

Our previous experiments showed that a synthetic peptide derived from the Fus1 sequence know to be deleted in Fus1 from some lung cancer cell lines inhibits the kinase activity of commercial Abl. The inventors screened two human non-small cell lung cancer (NSCLC) cell lines, A549 and H1299, by anti-Abl immunoprecipitation (IP)/pTyr Western blotting and detected an activated c-Abl protein. To confirm the activation of c-Abl in FUS1 deleted NSCLC cell lines, an in vitro kinase assay was performed using c-Abl antibody IPs. Both A549 and H1299 were positive for activated c-Abl, while CCD16, a normal human lung fibroblast cell line, was negative.

To further investigate the activity of c-Abl in NSCLC cell lines, imatinib mesylate (also known as STI-571 or Gleevec), a known inhibitor or c-Abl tyrosine kinase, was used in soft agar colony assays of H1299 cells. Treatment of cells with imatinib (10 µM) led to an almost complete reduction in the number of colonies compared to the untreated control. Those colonies that did form in the presence of imatinib were reduced in size compared to untreated cells.

To determine the direct effects of Fus1 on c-Abl inside cells, c-Abl cDNA was co-transfected into COS-1 cells with either wild-type FUS1 or a c-terminus deleted FUS1 or an empty vector. Our data indicates that there is a decrease in tyrosine phosphorylation of c-Abl associated with wild-type Fus1 co-expression, but this decrease was not seen with the FUS1 deletion mutant which lacks the inhibitory peptide sequence of the Fus1 peptide.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 8

Delivery of FUS-1 Peptide Via Neutral Liposome Nanoparticles

The delivery system used in this example consists of neutral nano-particle (1, 2-Dioleoyl-sn-Glycero-3-phosphatidyl-choline (DOPC)(Avanti Polar lipids, Alabaster, Ala.)-based liposomes and a peptide (Fus 1). DOPC stock (20 mg/ml) was prepared in t-butanol and mixed with tween-20 (Fisher Scientific, Fairlawn, N.J.), which was diluted (1:1000) in distilled water, at ratio of 90%: 10%, (v/v) (DOPC:Tween 20). The mixture was added excess absolute t-butanol (95% t-butanol, 5% lipid, v/v) and lyophilized overnight. Dry lipid mixture was mixed with the peptide that was already dissolved in distilled water. The DOPC and peptide ratio used in these experiments was a 10:1, molar ratio (DOPC:peptide). 100 µM peptide containing ddwater was diluted and used for the treatment of lung cancer cells (H1299). A cationic lipid, DOTA, and peptide was used as a positive control (DOTAP:peptide (1:1), M/M).

Figure 23:
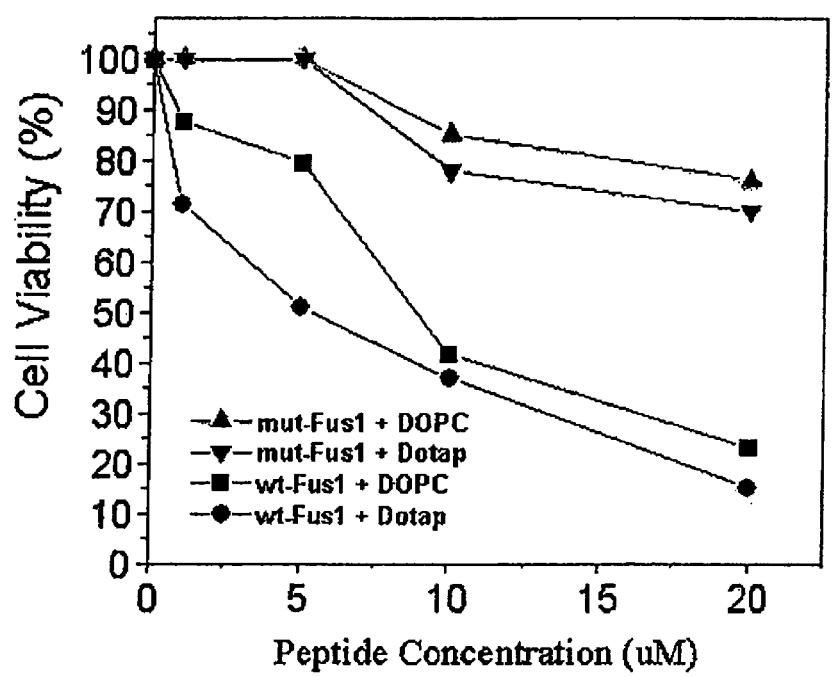
FIG. 23: Effects of DOPC and DOTAP based liposomes containing Fus1 peptide on growth of non small cell lung carcinoma cells (H1299 cells) in 48 h.

Lung cancer cells (5000/well) were treated with increasing doses of empty liposomes and liposomes containing fus 1 peptide (1, 5, 10, and 20 µM peptide) or liposomes containing dye-labeled peptide 1, 5, 10, and 20 µM) for 48 h. Uptake of liposomes was observed using fluorescent microscope at 20 and 48 h time points. Cells were photographed at 20 and 48 h of treatment for morphology and viability. The cells treated with empty liposomes (control) and cells treated with liposomes containing peptide were counted for cell viability after 48 h and finding were plotted (FIG. 23).

Example 9

Analysis of the Toxicity of DOPC and DOTAP:Cholesterol Nanoparticles Optionally Containing FUS-1 Peptide C3H mice were injected with a nanoparticle containing a peptide (either the FUS-1 peptide or a nonspecific peptide), and various toxicological parameters were subsequently analyzed at 1, 2 and 3 weeks after injection. Control mice ("Group IX") were injected with PBS. The toxicological parameters evaluated included hematological parameters (i.e., red blood cell counts "RBC" and white blood cell counts "WBC"), analysis of hepatic function (i.e., AST, ALT, and total bilirubin analysis) and analysis of renal function (i.e., evaluation of creatinine levels). Either DOTAP:cholesterol nanoparticles or DOPC (neutral liposome) nanoparticles were used. The amount of peptide-containing nanoparticle administered to the C3H mice varied from 2 mg/kg to 5 mg/kg. These studies are summarized below in Table V.

TABLE V

Toxicity analysis of nanoparticles
Toxicity Study of FP-nanoparticle in C3H mice (5 mice/Group)

| | | | Group I | Group II FP (mg/kg) | | Group III NSP (mg/kg) | | Group IV FP-DC (mg/kg) | |
|---|---|---|---|---|---|---|---|---|---|
| | | | DC | 2 | 5 | 2 | 5 | 2 | 5 |
| Hemotological Parameters | WBC ($\times 10^9$) | 1st week | | | | | | | 1.14 ± 0 |
| | | 2nd week | 3.37 ± 0.42 | 1.6 ± 0.43 | 1.47 ± 0.34 | 1.93 ± 0.58 | 1.6 ± 0.24 | 1.5 ± 0.51 | 1.77 ± 0.57 |
| | | 3rd week | 2.0 ± 0.74 | 2 ± 0.49 | 1.73 ± 0.09 | 1.93 ± 0.45 | 1.6 ± 0.14 | 1.87 ± 0.31 | 2.23 ± 0.45 |
| | RBC ($\times 10^9$) | 1st week | | | | | | | 5.42 ± 0 |
| | | 2nd week | 3.83 ± 1.07 | 8.13 ± 0.98 | 8.5 ± 1.19 | 6.23 ± 0.33 | 7.47 ± 2.28 | 6.37 ± 2.22 | 6.6 ± 2.37 |
| | | 3rd week | 7.7 ± 2.43 | 7.87 ± 0.49 | 5.6 ± 0.78 | 5.7 ± 1.14 | 6.67 ± 0.69 | 7.07 ± 0.09 | 5.63 ± 2.71 |
| Hepatic Function | AST (U/L) | 1st week | 337.5 ± 193.5 | 199 ± 31.02 | 162 ± 25.57 | 183 ± 6 | 148.5 ± 13.5 | 133.5 ± 34.5 | 142.67 ± 39.42 |
| | | 2nd week | 161.33 ± 85.23 | 106.33 ± 2.49 | 100.33 ± 25.3 | 146 ± 45.31 | 96.33 ± 20.24 | 88.33 ± 9.74 | 120.67 ± 33.11 |
| | | 3rd week | 124.33 ± 27.35 | 88 ± 15.30 | 130 ± 62.01 | 94.67 ± 28.59 | 83.67 ± 23.63 | 103 ± 20.83 | 154 ± 57.88 |
| | ALT (U/L) | 1st week | 84 ± 30 | 84 ± 8.49 | 88 ± 5.1 | 76 ± 7.87 | 91.5 ± 7.5 | 72 ± 12.96 | 71 ± 9.9 |
| | | 2nd week | 61.33 ± 18.19 | 58 ± 6.16 | 46.33 ± 0.94 | 61.67 ± 5.44 | 54 ± 9.93 | 46.67 ± 3.68 | 54.67 ± 7.72 |
| | | 3rd week | 58.33 ± 6.13 | 52.67 ± 4.92 | 53 ± 8.83 | 58.67 ± 12.55 | 50 ± 6.16 | 51.33 ± 4.11 | 56.67 ± 8.99 |
| | Total Bilirubin (mg/dl) | 1st week | 1.8 ± 0 | 2.7 ± 1.07 | 1.65 ± 0.75 | 2.7 ± 0 | 1.8 ± 1.2 | 1.05 ± 0.15 | 1.57 ± 0.71 |
| | | 2nd week | 2.15 ± 0.16 | 0.9 ± 1.25 | 0.6 ± 0.45 | 1.13 ± 1.09 | 0.7 ± 0.28 | 0.43 ± 0.33 | 1.2 ± 0.57 |
| | | 3rd week | 0.9 ± 0.36 | 0.63 ± 0.25 | 1.13 ± 0.63 | 0.6 ± 0.42 | 0.43 ± 0.12 | 0.8 ± 0.22 | 1.17 ± 0.17 |
| Renal Function | Creatinine (mg/dl) | 1st week | 0.24 ± 0 | 0.34 ± 0 | 0.37 ± 0.07 | 0.6 ± 0 | 0.317 ± 0.02 | 0.18 ± 0 | 0.49 ± 0.25 |
| | | 2nd week | 0.51 ± 0.10 | 0.51 ± 0.14 | 0.48 ± 0.05 | 0.5 ± 0.10 | 0.35 ± 0.02 | 0.32 ± 0.03 | 0.36 ± 0.02 |

TABLE V-continued

Toxicity analysis of nanoparticles
Toxicity Study of FP-nanoparticle in C3H mice (5 mice/Group)

| | | | | | | | Group VII FP-DOPC | Group VIII NSP-DOPC | |
|---|---|---|---|---|---|---|---|---|---|
| | | | 3rd week | 0.55 ± 0.08 | 0.50 ± 0.01 | 0.54 ± 0.05 | 0.38 ± 0.09 | 0.32 ± 0.04 | 0.38 ± 0.04 | 0.46 ± 0.03 |

| | | | Group V NSP-DC (mg/kg) | | Group VI | Group VII FP-DOPC | Group VIII NSP-DOPC | Group IX |
|---|---|---|---|---|---|---|---|---|
| | | | 2 | 5 | DOPC | 5 mg/kg | 5 mg/kg | PBS |
| Hemoto- | WBC | 1st week | 2.83 ± 0.23 | 2.22 ± 1.45 | 1.68 ± 1.5 | 0.99 ± 0.24 | 3.56 ± 0.25 | 4.42 ± 0.93 |
| logical | ($\times 10^9$) | 2nd week | 3.03 ± 1.83 | 0.67 ± 0.29 | 1.3 ± 0.28 | 2 ± 0.29 | 0.53 ± 0.09 | 1.93 ± 1.26 |
| Para- | | 3rd week | 2.97 ± 2.19 | 1.37 ± 0.33 | 1.63 ± 0.39 | 2.67 ± 0.41 | 1.93 ± 0.63 | 1.58 ± 0.39 |
| meters | RBC | 1st week | 7.25 ± 0.79 | 6.71 ± 1.45 | 6.68 ± 1.70 | 6.75 ± 2.02 | 8.65 ± 1.13 | 7.63 ± 1.84 |
| | ($\times 10^9$) | 2nd week | 6.8 ± 1.61 | 2.37 ± 0.26 | 5.33 ± 0.33 | 6.73 ± 1.08 | 3.17 ± 1.56 | 6.38 ± 2.22 |
| | | 3rd week | 8.03 ± 1.74 | 7.13 ± 0.61 | 6.23 ± 1.27 | 8.6 ± 0.50 | 5.67 ± 0.74 | 5.93 ± 0.58 |
| Hepatic | AST | 1st week | 108.67 ± 12.5 | 117.07 ± 15.97 | 106.07 ± 9.46 | 103.67 ± 14.64 | 76 ± 13.44 | 101.25 ± 28.28 |
| Function | (U/L) | 2nd week | 155.33 ± 32.79 | 128.33 ± 19.74 | 212 ± 0 | 175.33 ± 23.17 | 159.33 ± 9.53 | 144 ± 59.22 |
| | | 3rd week | 93.33 ± 11.67 | 98.67 ± 16.50 | 100.67 ± 22.29 | 123 ± 52.62 | 82.67 ± 39.85 | 122.25 ± 90.94 |
| | ALT | 1st week | 51.33 ± 4.11 | 57 ± 9.42 | 45.33 ± 3.3 | 50 ± 3.74 | 44 ± 4.97 | 52.75 ± 11.52 |
| | (U/L) | 2nd week | 56 ± 4.32 | 46 ± 3.74 | 47 ± 0 | 56.67 ± 2.49 | 51.33 ± 4.71 | 58 ± 38.62 |
| | | 3rd week | 50.67 ± 8.26 | 52 ± 2.16 | 48.67 ± 6.60 | 57.67 ± 10.87 | 45.67 ± 9.43 | 56.25 ± 19.47 |
| | Total | 1st week | 1.2 ± 0.16 | 1.03 ± 0.26 | 1.3 ± 0.37 | 1.07 ± 0.34 | 0.57 ± 0.17 | 0.95 ± 0.46 |
| | Bilirubin | 2nd week | 2.57 ± 0.84 | 1.4 ± 0.16 | 5.3 ± 2.5 | 3.27 ± 0.47 | 2.17 ± 0.52 | 2.58 ± 1.96 |
| | (mg/dl) | 3rd week | 0.83 ± 0.17 | 0.93 ± 0.12 | 0.73 ± 0.19 | 0.9 ± 0.65 | 0.57 ± 0.38 | 0.675 ± 0.65 |
| Renal | Creatinine | 1st week | 0.64 ± 0.08 | 0.52 ± 0.08 | 0.54 ± 0.11 | 0.54 ± 0.06 | 0.39 ± 0.05 | 0.42 ± 0.06 |
| Function | (mg/dl) | 2nd week | 0.43 ± 0.05 | 0.44 ± 0.08 | 0.50 ± 0.04 | 0.31 ± 0.11 | 0.40 ± 0.00 | 0.45 ± 0.07 |
| | | 3rd week | 0.44 ± 0.01 | 0.52 ± 0.03 | 0.39 ± 0.02 | 0.36 ± 0.09 | 0.27 ± 0.06 | 0.25 ± 0.02 |

Notes:
1. Some hematological parameters in 1st week are not available due to severe hemolysis of samples.
2. FP-nanoparticle were injected via tail vein for three times in every other day, total volume of each dosage was 200 μl.
3. Time points for blood collection represent the time from the last treatment.
4. DC: DOTAP/Cholestrol-nanoparticle, FP: FUS1 Peptide, NSP: Non-specific Peptide.

Example 10

Inhibition of c-Abl by the Tumor Suppressor Gene Product Fus1: Oncogenic Activation of c-Abl in Non-Small Cell Lung Cancer Cells Lacking FUS1 Expression A stearate-Fus1 peptide inhibits the tyrosine kinase activity of c-Abl. Fus1 is a tumor suppressor gene associated with NSCLC (Ji et al., 2002; Lerman and Minna, 2000; Kondo et al., 2001). A C-terminal deletion mutant of FUS1 was isolated from a lung cancer tumor cell line (Kondo et al., 2001), which encodes the first 80 amino acids of the 110 amino acid wild-type Fus1 protein (Kondo et al., 2001). The inventors synthesized a stearate-Fus1 peptide (KLRRVHKNLIPQ-GIVKLDHR; SEQ ID NO:11) originating from sequences that are absent Fus1 (1-80), except for the KLR sequence (see Table VI). This peptide was strongly inhibitory in an Abl tyrosine kinase assay using bacterially purified Abl kinase (FIG. 24A). Surprisingly, the Fus1 peptide lacking the stearate N-terminal moiety was inactive as an Abl kinase inhibitor (FIG. 24B). Stearate alone was also not inhibitory. A stearate Bcr peptides was inactive as an Abl kinase inhibitor; a stearate Bcr peptide that is approximately the same number of amino acids as the stearate Fus1 peptide did not have any inhibitory effect on the bacterially purified Abl kinase. Together, these results indicate that both the stearate moiety and the amino acid sequences within the Fus 1 peptide were necessary for the inhibition of the c-Abl kinase.

As shown in FIG. 24A, stearic acid Fus1 peptide was incubated with a truncated commercial Abl tyrosine kinase (45 kD) (New England Bio-Labs), containing only the SH2 and SH1 domains, GST-CRK (c-Abl preferred substrate), 100 uM cold ATP, and 32P ATP. After 30 minutes of incubation at 30 degrees, samples were boiled with 2×SDS sample buffer and run on an 8% SDS PAGE gel. The gel was dried and exposed to a phosphoimager.

FIG. 24B shows linear inhibition of the Abl tyrosine kinase by stearic acid Fus1 peptide. The curve represents inhibition of GST-CRK phosphorylation. Non-stearic acid modified Fus1 peptide did not inhibit Abl tyrosine kinase activity (FIG. 24C). The 45 kD Abl tyrosine kinase (New England BioLabs) was incubated with 0-60 uM of non-stearate Fus1 peptide, 100 uM cold ATP, and 32P ATP, and GST-Crk. GST-Crk phosphorylation was quantified by using a phosphoimager.

The Fus1 amino acid sequence and stearate-Fus1 peptide sequence are shown below in Table VI. The underlined amino acid sequence below is the region from which the Fus1 peptide was derived. The peptide sequence, except for KLR N-terminus, is located in a region that is absent in a mutant truncated form of FUS1 [FUS1 (1-80)] expressed in some NSCLC cell lines (Kondo et al., 2001).

TABLE VI

```
Fus1 peptide:
stearate-78KLRRVHKNLIPQGIVKLDHR        SEQ ID NO: 11

Fus1 amino acid sequence
  1 mgasgskarg lwpfasaagg ggseaagaeq    SEQ ID NO: 12
 31 alvrprgrav ppfvftrrgs mfydedgdla
 61 hefyeetivt knqgkraklr rvhknhipqq
 91 ivkldhprih vdfpvilyev
```

The c-Abl tyrosine kinase is activated in NSCLC cell lines. Several NSCLC cell lines were examined for the presence of activated c-Abl (Table VII). The A549 and H1299 cell lines contained a tyrosine kinase-active c-Abl protein as determined by immune complex kinase assays performed with anti-Abl P6D. Anti-Abl immune complexes from the cell lysates of these cell lines also contained a tyrosine-phosphorylated c-Abl protein.

TABLE VII

Decreased FUS1 expression correlates with activated c-Abl activity in NSCLC cell lines

| Cell lines | FUS1 expression | Activated c-Abl |
|---|---|---|
| Control cell lines | | |
| Rat 1 | Unknown | No |
| Rat1 SH2 | Unknown | Yes |
| Normal lung fibroblast | | |
| CCD16 | Unknown | No |
| NSCLC | | |
| A549 | No | Yes |
| H358 | No | Yes |
| H1299 | No | Yes |
| H2089 | No | Yes |
| H2122 | No | Yes |

NSCLC cell lines were shown to contain activated c-Abl tyrosine kinase. Whole cell lysates from Bcr-Abl positive cell line, 32D P210, normal lung fibroblast, CCD16, and NSCLC cell lines, H1299 and A549 were incubated with anti-c-Abl antibody P6D (Ling et al., 2003). P6D, and the immune complexes pulled down by protein A Sephorose beads. Protein A beads were incubated with 2 μCi 32P ATP for 20 minutes on ice. Supernatants were boiled in 2×SDS sample buffer and analyzed on an 8% SDS-PAGE gel. Whole cell lysates from normal Rat 1 cells, c-Abl transformed Rat 1 cells, ABL transformed Rat1 cells (Ling et al., 2003), and NSCLC cells, H1299 and A549, were incubated with anti-c-Abl antibody P6D. P6D immune complexes were harvested with by protein A Sephorose beads. Protein A beads were boiled in 2×SDS sample buffer and analyzed by SDS-PAGE1. The bBlot was probed with anti-c-Abl antibody 8E9 (Guo et al., 1994). Blot was then stripped and probed with phosphotyrosine antibody 4G10 (Upstate).

Figure 25A:
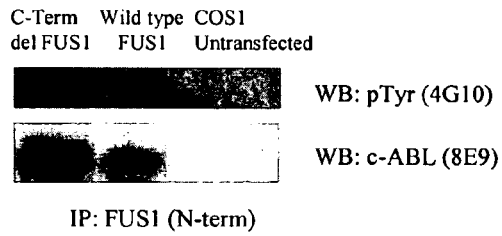
FIGS. 25A-C. FUS1 expression inhibits c-Abl tyrosine kinase activity.
Figure 25B:
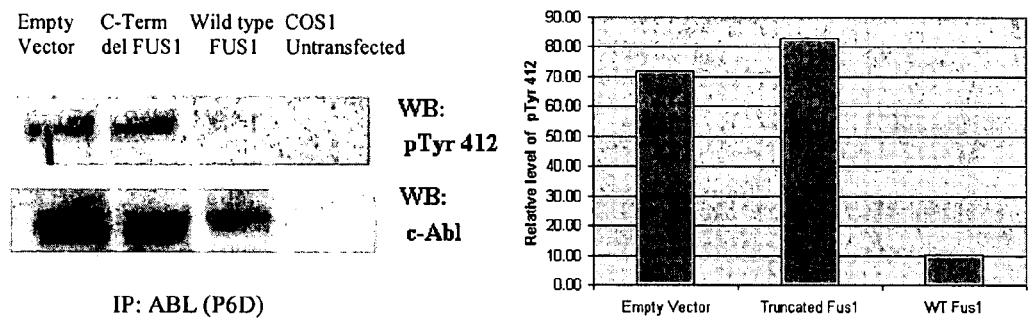
Figure 25C:
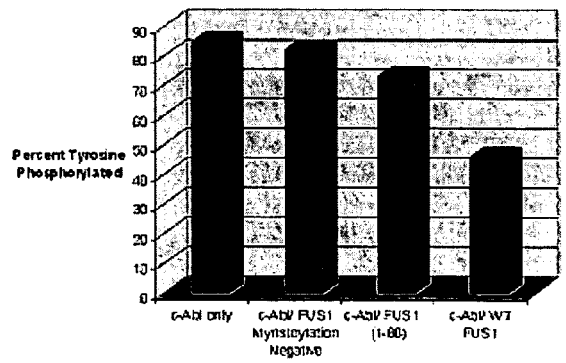

Co-expression of FUS1 and c-ABL in COS1 cells inhibits c-Abl tyrosine kinase activity. To assess the ability of Fus1 to inhibit activated c-Abl, we co-expressed these cDNAs in COS1 cells and measured levels of tyrosine-phosphorylated c-Abl. Co-expression of c-ABL with FUS1 inhibited the phosphorylation of c-Abl on tyrosine residues (FIG. 25A). In contrast, co-expression of FUS (1-80) with c-ABL had little inhibitory effect on c-Abl tyrosine phosphorylation (FIG. 25A). Of interest, immunoprecipitation of Fus1 with a N-terminal Fus1 antibody co-precipitated c-Abl along with Fus1, suggesting that Fus1 is associated with c-Abl. Phosphorylation of tyrosine 412 of c-Abl is a measure of c-Abl tyrosine kinase activation. Therefore, we assessed the level of phosphotyrosine 412 sequences in c-Abl following co-expression of FUS1 (FIG. 25B). FUS1 co-expression with c-Abl strongly inhibited the level of phosphotyrosine 412 in the c-Abl protein. In contrast, co-expression of FUS (1-80) with c-ABL failed to inhibit phosphorylation of tyrosine 412 (FIG. 25B). A study has shown that myristoylation of Fus1 is required for its tumor suppression activity in NSCLC. Co-expression of c-ABL with a myristoylation-deficient mutant of FUS1 in COS1 cell resulted in a minimal decrease in phosphotyrosine c-Abl when compared to co-expression of wild type FUS1 and c-ABL (FIG. 25C). Thus, this result indicates that Fus1 interaction with c-Abl blocks its tyrosine kinase activation either as a result of autophosphorylation or by Abl activation by another upstream kinase such as c-Src (Plattner et al., 1999).

In FIG. 4a, COS1 cells were co-transfected with c-ABL and either wild type FUS1 or, FUS (1-80). At 48 hr post transfection, cells were harvested and lysates incubated with N-terminal Fus1 antibody. Fus1 immune complexes harvested with protein A beads were boiled in 2×SDS sample buffer and and analyzed by SDS-PAGE. The blot was probed with antiphosphotyrosine antibody 4G10 (Upstate). The blot was stripped and re-probed with anti-c-Abl antibody 8E9. In FIG. 4b, COS1 cells were co-transfected with c-Abl and either empty vector, FUS (1-80), or wild type FUS1. At 48 hr post transfection, the cells were harvested and lysates incubated with anti-c-Abl, P6D. as in FIG. 4a. The blot was probed with c-Abl anti-phosphotyrosine 412 (Abcam). The blot was then stripped and re-probed with anti-c-Abl antibody 8E9.

Figure 26C:
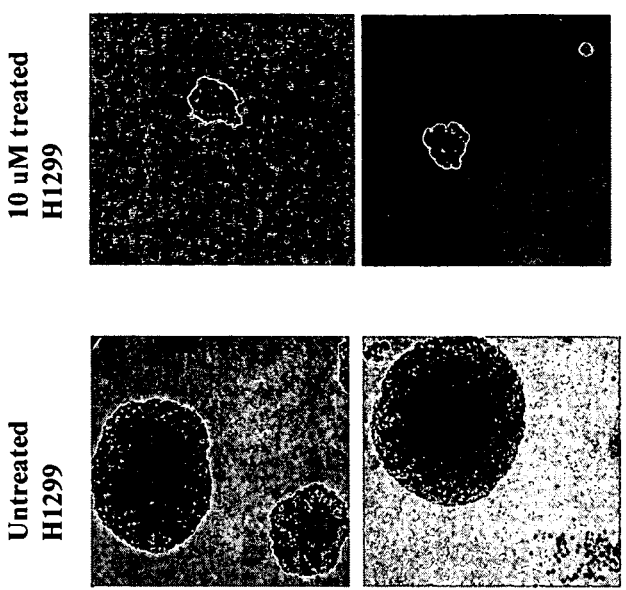
FIGS. 26A-C.
Figure 26A:
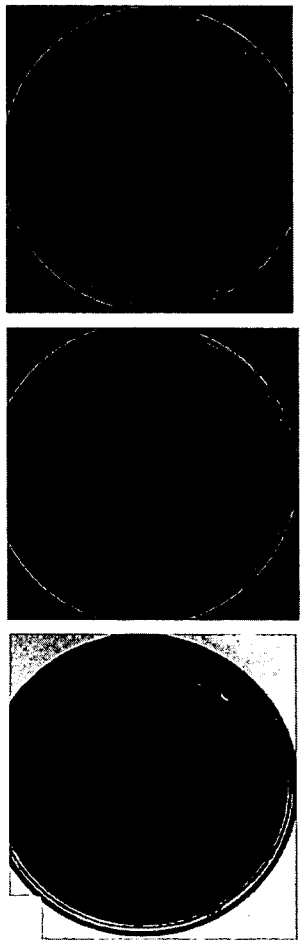
Figure 26B:
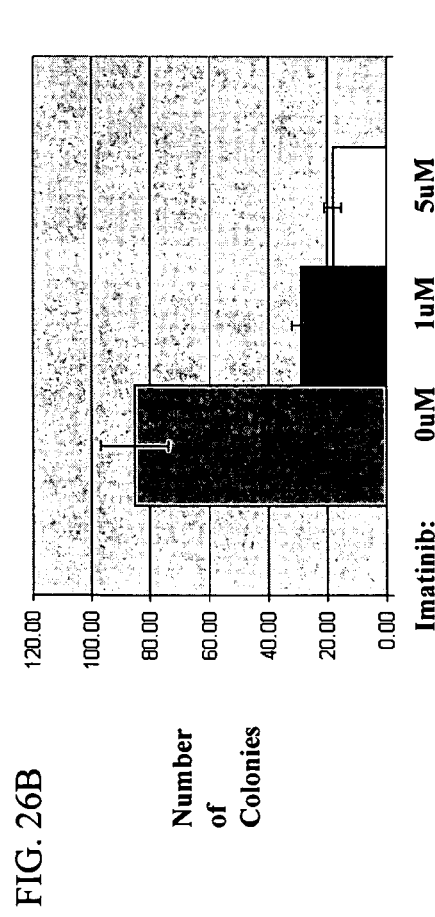

Imatinib inhibits colony formation of NSCLC cells. Imatinib mesylate (Gleevec) is widely known for its ability to inhibit the activated tyrosine kinase activity of Bcr-Abl (Druker et al., 1996). The inventors therefore tested the effects of imatinib on colony formation of H1299 cells in soft agar (FIGS. 26A-C). Imatinib treatment strongly inhibited the colony-forming ability of H1299 cells in a dose-dependent manner; both the number and size of colonies were inhibited (FIGS. 26A-C). 1-10 uM of imatinib was used in these assays, as previous studies have demonstrated strong inhibition of c-Abl kinase activity at these concentrations (Zipfel et al., 2004).

Discussion

Previous studies have demonstrated the anti-tumor activity of FUS1 (Kondo et al., 2001; Uno et al., 2004), but targets of the FUS1 gene have not been identified so far. In our studies, c-Abl was found to be negatively regulated by the Fus1 protein. Using a FUS1 peptide derived from sequences lacking in the mutant FUS1 (1-80) (Kondo et al., 2001) seen in some NSCLC patients, we were able to inhibit c-Abl kinase's ability to phosphorylate Crk, a normal target of c-Abl (17) (FIGS. 24A-C). Of interest, only the stearic acid modified form of the FUS1 peptide had inhibitory effects on c-Abl kinase (FIGS. 24A-C). It has been shown that the myristolyation of FUS1 is required to produce the tumor suppression effects of FUS1 (Plattner et al., 1999). Of interest, the N-terminal of c-Abl (isoform 1b) also contains a myristate residue, which has been implicated in the auto-inhibition of c-Abl (Hantschel et al., 2003). Interaction of wild type Fus1 and c-Abl was shown in cell culture through co-expression assays in COS1 cells (e.g., FIGS. 25A-C). Phosphorylation of tyrosine 412 is a critical step that leads to the activation of c-Abl kinase (Brasher and Can Etten, 2000). Co-expression of wild type FUS1 and c-ABL leads to a significant decrease in both the total phosphotyrosine level of c-Abl and the level phosphotyrosine 412 content compared to only very small decrease in either signal when c-Abl is co-expressed with either a truncated FUS1 (lacking the inhibitory peptide sequence), found in some NSCLC cell lines (Wang, 2000), or the empty vector (FIGS. 25A-C). These findings provide strong evidence for direct inhibition of c-Abl tyrosine kinase by the Fus1 protein.

These results demonstrate that non-small cell lung cancer (NSCLC) cell lines express the tyrosine kinase-active c-Abl (FIGS. 24A-C). This result is interesting considering that c-Abl is a tightly regulated tyrosine kinase and its oncogenicity is usually associated with the chimeric protein, Bcr-Abl, in leukemia cells. In support of these findings showing activation of c-Abl in NSCLC lines, treatment of a NSCLC cell line with imatinib strongly inhibited colony formation in soft agar in a dose-dependent manner at doses that are known to inhibit the c-Abl tyrosine kinase (FIGS. 26A-C). Therefore our findings identify c-Abl as a possible target of the tumor suppressor gene product FUS1 and indicate that c-Abl maybe a significant contributor to the oncogenicity of some forms NCSLC. Thus, it seems likely that the well-known c-Abl inhibitor, imatinib, may have potential for successful treatment of NSCLC.

REFERENCES

The following references, to the extent that they provide exemplary procedural or other details supplementary to those set forth herein, are specifically incorporated herein by reference.

U.S. Pat. Nos. 4,162,282
4,310,505
4,533,254
4,554,101
4,728,575
4,728,578
4,737,323
4,921,706
5,030,453
5,397,987
5,855,911
5,962,016
6,413,544
6,610,657
6,680,068
6,770,291
U.S. Appln. 2004/0208921
Arap et al, *Cancer Res.*, 55(6):1351-1354, 1995.
Ausubel et al., *Current Protocols in Molecular Biology*, John Wiley & Sons, Inc., New York, N.Y., 1996; 1998
Bakhshi et al., *Cell*, 41(3):899-906, 1985.
Ballou et al., *Bioconjugate Chemistry*, 15:79-86, 2004.
Ben-Neriah et al., *Science*, 233:212-214, 1986.
Brady and Dodson, *Nature*, 368:692-693, 1994.
Buchhagen et al., *Head and Neck*, 18:529-537, 1996.
Butturini et al., *Leukemia Res.*, 20(6):523-529, 1996.
Caldas et al., *Nat. Genet.*, 8(1):27-32, 1994.
Cheng et al., *Cancer Res.*, 54(21):5547-5551, 1994.
Cheng et al., *Invest. Radiol.*, 22(1):47-55, 1987.
Cleary and Sklar, *Proc. Natl. Acad. Sci. USA*, 82(21):7439-43, 1985.
Cleary et al., *J. Exp. Med.*, 164(1):315-320, 1986.
Colledge and Scott, *Trends in Cell Biology*, 9:216-221, 1999.
Daly et al., *Oncogene*, 8:1721-1729, 1993.
Drin et al., *AAPS Pharm. Sci.*, 4(4): 1-7, 2002.
Du et al., *J. Pept. Res.*, 51:235-243, 1998.
Dubertret et al., *Science*, 298:1759-1762, 2002.
Dwarakanath et al., *Biochem. Biophysical Res. Commun.*, 325:739-743, 2004.
Ellerby et al. *Nature Med.*, 9:1032-1038, 1999.
Farhood et al., *Biochim. Biophys. Act*, 289-295, 1995.
Ferrari, *Nature Reviews*, 5:161-171, 2005.
Fidler and Ellis, *Cell*, 79(2):185-188, 1994.
Folkman and Shing, *J. Biol. Chem.*, 267(16):10931-10934, 1992.
Folkman, *Nature Med.*, 1:27-31, 1995.
Frangioni, *Current Opin. Chem. Biol.*, 7:626-634, 2003.
Gazdar et al. In: *Sym. Quant. Biol.*, Cold Spring Harbor, 59:565-572, 1994.
Gazdar et al., *Intl. J. Cancer*, 78:766-774, 1998.
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Gorunova et al., *Genes Chrom. Cancer*, 23:81-99, 1998.
Great Britain Appln. 2193095 A
Gupta et al., *Biomaterials*, 26:3995-4021, 2005.
Gupta et al., *Biomaterials*, 26:3995-4021, 2005.
Gupta et al., *Biomaterials*, 26:3995-4021, 2005.
Gupta, *IEEE Trans. Nanobioscience.*, 3:66-73, 2004.
Hanahan and Folkman, *Cell*, 86(3):353-364, 1996.
Hantschel et al., *Cell*, 112:845-857, 2003.
Hollstein et al., *Science*, 253(5015):49-53, 1991.
Hope et al., 1985
Horowitz, In: *MRI Physics for Radiologists: A Visual Approach*, 1995
Hughson et al., *Cancer Genet. Cytogenet.*, 106:93-104, 1998.
Hussussian et al., *Nat. Genet.*, 8(1):15-21, 1994.
Hvalby et al., *Proc. Natl. Acad. Sci. USA*, 91:4761-4765, 1994.
Ito et al., *Cancer Gene Therapy*, 11:733-739, 2004.
Jameson et al., *Nature* 368: 744-746, 1994
Ji et al., *Cancer Res.*, 62:2715-2720, 2000.
Johnson et al., *J. Virol.*, 67:438-445, 1993.
Kamb et al., *Nat. Genet.*, 8(1):23-26, 1994.
Kamb et al., *Science*, 2674:436-440, 1994.
Kerr et al., *Br. J. Cancer*, 26(4):239-257, 1972.
Kerr et al., *Br. J. Cancer*, 26(4):239-257, 1972.
Kersemaekers et al., *Intl. J. Cancer*, 79:411-417, 1998.
Kloetzer et al., *Virology*, 140(2):230-238, 1985.
Kohno et al., *Cancer*, 85:341-347, 1999.
Kondo et al., *Oncogene*, 20:6258-6262, 2001.
Kondo et al., *Oncogene*, 20:6258-6262, 2001.
Kyte and Doolittle, *J. Mol. Biol.*, 157(1):105-132, 1982.
Lewin et al., *Nat. Biotechnol.*, 18:410-414, 2000.
Lin et al., *Oncogene*, 20:1873-1881, 2001.
Ling et al., *Cancer Res.*, 63:298-303, 2003.
*Liposome Technology*, Gregoriadis (Ed.), Boca Raton, Fla., CRC Press, 1984.
Mabry et al., In: *Lung Cancer in the Genetic Basis of Human Cancer*, Vogelstein and Kinzler (Eds.), McGraw Hill, 671-679, 1998.
Mayer et al., *Biochim. Biophys. Acta*, 858(1):161-168, 1986.
Mayhew et al., *Biochim. Biophys. Acta*, 775(2):169-174, 1984.
Mayhew et al., *Methods Enzymol.*, 149:64-77, 1987.
Michalet et al., *Science*, 307:538-544, 2005.
Miller et al., *Oncogene*, 22:6006-6013, 2003.
Minna et al., In: *Cancer: Principles and Practice of Oncology*, 5$^{th}$ Ed., Philadelphia: Lippincott, 849-857, 1997.
Morawski et al., *Current Opinion Biotech.*, 16, 89-92, 2005.
Mori et al., *Cancer Res.*, 54(13):3396-3397, 1994.
Nishihara et al., *Cancer Letter*, 180(1):55-61, 2002.
Nobri et al., *Nature (London)*, 368:753-756, 1995.
Obenauer et al., *Nucleic Acids Res.*, 31(13):3635-3641, 2003.
Okamoto et al., *Proc. Natl. Acad. Sci. USA*, 91(23):11045-11049, 1994.
Orlow et al., *Cancer Res*, 54(11):2848-2851, 1994.
Orlow et al., *Int. J. Oncol.*, 15(1):17-24, 1994.
PCT Appln. PCT/US85/01161
PCT Appln. PCT/US89/05040
PCT Appln. WO 02/100435A1
PCT Appln. WO 03/015757A1
PCT Appln. WO 04/002453A1
PCT Appln. WO 04029213A2
*Pure & Appl. Chem.*, 63(3):427-463, 1991
Remington's Pharmaceutical Sciences" 15th Edition, pages 1035-1038 and 1570-1580, 1990.
Roberts et al., *Adv. Drug Del. Rev.*, 54(4):459-476, 2002.
Rojas et al., *J. Biol. Chem.*, 271:27456-27461, 1996.
Rojas et al., *Nature Biotechnol.*, 16:370-375, 1998.
Roth, *Forum*, 8:368-376, 1998.
Sambrook et al., In: *Molecular Cloning: A Laboratory Manual*, 2nd Ed., Cold Spring Harbor Press, Cold Spring Harbor, N.Y., 1989

Schwarze et al., *Science*, 285:1569-1572, 1999.
Schwarze et al., *Trends Cell Biol.*, 10:290-295, 2000.
Sekido et al., *Biochimica. Biophysica. Acta*, 1378:F21-F59, 1998.
Sekido et al., *Oncogene*, 16:3151-3157, 1998.
Sekido et al., *Proc. Natl. Acad. Sci. USA*, 93:4120-4125, 1996.
Serrano et al., *Nature*, 366:704-707, 1993.
Serrano et al., *Science*, 267(5195):249-252, 1995.
Sestier et al, *Electrophoresis*, 19:1220-1226, 1998.
Spandidos et al., *Anticancer Res.*, 9(2):383-386, 1989.
Stayton et al., *J. Controlled Release*, 65:203-220, 2000.
Sun et al., *Biopolymers*, 60(1):61-75, 2001.
Templeton, *Nature Biotech.*, 15:647-652, 1997.
Templeton, *Nature Biotechnology*, 15:647-652, 1997.
Travali et al., *FASEB J*, 4(14):3209-3214, 1990.
Tsujimoto and Croce, *Proc. Nail. Acad. Sci. USA*, 83(14):5214-5218, 1986.
Tsujimoto et al., *Science*, 228(4706):1440-1443, 1985.
Uno et al., *Cancer Research*, 64:2969-2976, 2004.
Uzawa et al., *Cancer Genet. Cytogenet.*, 107:125-131, 1998.
Virmani et al., *Genes Chrom Cancer*, 21:308-319, 1998.
Wang, *Oncogene*, 19(49):5643-5650, 2000.
Weinberg, *Science*, 254(5035):1138-1146, 1991.
Weinberg, *Science*, 254:1138-1146, 1991.
Wen and Van Etten, *Genes and Development*, 11:2456-2467, 1997.
West, *Methods in Molec. Biol.*, 238:113-122, 2004.
Wilhelm et al., *Biomaterials*, 24:1001-1011, 2003.
Wistuba et al., *Cancer Res.*, 57:3154-3158, 1997.
Wistuba et al., *Cancer Res.*, 59:1973-1979, 1999.
Wistuba et al., *Oncogene*, 18:643-650, 1999.
Woodring et al., *J. Cellular Science*, 116(Pt.13):2613-2626, 2003.
Zbar et al., *Nature*, 327:721-724, 1987.
Arlinghaus, *Oncogene*, 21:8560-8567, 2002.
Brasher and Van Etten, *J. Biol. Chem.*, 275:35631-35637, 2000.
Donaldson et al., *Proc. Natl. Acad. Sci. USA*, 99:14053-14058, 2002.
Druker et al., *Nature Med.*, 2:561-566, 1996.
Guo et al., *Blood*, 83:3629-3637, 1994.
Hantschel et al., *Cell*, 112:845-957, 2003.
Heisterkamp et al., *Nature*, 344:251-253, 1990.
Ji et al., *Cancer Res.*, 62:2715-2720, 2002.
Kondo et al., *Oncogene*, 20:6258-6262, 2001.
Lerman and Minna, Cancer Res., 60:6116-6133, 2000.
Ling et al., *Cancer Res.*, 63:298-303, 2003.
Plattner et al., *Genes and Dev.*, 13:2400-2411, 1999.
Taagepera et al., *Proc. Natl. Acad. Sci. USA*, 95:7457-7462, 1998.
Uno et al., *Cancer Res.*, 64:2969-2976, 2004.
Wang, *Oncogene*, 19:5643-5650, 2000.
Wen and Van Etten, *Genes and Dev.*, 11:2456-2467, 1997.
Woodring et al., *J. Cell Biol.*, 165:493-503, 2004.
Zabarovsky et al., *Oncogene*, 21:6915-6935, 2002.
Zipfel et al., *Current Biol.*, 14:1222-1231, 2004.

---

What is claimed is:

1. A method of delivering a FUS-1 polypeptide to a cell, comprising contacting a cell with a nanoparticle-polypeptide complex comprising one or more FUS-1 polypeptides, wherein the one or more FUS-1 polypeptides:
   (1) comprise the sequence of KLRRVHKNLPPQG-PVKLDHPR (SEQ ID NO:13);
   (2) comprise the sequence of VLRRVHVNLPPQGPVV-LDHPR (SEQ ID NO:14);
   (3) comprise the sequence of ETPVTVNGQVRAPLR-RVHV (SEQ ID NO:17);
   (4) consists of the sequence of KLRRVHKNLIPQ-GIVKLDHPR (SEQ ID NO:1); or
   (5) consists of the sequence of ETIVTKNGQKRAKLR-RVHK (SEQ ID NO:16)
   wherein the one or more FUS-1 polypeptides are each modified by the addition of a chemical moiety to facilitate uptake into the cell.

2. The method of claim 1, wherein the FUS-1 polypeptide contains no more than 30 amino acids.

3. The method of claim 2, wherein the FUS-1 polypeptide contains no more than 24 amino acids.

4. The method of claim 1, wherein the FUS-1 polypeptide comprises KLRRVHKNLPPQGPVKLDHPR (SEQ ID NO:13).

5. The method of claim 1, wherein the FUS-1 polypeptide comprises VLRRVHVNLPPQGPVVLDHPR (SEQ ID NO:14).

6. The method of claim 1, wherein the FUS-1 polypeptide comprises ETPVTVNGQVRAPLRRVHV (SEQ ID NO:17).

7. The method of claim 1, wherein the FUS-1 polypeptide consists of KLRRVHKNLIPQGIVKLDHPR (SEQ ID NO:1).

8. The method of claim 1, wherein the FUS-1 polypeptide consists of ETIVTKNGQKRAKLRRVHK (SEQ ID NO:16).

9. The method of claim 1, wherein the nanoparticle is a lipid-based nanoparticle, a superparamagnetic nanoparticle, a nanoshell, a semiconductor nanocrystal, a quantum dot, a polymer-based nanoparticle, a silicon-based nanoparticle, a silica-based nanoparticle, a metal-based nanoparticle, a fullerene or a nanotube.

10. The method of claim 9, wherein the nanoparticle is a lipid-based nanoparticle.

11. The method of claim 9, wherein the lipid-based nanoparticle is a liposome, a neutral liposome, a DOPC liposome or a DOTAP:cholesterol vesicle.

12. The method of claim 11, wherein the liposome is a DOPC liposome.

13. The method of claim 9, wherein the nanoparticle is a superparamagnetic nanoparticle.

14. The method of claim 9, wherein the nanoparticle is a superparamagnetic nanoparticle, and the nanoparticle-polypeptide complex is within a liposome or a DOTAP:cholesterol vesicle.

15. The method of claim 14, wherein the liposome is a DOPC liposome.

16. The method of claim 1, wherein the chemical moiety is a $C_4$-$C_{18}$ fatty acid.

17. The method of claim 16, wherein the fatty acid is stearate or myristate.

18. The method of claim 1, wherein each FUS-1 polypeptide is coupled or fused to a cell-penetrating peptide selected from the group consisting of an HIV Tat peptide, a herpes virus VP22 peptide, and a Drosophila Antennapedia homeobox gene product.

19. The method of claim 1, wherein the FUS-1 polypeptide is attached to a $C_4$-$C_{18}$ fatty acid that is a stearate moiety, and the nanoparticle is a DOTAP:cholesterol vesicle, a DOPC liposome or a superparamagnetic nanoparticle.

20. The method of claim 1, wherein the FUS-1 polypeptide is a peptide of from 19 to 100 amino acid residues in length.

21. The method of claim 20, wherein the peptide is from 21 to 100 amino acid residues in length.

22. The method of claim 1, wherein the cell is in a subject, and contacting comprises administering to the subject a composition comprising the nanoparticle-polypeptide complex.

23. The method of claim 1, wherein the subject has a tumor, and the cell is a tumor cell.

24. The method of claim 23, wherein the tumor is a lung cancer.

25. The method of claim 24, wherein the lung cancer is a NSCLC.

26. The method of claim 22, wherein administering comprises intraperitoneal injection.

27. The method of claim 23, wherein the tumor is gastrointestinal.

28. The method of claim 1, wherein the chemical moiety to facilitate uptake into the cell is a fatty acid.

29. The method of claim 1, wherein the chemical moiety to facilitate uptake into the cell is a cell penetrating peptide.

30. The method of claim 29, wherein the cell penetrating peptide is an HIV Tat peptide, a herpes virus VP22 peptide, or a Drosophila Antennapedia homeobox gene product.

31. A method of delivering a FUS-1 polypeptide to a cell, comprising contacting a cell with a nanoparticle-polypeptide complex comprising a FUS-1 polypeptide consisting of KLRRVHKNLIPQGIVKLDHPR (SEQ ID NO:1), wherein the FUS-1 polypeptide is modified at the N-terminal Lysine residue by either (i) the attachment of a $C_4$-$C_{18}$ fatty acid to facilitate cellular uptake or (ii) the coupling or fusing of a cell-penetrating peptide selected from the group consisting of an HIV Tat peptide, a herpes virus VP22 peptide, and a Drosophila Antennapedia homeobox gene product.

* * * * *

UNITED STATES PATENT AND TRADEMARK OFFICE
CERTIFICATE OF CORRECTION

PATENT NO. : 8,338,366 B2
APPLICATION NO. : 11/375544
DATED : December 25, 2012
INVENTOR(S) : Jacki Lin et al.

It is certified that error appears in the above-identified patent and that said Letters Patent is hereby corrected as shown below:

In the Specifications:

In column 1, lines 10-12, delete
"The government owns rights in the present invention pursuant to grant number P50CA70907-07 from the NIH, and DAMD17002-1-0706 from the DOD."
and insert
--This invention was made with Government support under grant number P50CA70907-07 awarded by the National Institutes of Health and DAMD17002-1-0706 awarded by the Department of Defense. The Government has certain rights in the invention.-- therefor.

Signed and Sealed this
Sixth Day of August, 2013

Teresa Stanek Rea
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 8,338,366 B2 | Page 1 of 1 |
| APPLICATION NO. | : 11/375544 | |
| DATED | : December 25, 2012 | |
| INVENTOR(S) | : Lin et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1411 days.

Signed and Sealed this
Sixteenth Day of December, 2014

Michelle K. Lee
*Deputy Director of the United States Patent and Trademark Office*